US009221731B2

(12) United States Patent
Imura et al.

(10) Patent No.: US 9,221,731 B2
(45) Date of Patent: Dec. 29, 2015

(54) METHOD FOR PRODUCING 1-CHLORO-3,3,3-TRIFLUORO-1-PROPENE AND 1,3,3,3-TETRAFLUOROPROPENE

(71) Applicant: CENTRAL GLASS COMPANY, LIMITED, Ube, Yamaguchi (JP)

(72) Inventors: Hideaki Imura, Kawagoe (JP); Satoru Okamoto, Kawagoe (JP); Masamune Okamoto, Kawagoe (JP); Naoto Takada, Kawagoe (JP); Fuyuhiko Sakyu, Kawagoe (JP)

(73) Assignee: CENTRAL GLASS COMPANY, LIMITED, Ube, Yamaguchi (JP)

( * ) Notice: Subject to any disclaimer, the term of this patent is extended or adjusted under 35 U.S.C. 154(b) by 0 days.

(21) Appl. No.: 14/564,606

(22) Filed: Dec. 9, 2014

(65) Prior Publication Data
US 2015/0099907 A1 Apr. 9, 2015

Related U.S. Application Data

(63) Continuation of application No. PCT/JP2013/066395, filed on Jun. 13, 2013.

(30) Foreign Application Priority Data

Jun. 13, 2012 (JP) .................. 2012-134054
Jun. 19, 2012 (JP) .................. 2012-137704
Jun. 19, 2012 (JP) .................. 2012-137705
Jun. 19, 2012 (JP) .................. 2012-137706
Nov. 13, 2012 (JP) .................. 2012-249198

(51) Int. Cl.
*C07C 17/358* (2006.01)
*C07C 17/383* (2006.01)
(Continued)

(52) U.S. Cl.
CPC .............. *C07C 17/358* (2013.01); *C07C 17/38* (2013.01); *C07C 17/383* (2013.01);
(Continued)

(58) Field of Classification Search
CPC ...................................................... C07C 17/358
See application file for complete search history.

(56) References Cited

U.S. PATENT DOCUMENTS 6,018,084 A 1/2000 Nakada
6,111,150 A 8/2000 Sakyu
(Continued)

FOREIGN PATENT DOCUMENTS

EP 0939071 A1 9/1999
JP H09-183740 A 7/1997
(Continued)

OTHER PUBLICATIONS

I.L.Knunyants et al., Reactions of Fluoro Olefins, Bulletin of the Academy of Sciences of the USSR, Division of chemical science, Aug. 1960, vol. 9, Issue 8, pp. 1312-1317, Kluwer Academic Publishers-Plenum Publishers, USSR.
(Continued)

*Primary Examiner* — Jafar Parsa
*Assistant Examiner* — Medhanit Bahta
(74) *Attorney, Agent, or Firm* — Lowe Hauptman & Ham, LLP

(57) ABSTRACT

A method for producing a desired isomer of 1-chloro-3,3,3-trifluoro-1-propene or a desired isomer of 1,3,3,3-tetrafluoropropene at a high conversion ratio with no use of a solid catalyst is provided. Since no solid catalyst is used, a desired isomer of 1-chloro-3,3,3-trifluoro-1-propene and a desired isomer of 1,3,3,3-tetrafluoropropene can be stably obtained with no undesired possibility that the solid catalyst is deteriorated due to coking or the like caused as a result of long-time use thereof.

15 Claims, 10 Drawing Sheets

(51) Int. Cl.
*C07C 21/18* (2006.01)
*C07C 17/38* (2006.01)
*C11D 7/50* (2006.01)
*C11D 7/30* (2006.01)
*C09K 3/30* (2006.01)
*C09K 5/04* (2006.01)

(52) U.S. Cl.
CPC ............... *C11D 7/5018* (2013.01); *C09K 3/30* (2013.01); *C09K 5/044* (2013.01); *C09K 5/045* (2013.01); *C11D 7/30* (2013.01)

(56) References Cited

U.S. PATENT DOCUMENTS

| | | |
|---|---|---|
| 2010/0145112 A1 | 6/2010 | Ishihara |
| 2010/0152504 A1 | 6/2010 | Hulse |
| 2010/0163781 A1 | 7/2010 | Sharratt |
| 2010/0256426 A1 | 10/2010 | Sakyu |
| 2011/0218370 A1 | 9/2011 | Elsheikh |
| 2011/0270001 A1 | 11/2011 | Ishihara |
| 2012/0059199 A1 | 3/2012 | Pokrovski |

FOREIGN PATENT DOCUMENTS

| | | |
|---|---|---|
| JP | H10-7605 A | 1/1998 |
| JP | H11-140002 A | 5/1999 |
| JP | H11-180908 A | 7/1999 |
| JP | 2000-007592 A | 1/2000 |
| JP | 2008-285471 A | 11/2008 |
| JP | 2009-108049 A | 5/2009 |
| JP | 2010-523635 A | 7/2010 |
| JP | 2010-202640 A | 9/2010 |
| JP | 2012-509324 A | 4/2012 |
| JP | 2012-512160 A | 5/2012 |

OTHER PUBLICATIONS

Kurt W. Egger et al., Iodine and Nitric Oxide Catalyzed Isomerization of Olefins. V. Kinetics of the Geometrical Isomerization of 1,3-Pentadiene, a Check on the Rate of Rotation about Single Bonds, and the Allylic Resonance Energy, Journal of the American Chemical Society, 1965, vol. 87(15), pp. 3314-3319, California, USA.

English translation of International Search Report for PCT/JP2013/066395 mailed Sep. 3, 2013.

English translation of International Preliminary Report for PCT/JP2013/066395 issued on Dec. 16, 2014.

English translation of Written Opinion for PCT/JP2013/066395 mailed Sep. 3, 2013.

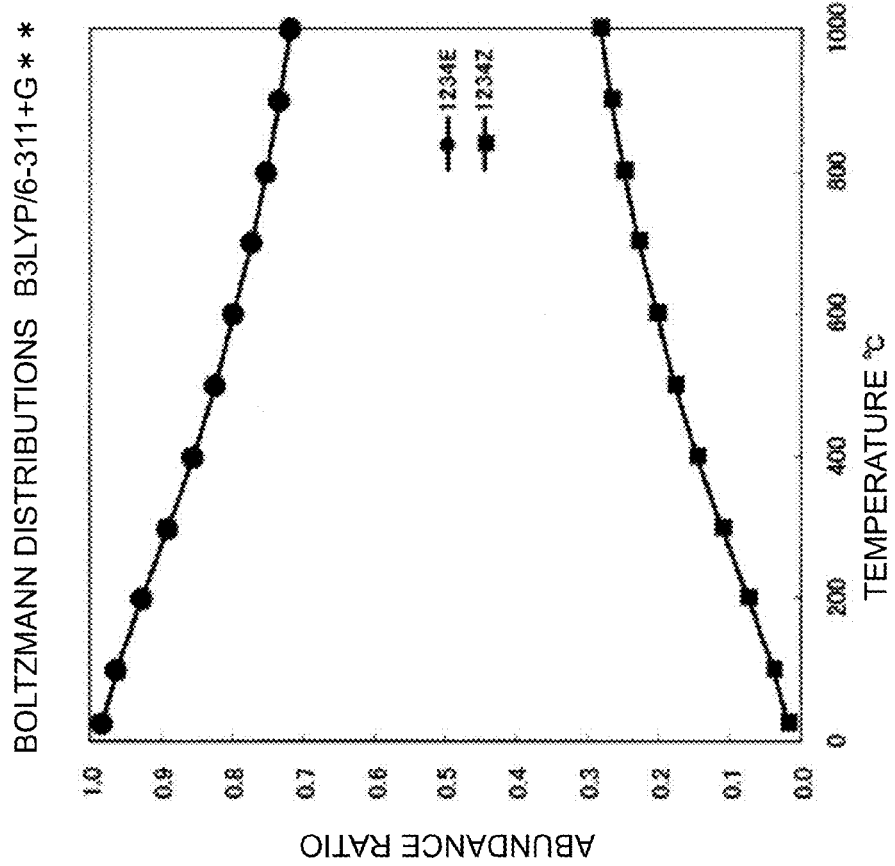

METHOD FOR PRODUCING 1-CHLORO-3,3,3-TRIFLUORO-1-PROPENE AND 1,3,3,3-TETRAFLUOROPROPENE

CROSS REFERENCE TO RELATED APPLICATION

This application is based upon and claims the benefit of priority from Japanese Patent Applications No. 2012-134054 filed on Jun. 13, 2012, No. 2012-137704 filed on Jun. 19, 2012, No. 2012-137705 filed on Jun. 19, 2012, No. 2012-137706 filed on Jun. 19, 2012 and No. 2012-249198 filed on Nov. 13, 2012 and the prior PCT Application PCT/JP2013/066395 filed on Jun. 13, 2013, the entire contents of which are incorporated herein by reference.

FIELD

The present invention relates to a method for producing 1-chloro-3,3,3-trifluoro-1-propene and 1,3,3,3-tetrafluoropropene, and specifically to a method for producing a desired isomer of each of 1-chloro-3,3,3-trifluoro-1-propene and 1,3,3-tetrafluoropropene.

BACKGROUND

Among fluorine-containing organic compounds (fluorocarbons), organic compounds having a double bond in a molecule are known to have a very short atmospheric lifetime because of the double bond and have substantially no influence on global warming and depletion of ozone layer, and thus to be useful as a functional substance such as a washing detergent, a solvent, a foaming agent, a coolant, a spray, a working fluid or the like or as an intermediate for any of various functional products.

Organic compounds which are known to contain fluorine having a double bond in a molecule include, for example, 1-chloro-3,3,3-trifluoro-1-propene and 1,3,3,3-tetrafluoropropene. The following methods for producing 1,3,3,3-tetrafluoropropene are disclosed. Izvest. Akad. Nauk S.S.S.R., Otdel. Khim. Nauk. page 1312, 1960 discloses a method by which 1,1,1,3,3-pentafluoropropane is subjected to dehydrofluorination by use of potassium hydroxide in dibutylether. Japanese Patent Laid-Open No. H10-7605 discloses a method by which 1-chloro-3,3,3-trifluoropropene is fluorinated by hydrogen fluoride in the presence of a Ti/C catalyst or a Cr/C catalyst. Japanese Patent Laid-Open No. H11-140002 discloses a method by which 1,1,1,3,3-pentafluoropropane is put into contact with carbon or metal-supported carbon in a reaction temperature range raised by a gas phase to cause dehydrofluorination.

Japanese Patent Laid-Open No. H9-183740 discloses a method by which 1,1,1,3,3-pentachloropropane is reacted with hydrogen fluoride in a gas phase to produce 1-chloro-3,3,3-trifluoro-1-propene. Japanese Patent Laid-Open No. H11-180908 discloses a method by which 1,1,1,3,3-pentachloropropane is reacted with hydrogen fluoride with no catalyst to produce 1-chloro-3,3,3-trifluoro-1-propene.

An organic compound containing fluorine and having a double bond in a molecule such as 1-chloro-3,3,3-trifluoro-1-propene, 1,3,3,3-tetrafluoropropene or the like contains cis-trans isomers. By the methods for producing 1,3,3,3-tetrafluoropropene disclosed in Japanese Patent Laid-Open No. H10-7605, Japanese Patent Laid-Open No. H11-140002 and Izvest. Akad. Nauk S.S.S.R., Otdel. Khim. Nauk. page 1312, 1960 described above, 1,3,3,3-tetrafluoropropene is usually obtained in the form of a mixture of a cis isomer (hereinafter, may be referred to as "1234Z") and a trans isomer (hereinafter, may be referred to as "1234E") (hereinafter, the mixture of 1234E and 1234Z may be referred to as "1234" or "1234EZ"; or in the case where it is not intended to distinguish whether the isomer is a cis isomer or a trans isomer, the isomer will be referred to as "1234" or "1234EZ"). Similarly, by the methods for producing 1-chloro-3,3,3-trifluoro-1-propene disclosed in Japanese Patent Laid-Open No. H9-183740 and Japanese Patent Laid-Open No. H11-180908, 1-chloro-3,3,3-trifluoro-1-propene is usually obtained in the form of a mixture of a cis isomer (hereinafter, may be referred to as "1233Z") and a trans isomer (hereinafter, may be referred to as "1233E") (a mixture of 1233Z and 1233E may be referred to as "1233" or "1233EZ"; or in the case where it is not intended to distinguish whether the isomer is a cis isomer or a trans isomer, the isomer will be referred to as "1233" or "1233EZ"). The trans isomer, which is thermodynamically stable, is a main component in obtained 1-chloro-3,3,3-trifluoro-1-propene. However, in an organic compound containing fluorine and having a double bond in a molecule, either one of the cis isomer or the trans isomer may be used.

In the case of, for example, 1-chloro-3,3,3-trifluoro-1-propene, the trans isomer and the cis isomer have different boiling points (the boiling point of the trans isomer is 19° C.; and the boiling point of the cis isomer is 39° C.). Whether the trans isomer is desired or the cis isomer is desired depends on the use of 1-chloro-3,3,3-trifluoro-1-propene. When 1-chloro-3,3,3-trifluoro-1-propene is used for a washing detergent or the like, the cis isomer (boiling point: 39° C.), which is easy to handle at room temperature, is mainly used from the viewpoint of volatility. By contrast, when 1-chloro-3,3,3-trifluoro-1-propene is used for a foaming agent or the like, the trans isomer (boiling point: 19° C.) is mainly used. Japanese Patent Laid-Open No. 2008-285471 discloses a method for producing 3,3,3-trifluoropropyne, by which cis-1-halogeno-3,3,3-trifluoropropene is reacted with a base. It is described that when the trans isomer is used as a material, the reaction does not progress at all; whereas when the cis isomer is used as a material, trifluoropropyne is obtained at a high yield. As can be seen from this, the cis isomer and the trans isomer have different properties.

As can be seen, the compound obtained by the production method disclosed in each of Japanese Patent Laid-Open No. H10-7605 through Japanese Patent Laid-Open No. H11-180908 and Izvest. Akad. Nauk S.S.S.R., Otdel. Khim. Nauk. page 1312, 1960 has a double bond in a molecule and thus is a mixture of a cis isomer and a trans isomer. This is disadvantageous in the case where either one of the cis isomer or the trans isomer is desired.

In such a situation, it has been attempted to perform mutual conversion of a cis isomer and a trans isomer of an organic compound containing fluorine and having a double bond in a molecule by use of an isomerization reaction. For example, Japanese Patent Laid-Open No. 2010-523635 discloses a method by which E-(hydrohalo)fluoroalkene, which is a trans isomer, is put into contact with a solid catalyst such as a Lewis acid catalyst, a chromia-containing catalyst, an alumina catalyst or the like by a gas phase reaction by utilization of an equilibrium reaction to be isomerized into Z-(hydrohalo)fluoroalkene, which is a cis isomer. Japanese Patent Laid-Open No. 2009-108049 discloses a method by which cis-1,3,3,3-tetrafluoropropene is put into contact with a solid catalyst such as a fluorinated chromia catalyst, an aluminum fluoride catalyst or the like by a gas phase reaction by utilization of an equilibrium reaction to be isomerized into trans-1,3,3,3-tetrafluoropropene. Japanese Patent Laid-Open No. 2012-509324 discloses a method by which cis-1-chloro-3,3, 3-trifluoropropene is isomerized into trans-1-chloro-3,3,3-trifluoropropene in the presence of a homogenous or non-homogenous catalyst. It is also disclosed that an oxidizer such as oxygen or chlorine is added in order to extend the life of the catalyst. Japanese Patent Laid-Open No. 2012-512160 discloses a mutual conversion method by which trans-1-chloro-3,3,3-trifluoropropene or cis-1-chloro-3,3,3-trifluoropropene is isomerized on a surface of a heated solid catalyst or the like in a specific temperature range by utilization of an equilibrium reaction. United States Patent Application Publication No. 2010/0152504 discloses an isomerization method by which trans-1-chloro-3,3,3-trifluoropropene is converted into cis-1-chloro-3,3,3-trifluoropropene by utilization of an equilibrium reaction. Journal of the American Chemical Society, vol. 15, pp. 3314-3319 (1965) discloses an example in which the isomerization rate of 1,3-pentadiene is examined by use of nitrogen monoxide (NO) as a radical source. However, as shown by the Markovnikov's rule or the anti-Markovnikov's rule, olefin formed of only hydrocarbon such as 1,3-pentadiene or the like and olefin containing a plurality of halogen atoms as substituents often exhibit different reaction behaviors. No case has been reported in which an olefin containing a plurality of halogen atoms as substituents such as 1-chloro-3,3,3-trifluoropropene or the like is isomerized by a radical. Japanese Patent Laid-Open No. 2010-202640 discloses a method for purifying cis-1-chloro-3,3,3-trifluoropropene.

Japanese Patent Laid-Open No. 2010-523635 discloses a method by which trans-(hydrohalo)fluoroalkene is put into contact with a solid catalyst such as a Lewis acid catalyst, a chromia-containing catalyst, an alumina catalyst or the like to be isomerized into cis-(hydrohalo)fluoroalkene by a gas phase reaction. However, a fluoroalkene such as 1,3,3,3-tetrafluoropropene or the like has a double bond between carbon atoms, and therefore is likely to be coked on a surface of a solid catalyst such as an alumina catalyst or the like. Since such a fluoroalkene covers an active point to reduce catalyst activity over time, the catalyst is inevitably deteriorated. This has a problem that the catalyst needs to be regenerated.

Japanese Patent Laid-Open No. 2009-108049 discloses a method by which cis-1,3,3,3-tetrafluoropropene is put into contact with a solid catalyst such as a fluorinated chromia catalyst, an aluminum fluoride catalyst or the like by a gas phase reaction to be isomerized into trans-1,3,3,3-tetrafluoropropene. As described above, a fluoroalkene such as 1,3,3,3-tetrafluoropropene or the like has a double bond between carbon atoms, and therefore is likely to be coked on a surface of a solid catalyst such as an alumina catalyst or the like. Since such a fluoroalkene covers an active point to reduce catalyst activity over time, the catalyst is inevitably deteriorated. This has a problem that the catalyst needs to be regenerated.

A Boltzmann distribution of 1,3,3,3-tetrafluoropropene was found by a hybrid functional method (B3LYP/6–311+G**) (see FIG. 1). According to the Boltzmann distribution, on the low temperature side, the abundance ratio of the trans isomer) (1234E), which was thermodynamically stable, was predominant. It is possible to perform an isomerization reaction of a trans isomer (1234E) into a cis isomer (1234Z) or of a cis isomer (1234Z) into a trans isomer (1234E) with no use of a solid isomerization catalyst. However, such a catalyst-free isomerization reaction has a problem of not being efficient because the conversion ratio of the trans isomer is several percent as the one-pass yield (yield per cycle) and thus the same reaction needs to be repeated several times to several ten times in order to obtain a practically high yield of the cis isomer (composition close to equilibrium). Similarly, in the case of such a catalyst-free isomerization reaction, the conversion ratio of the cis isomer (1234Z) is several percent as the one-pass yield and thus the same reaction needs to be repeated several times to several ten times in order to obtain a practically high yield of the trans isomer (composition close to equilibrium).

Japanese Patent Laid-Open No. 2012-509324 discloses a method by which cis-1-chloro-3,3,3-trifluoro-1-propene is isomerized into trans-1-chloro-3,3,3-trifluoro-1-propene in the presence of a solid catalyst such as an alumina catalyst or the like. However, as described above, a fluoroolefin having a double bond is, in general, likely to be coked on a surface of a solid catalyst. Since such a fluoroolefin covers an active point to reduce catalyst activity over time, the catalyst is inevitably deteriorated. Thus, the catalyst needs to be regenerated.

Japanese Patent Laid-Open No. 2012-512160 discloses a mutual conversion method of isomers of 1-chloro-3,3,3-trifluoro-1-propene. Example 2 describes an example of isomerizing a trans isomer into a cis isomer in the absence of a catalyst. A Boltzmann distribution of 1-chloro-3,3,3-trifluoro-1-propene was found by a hybrid functional method (B3LYP/6–311+G**) (see FIG. 1). According to the Boltzmann distribution, on the low temperature side, the abundance ratio of the trans isomer)(1234E), which was thermodynamically stable, was predominant. It is possible to perform an isomerization reaction of a trans isomer (1233E) into a cis isomer (1233Z) or of a cis isomer (1233Z) into a trans isomer (1233E) with no use of a solid isomerization catalyst. However, such a catalyst-free isomerization reaction has a problem of not being an efficient process because the conversion ratio of the trans isomer is merely 1 to 2% as the one-pass yield and thus the same reaction needs to be repeated several times to several ten times in order to obtain a practically high yield of the cis isomer (composition close to equilibrium). Similarly, in the case of such a catalyst-free isomerization reaction, the conversion ratio of the cis isomer is several percent as the one-pass yield and thus the same reaction needs to be repeated several times to several ten times in order to obtain a practically high yield of the trans isomer (composition close to equilibrium).

In a comparative example in Japanese Patent Laid-Open No. 2012-512160, trans-1-chloro-3,3,3-trifluoro-1-propene having bromine added thereto is irradiated with light in a liquid phase in an attempt to realize isomerization into a cis isomer. However, the conversion ratio is low and it is difficult to obtain a practically high yield.

In United States Patent Application Publication No. 2010/0152504, 1-chloro-3,3,3-trifluoro-1-propene is put into contact to a surface of a catalyst or the like that is heated to a temperature in a limited range of 150° C. to 350° C. to perform an isomerization reaction. In the presence of a catalyst, the isomerization progresses quickly up to a point of thermodynamic equilibrium or in the vicinity thereof. By contrast, a catalyst-free isomerization reaction is not efficient because the conversion ratio of the trans isomer is about 2% per pass and thus the same reaction needs to be repeated several times to several ten times in order to obtain a practically high yield. In addition, United States Patent Application Publication No. 2010/0152504 does not include any description on a method for highly purifying the cis isomer, which is the target compound.

In such a situation, an efficient mutual conversion method of cis-trans isomers of an organic compound containing fluorine and having a double bond in a molecule such as 1-chloro-3,3,3-trifluoro-1-propene, 1,3,3,3-tetrafluoropropene or the like regardless of presence/absence of a solid catalyst is now desired.

SUMMARY

The present invention made in light of the above-described problems has an object of providing a method for producing a desired isomer of 1-chloro-3,3,3-trifluoro-1-propene, at a high conversion ratio regardless of presence/absence of a solid catalyst, that includes isomerizing trans-1-chloro-3,3,3-trifluoro-1-propene into cis-1-chloro-3,3,3-trifluoro-1-propene or isomerizing cis-1-chloro-3,3,3-trifluoro-1-propene into trans-1-chloro-3,3,3-trifluoro-1-propene.

The present invention also has an object of providing a method for producing a desired isomer of 1,3,3,3-tetrafluoropropene, at a high conversion ratio regardless of presence/absence of a solid catalyst, that includes isomerizing trans-1,3,3,3-tetrafluoropropene into cis-1,3,3,3-tetrafluoropropene or isomerizing cis-1,3,3,3-tetrafluoropropene into trans-1,3,3,3-tetrafluoropropene.

When 1-chloro-3,3,3-trifluoro-1-propene is produced by use of 1,1,3,3,3-pentachloropropane as a material, the resultant product usually contains 244fa, 1335 and 235da in addition to 1233EZ. The boiling points of 244fa, 1335 and 235da, which are impurities, are close to that of 1233Z, and thus the resultant product exhibits an azeotrope(-like) behavior. For this reason, it is not possible to extract highly pure 1233Z from the crude 1233EZ. The present invention has another object of providing a separation and purification method for obtaining highly pure 1233Z from the crude 1233EZ in a simple manner.

According to an embodiment of the present invention, a method for producing a compound represented by a general formula (2), the method comprising isomerizing at least a part of a compound represented by a general formula (1) in a material composition into the compound represented by the general formula (2) by heating the material composition containing at least the compound represented by the general formula (1) in the presence of a radical generating agent is provided:

[Chemical formula 1]

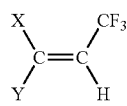
(1)

[Chemical formula 2]

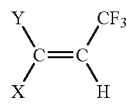
(2)

(in the general formulas (1) and (2), X and Y are each a fluorine atom (F) or a hydrogen atom (H), and X and Y are not the same as each other; or X and Y are each a chlorine atom (Cl) or a hydrogen atom (H), and X and Y are not the same as each other).

When in the general formulas (1) and (2), X is a hydrogen atom (H) and Y is a chlorine atom (Cl), the method may include, before the isomerizing:

reacting 1,1,1,3,3-pentachloropropane with hydrogen fluoride to generate a first composition containing compounds represented by the general formula (1) and the general formula (2) and at least one compound selected from 3-chloro-1,1,1,3-tetrafluoropropane (244fa), 2-chloro-1,1,1,3,3-pentafluoropropane (235da), and 1-chloro-1,1,4,4-pentafluoro-2-butene (1335);

removing the compound represented by the general formula (2) from the first composition by distillation; and removing the at least one compound selected from 3-chloro-1,1,1,3-tetrafluoropropane, 2-chloro-1,1,1,3,3-pentafluoropropane, and 1-chloro-1,1,4,4-pentafluoro-2-butene by distillation from the first composition deprived of the compound represented by the general formula (2) to provide the compound represented by the general formula (1).

The radical generating agent may be at least one selected from the group including chlorine, oxygen, bromine, air, hydrogen peroxide, ozone, nitrogen oxide, and carbon halide.

The isomerizing may be performed in a gas phase.

The isomerizing may be performed in the absence of a solid catalyst.

The isomerizing may be performed in an empty column of a gas phase flow system.

The radical generating agent may be added in an amount, with respect to the compound represented by the general formula (1), higher than or equal to 0.0001 mol % and lower than or equal to 10 mol %.

When in the general formulas (1) and (2), X is a hydrogen atom (H) and Y is a fluorine atom (F), the material composition may be heated at a temperature higher than or equal to 150° C. and lower than or equal to 700° C. in isomerizing.

When in the general formulas (1) and (2), X is a fluorine atom (F) and Y is a hydrogen atom (H), the material composition may be heated at a temperature higher than or equal to 150° C. and lower than or equal to 700° C. in isomerizing.

When in the general formulas (1) and (2), X is a hydrogen atom (H) and Y is a chlorine atom (Cl), the material composition may be heated at a temperature higher than or equal to 150° C. and lower than or equal to 800° C. in isomerizing.

When in the general formulas (1) and (2), X is a chlorine atom (Cl) and Y is a hydrogen atom (H), the material composition may be heated at a temperature higher than or equal to 150° C. and lower than or equal to 800° C. in isomerizing.

According to an embodiment of the present invention, a method for producing a compound represented by a general formula (2), the method comprising isomerizing at least a part of a compound represented by a general formula (1) in a material composition into the compound represented by the general formula (2) by heating the material composition containing at least the compound represented by the general formula (1) in the absence of a catalyst to a temperature higher than or equal to 450° C. and lower than or equal to 700° C. and setting a residence time to longer than or equal to 0.01 seconds and shorter than or equal to 50 seconds is provided:

[Chemical formula 3]

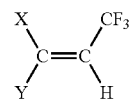
(1)

[Chemical formula 4]

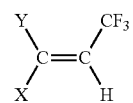
(2)

(in general formulas (1) and (2), X and Y are each a chlorine atom (Cl) or a hydrogen atom (H), and X and Y are not the same as each other).

The residence time may be longer than or equal to 0.1 seconds and shorter than or equal to 10 seconds.

According to an embodiment of the present invention, a method for producing a compound represented by a general formula (2), the method comprising isomerizing at least a part of a compound represented by a general formula (1) in a material composition into the compound represented by the general formula (2) by heating the material composition containing at least the compound represented by the general formula (1) in the absence of a catalyst to a temperature higher than or equal to 500° C. and lower than or equal to 900° C. and setting a residence time to longer than or equal to 0.01 seconds and shorter than or equal to 50 seconds is provided:

[Chemical formula 5]

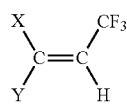
(1)

[Chemical formula 6]

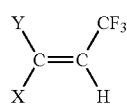
(2)

(in general formulas (1) and (2), X and Y are each a fluorine atom (F) or a hydrogen atom (H), and X and Y are not the same as each other).

The residence time may be longer than or equal to 0.1 seconds and shorter than or equal to 10 seconds.

According to the present invention, a desired isomerization reaction of each of 1-chloro-3,3,3-trifluoro-1-propene and 1,3,3,3-tetrafluoropropene is performed with a high conversion ratio even with no use of a solid catalyst. Therefore, a desired isomer of each of 1-chloro-3,3,3-trifluoro-1-propene and 1,3,3,3-tetrafluoropropene can be stably obtained with no undesired possibility that the solid catalyst is deteriorated due to coking caused as a result of long-time use thereof.

BRIEF DESCRIPTION OF THE DRAWINGS

FIG. 10 shows an example of calculation of a Boltzmann distribution of 1,3,3,3-tetrafluoropropene (1234).

DESCRIPTION OF EMBODIMENTS

Figure 1:
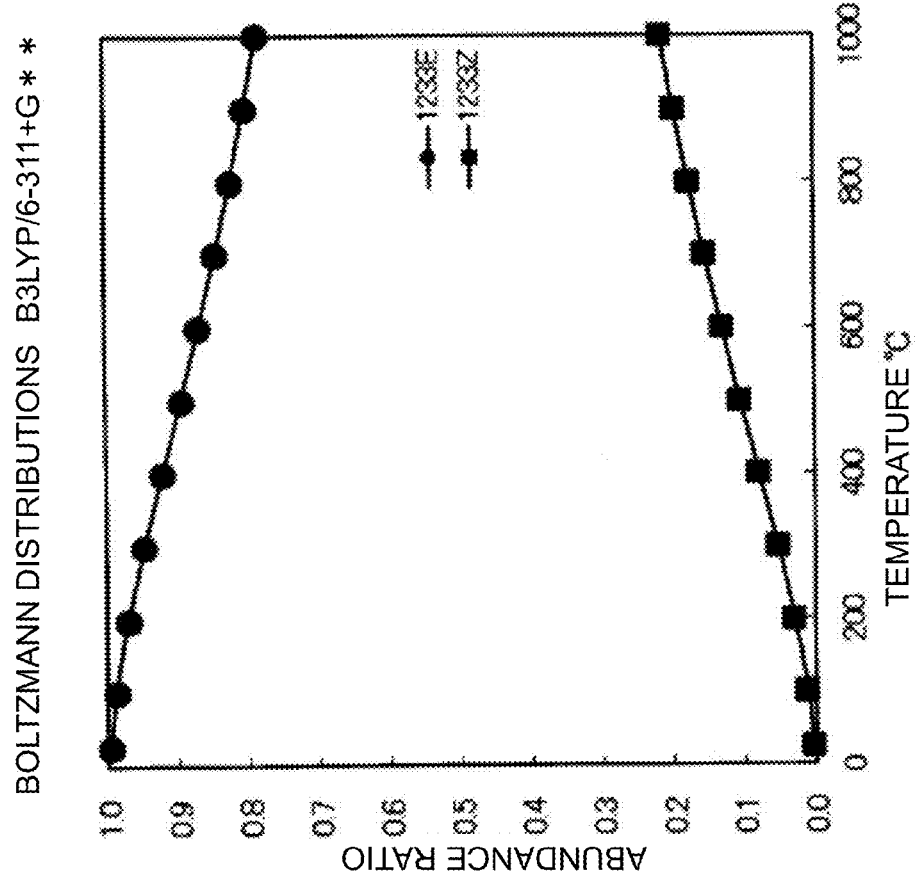
FIG. 1 shows an example of calculation of a Boltzmann distribution of 1-chloro-3,3,3-trifluoro-1-propene (1233)

As a result of active studies performed in order to solve the above-described problems, the present inventors found the following. When, in a cis-trans isomerization reaction of 1-chloro-3,3,3-trifluoro-1-propene, a compound that generates a radical, namely, a radical generating agent, is present in a reaction system, the radical acts as a catalyst so that even with no use of a solid catalyst, a desired isomerization reaction of 1-chloro-3,3,3-trifluoro-1-propene progresses in a low temperature range of 200° C. to 400° C., in which it is usually difficult to progress the isomerization, and a high conversion ratio is provided. Thus, the present inventors achieved the present invention.

The present inventors also found the following. When, in a cis-trans isomerization reaction of 1,3,3,3-tetrafluoropropene, a radical generating agent is present in a reaction system, the radical acts as a catalyst so that even with no use of a solid catalyst, a desired isomerization reaction of 1,3,3,3-tetrafluoropropene progresses in a low temperature range of 200° C. to 400° C., in which it is usually difficult to progress the isomerization, and a high conversion ratio is provided. Thus, the present inventors achieved the present invention.

Hereinafter, a method according to the present invention for producing a desired isomer of each of 1-chloro-3,3,3-trifluoro-1-propene and 1,3,3,3-tetrafluoropropene that includes an isomerization reaction of a cis or trans isomer of each of 1-chloro-3,3,3-trifluoro-1-propene and 1,3,3,3-tetrafluoropropene will be described in detail. The present invention can be optionally modified without departing from the gist thereof. All the publications cited in this specification, for example, prior art documents, laid-open publications, patent publications and the like are incorporated herein by reference.

Hereinafter, a cis isomer of 1-chloro-3,3,3-trifluoro-1-propene will be referred to as "1233Z"; and a trans isomer thereof will be referred to as "1233E". A mixture of a cis isomer and a trans isomer thereof will be referred to as "1233" or "1233EZ". In the case where it is not intended to distinguish whether the isomer is a cis isomer or a trans isomer, the isomer will be referred to also as "1233" or "1233EZ". Similarly, a cis isomer of 1,3,3,3-tetrafluoropropene will be referred to as "1234Z"; and a trans isomer thereof will be referred to as "1234E". A mixture of a cis isomer and a trans isomer thereof will be referred to as "1234" or "1234EZ". In the case where it is not intended to distinguish whether the isomer is a cis isomer or a trans isomer, the isomer will be referred to also as "1234" or "1234EZ".

The isomerization reaction in the presence of a radical according to the present invention is to convert (isomerize) 1233Z into 1233E, 1233E into 1233Z, 1234Z into 1234E, or 1234E into 1234Z in a state where a catalytic amount of radical is present in a reaction system. In a state where no radical is present in a low temperature range higher than or equal to or 200° C. and lower than or equal to 400° C., the isomerization reaction of 1233 or 1234 does not substantially progress. However, when a trace amount of radical generating agent is added, the isomerization reaction quickly progresses, which is a feature of the present invention. Since the radical acts as a catalyst efficiently in the isomerization reaction, no solid catalyst is specifically needed. In this specification, a "solid catalyst" refers to a solid isomerization catalyst.

One of the cis-trans isomers of each of 1-chloro-3,3,3-trifluoro-1-propene (1233) and 1,3,3,3-tetrafluoropropene (1234) can be represented by the following general formula (1).

[Chemical formula 7]

(1)

When general formula (1) represents 1233, X and Y are each a chlorine atom (Cl) or a hydrogen atom (H), and X and Y are not the same as each other. When general formula (1) represents 1234, X and Y are each a fluorine atom (F) or a hydrogen atom (H), and X and Y are not the same as each other.

The other of the cis-trans isomers of each of 1233 and 1234 can be represented by the following general formula (2).

[Chemical formula 8]

(2)

When general formula (2) represents 1233, X and Y are each a chlorine atom (Cl) or a hydrogen atom (H), and X and Y are not the same as each other. When general formula (2) represents 1234, X and Y are each a fluorine atom (F) or a hydrogen atom (H), and X and Y are not the same as each other.

Namely, the present invention is directed to a method for producing a compound represented by general formula (2), the method comprising isomerizing at least a part of the material compound represented by general formula (1) in a material composition into the target compound represented by general formula (2) by heating the material composition containing at least the compound represented by general formula (1) in the presence of a radical generating agent:

[Chemical formula 9]

(1)

[Chemical formula 10]

(2)

(in general formulas (1) and (2), X and Y are each a fluorine atom (F) or a hydrogen atom (H), and X and Y are not the same as each other; or X and Y are each a chlorine atom (Cl) or a hydrogen atom (H), and X and Y are not the same as each other).

According to the present invention, the isomerization reaction is to cause the equilibrium ratio of a target compound (compound represented by general formula (2)): a material compound (compound represented by general formula (1)) to achieve the thermodynamic equilibrium point quickly by a catalytic action of a radical. When the isomer ratio of the material compound:target compound (i.e., material compound/target compound) is higher than the equilibrium ratio, at least a part of the material compound is converted into the target compound. When a material having a high content of the target compound is used, the apparent conversion ratio from the material compound into the target compound is decreased.

As described above, the present inventors has found that as long as a radical can be generated in a reaction system in a predetermined temperature range, a desired isomerization reaction of 1233 and 1234 can be progressed. In the present invention, the term "radical" refers to a chemical species such as an atom or a molecule, an ion or the like which have unpaired electron and encompasses a radical cation having a positive charge, a radical anion having a negative charge, and a radical having a neutral charge, a biradical and a carbene and the like. Specifically, the radical may be a fluorine radical, a chlorine radical, a bromine radical, an iodine radical, an oxygen radical, a hydrogen radical, a hydroxy radical, a nitroxide radical, a nitrogen radical, an alkyl radical, a difluoro carbene, a carbon radical or the like.

There is no specific limitation on the method for generating a radical in a reaction system. For example, a radical may be generated by light, heat or a catalyst. When a radical is to be generated by light, a sensitizer or the like is may be used. According to a method in an embodiment of the present invention that is preferable from the viewpoint of operability or simplicity, a substance that easily generates a radical by provision of external energy, namely, a radical generating agent, is added.

According to the present invention, any radical generating agent that generates a radical when being provided with external energy of light, heat or the like is usable with no specific limitation. A preferable radical generating agent generates a radical easily in a reaction system. Specific examples of such a radical generating agent include halogen gas such as chlorine, bromine and the like; oxygen-containing gas such as air, oxygen, ozone, hydrogen peroxide, nitrogen oxide and the like; carbon halide; and the like. Carbon halide has a part of, or the entirety of, hydrogen atoms in an alkane such as methane, ethane, propane, butane, pentane, hexane or the like, an alkene such as ethene, propene, butene, pentene, hexene, or the like, or an alkyne such as ethyne, propyne, butyne, pentyne, hexyne or the like, substituted with fluorine, chlorine, bromine or iodine atoms. Thus, carbon halide contains at least one chlorine, bromine or iodine atom. Examples of carbon halide, which is usable as a radical generating agent, do not include the material contained in the material composition of the present invention, namely, 1233 or 1234. A compound containing four or more fluorine atoms may make it difficult to cause radical cleavage. In such a case, it is desired to optionally optimize the conditions for generating a radical such as temperature or the like.

Specific examples of carbon halide include $CH_3Cl$, $CH_2Cl_2$, $CHCl_3$, $CCl_4$, $CH_3CH_2Cl$, $CH_3CCl_3$, $CH_2ClCH_2Cl$, $CH_2=CCl_2$, $CHCl=CCl_2$, $CCl_2=CCl_2$, $CHCl_2CHCl_2$, $CCl_3CH_2Cl$, $CH_3CH_2CH_2Cl$, $CH_3CHClCH_3$, $CH_3CHClCH_2Cl$, $CH_3Br$, $CH_2Br_2$, $CHBr_3$, $CBr_4$, $CH_3CH_2Br$, $CH_3CBr_3$, $CH_2BrCH_2Br$, $CH_2=CBr_2$, $CHBr=CBr_2$, $CBr_2=CBr_2$, $CHBr_2CHBr_2$, $CBr_3CH_2Br$, $CH_3CH_2CH_2Br$, $CH_3CHBrCH_3$, $CH_3CHBrCH_2Br$, $CH_3I$, $CH_2I_2$, $CHI_3$, $CH_3CH_2I$, $CH_3Cl_3$, $CH_2ICH_2I$, $CH_2=Cl_2$, $CHI=Cl_2$, $Cl_2=Cl_2$, $CHI_2CHI_2$, $Cl_3CH_2I$, $CH_3CH_2CH_2I$, $CH_3CHICH_3$, $CH_3CHICH_2I$, $CF_2HCl$, $CF_3I$, $CF_2I_2$, $CF_3Br$, and $CF_2Br_2$.

Among the above-listed radical generating agents, oxygen, air or chlorine is preferable as a radical generating agent for the low cost and availability thereof. It should be noted that chlorine is preferable as a radical generating agent but is highly corrosive and thus needs to be washed to be removed with a reductant-containing basic aqueous solution or the like after the isomerization reaction. When halogen or carbon halide is used, a trace amount of halide may be produced as a byproduct, which makes it difficult to realize purification. When, for example, 1234Z is to be converted into 1234E by isomerization by use of a radical, and halogen or carbon halide is used as a radical generating agent, a trace amount of halide of 1234E is produced as a byproduct, which makes it difficult to purify 1234E. By contrast, air and oxygen are easily separable from the resultant product and thus are especially preferable as a radical generating agent.

Method for putting a radical into contact with a material containing a material compound by a gas phase reaction include, for example, a method of providing a radical generating agent with light or heat to activate the radical generating agent beforehand and then introducing the radical generating agent into a reaction tube, a method of introducing a mixture of a radical generating agent and a material containing a material compound into a reaction tube and then activating the mixture with light or heat, and the like. For putting a radical into contact with the material efficiently, it is desirable to supply a radical generating agent and a material containing a material compound to a reaction tube at the same time in the form of a mixture. When a material containing a material compound is to be supplied, inert gas such as nitrogen or the like may be supplied, together with the material, in an amount that is sufficiently small so as not to decrease the productivity. From an industrial viewpoint, it is simple and preferable that a mixture of a radical generating agent and a material containing a material compound is put into a heated reaction tube and is provided with thermal energy in the reaction tube to generate a thermal radical.

The generation of a radical occurs in a chain-reacting manner. Therefore, it is preferable that a radical generating agent is supplied to a reaction system in a trace amount. Adding an excessive amount of radical generating agent is a waste of the sub material and also imposes, after the reaction, a load on a step of separating the radical generating agent from the material compound and/or the target compound. Even when air, which is relatively easily separable, is added in a large amount, the capability of a condensation step or a distillation step is lowered. When an excessive amount of chlorine as a radical generating agent is added to a reaction system, a compound containing chlorine added to the double bond is produced as a byproduct. Especially, a compound containing chlorine added to 1233E or 1234E is HCFC, which causes global warming or depletion of ozone layer. Therefore, it is more preferable that the amount of a byproduct containing chlorine is smaller.

Hereinafter, a method for producing a desired isomer of 1-chloro-3,3,3-trifluoro-1-propene (1233) including a cis (1233Z)-trans (1233E) isomerization step or a trans (1233E)-cis (1233Z) isomerization step of 1-chloro-3,3,3-trifluoro-1-propene (1233), and a method for producing a desired isomer of 1,3,3,3-tetrafluoropropene (1234) including a cis (1234Z)-trans (1234E) isomerization step or a trans (1234E)-cis (1234Z) isomerization step of 1,3,3,3-tetrafluoropropene, will each be described in detail.

Method for producing
cis-1-chloro-3,3,3-trifluoro-1-propene (1233Z)

Trans-1-chloro-3,3,3-trifluoro-1-propene (1233E), which is a material of cis-1-chloro-3,3,3-trifluoro-1-propene (1233Z), may be a pure trans isomer (1233E) or a mixture containing a cis isomer (1233Z) and a trans isomer (1233E). A trans isomer (1233E) that is produced by a known method is usable. For example, a mixture of a trans isomer (1233E) and a cis isomer (1233Z) obtained by reacting 1,1,1,3,3-pentachloropropane (240fa) with hydrogen fluoride in a gas phase, or a composition obtained by subjecting the mixture into a known purification process, is usable.

A mixture of 1233E and 1233Z that is obtained by reacting 1,1,1,3,3-pentachloropropane (240fa) with hydrogen fluoride may occasionally contain 3-chloro-1,1,1,3-tetrafluoropropane (also referred to as "244fa") or 2-chloro-1,1,1,3,3-pentafluoropropane (also referred to as "235da"), each of which is usually difficult to be separated by distillation from 1233Z. However, the isomerization of the present invention can be performed with no need to separate 244fa or 2-chloro-1,1,1,3,3-pentafluoropropane (235da), which is difficult to be separated by distillation, from 1233Z. This is an advantage of the present invention. There is no problem even when a byproduct derived from the production of a material to be used is contained.

Usually, trans-1-chloro-3,3,3-trifluoro-1-propene obtained by a known production method is a mixture containing a trans isomer (1233E) and a cis isomer (1233Z). The ratio of 1233E and 1233Z depends on thermodynamic equilibrium. As shown by the calculation example of the Boltzmann distributions in FIG. 1, the equilibrium ratio depends on temperature conditions. The ratio of a trans isomer (1233E) and a cis isomer (1233Z) actually measured tends to be the same as the calculated value, but the absolute value of the measured value may be occasionally different from that of the calculated value. The equilibrium ratio also varies in accordance with the type or shape of the reaction vessel, or the reaction conditions such as the presence/absence of the catalyst and the like.

An isomerization reaction of trans-1-chloro-3,3,3-trifluoro-1-propene (1233E) into cis-1-chloro-3,3,3-trifluoro-1-propene (1233Z) is to cause the equilibrium ratio of 1233E:1233Z to achieve the thermodynamic equilibrium point quickly by a catalytic action of a radical. Therefore, when a material having a high content of 1233Z is used, the apparent conversion ratio from 1233E into 1233Z is decreased.

When 1233Z is to be obtained as the target compound, it is ideal to use pure 1233E as a material, but it is acceptable to use 1233EZ containing 1233Z in a material composition. Considering to equilibrium, it is more preferable that the content of 1233Z in the material composition is lower. The ratio of 1233E in the material composition is higher than or equal to 50% by weight, preferably higher than or equal to 70% by weight, and more preferably higher than or equal to 90% by weight. It is more preferable that the mass ratio of 1233Z/1233E in the material is closer to zero. Specifically, the mass ratio of 1233Z/1233E is preferably 0 to 0.2, and more preferably 0 to 0.1. When 1233Z is the target compound, the material is 1233E. Therefore, the content of 1233E cannot be zero.

1233E and 1233Z can be easily separated from each other by distillation because of the difference in the boiling point. Therefore, when a mixture of 1233E and 1233Z is used as a material, it is preferable to separate 1233Z by distillation so that a material composition having a high content of 1233E is used. It is preferable to distill the mixture of 1233Z and 1233E to separate 1233Z and 1233E from each other so that 1233Z is used as a product and 1233E is used as a material.

It is reasonable and preferable from the viewpoint of efficient use of the material that a product containing 1233Z obtained by the isomerization of the present invention is collected, 1233E and 1233Z are isolated from each other by distillation or the like, and then unreacted 1233E is reused as the material. Reuse of the unreacted 1233E as the material allows 1233E to be converted into 1233Z efficiently.

In an isomerization step of 1233E into 1233Z, an isomerization reaction of converting 1233E into 1233Z is progressed by generating a radical in a reaction system in a predetermined temperature range. According to a preferable method for generating a radical in a system, a radical generating agent is added to the system as described above. A radical generating agent may be at least one selected from halogen gas such as chlorine, bromine and the like; oxygen-containing gas such as air, oxygen, ozone, hydrogen peroxide, nitrogen oxide and the like; and carbon halide. An especially preferable radical generating agent is air or oxygen. The details of the carbon halide is described above and will not be described here. Examples of carbon halide, which is usable as a radial generating agent, do not include 1-chloro-3,3,3-trifluoro-1-propene (1233), which is the material of the present invention.

According to a method for putting a radical into contact with a material composition containing 1233E by a gas phase reaction, a radical generating agent may be provided with light or heat to be activated beforehand and then introduced into a reaction tube, or a mixture of a radical generating agent and a material composition containing 1233E may be introduced into a reaction tube and then activated with light or heat. For putting a radical into contact with 1233E efficiently, it is preferable to supply a radical generating agent and a material composition containing 1233E to a reaction tube at the same time in the form of a mixture. When a material composition containing 1233E is to be supplied, inert gas such as nitrogen or the like may be supplied, together with the material composition, in an amount that is sufficiently small so as not to decrease the productivity. From an industrial viewpoint, it is simple and preferable that a mixture of a radical generating agent and a material composition containing 1233E is put into a heated reaction tube and is provided with thermal energy in the reaction tube to generate a thermal radical.

Specifically, according to a preferable method for producing 1233Z as the target compound, a mixture containing trans-1-chloro-3,3,3-trifluoropropene (1233E) and at least one radical generating agent selected from the group including chlorine, oxygen, bromine, air, hydrogen peroxide, ozone, nitrogen oxide, and carbon halide is heated to isomerize trans-1-chloro-3,3,3-trifluoropropene (1233E) into cis-1-chloro-3,3,3-trifluoropropene (1233Z) by an isomerization reaction caused in the presence of a radical. The isomerization reaction caused in the presence of the radical converts at least a part of trans-1-chloro-3,3,3-trifluoropropene (1233E) into cis-1-chloro-3,3,3-trifluoropropene (1233Z), so that the ratio of the cis-1-chloro-3,3,3-trifluoropropene (1233Z) with respect to the trans-1-chloro-3,3,3-trifluoropropene (1233E) can be increased.

The generation of a radical occurs in a chain-reacting manner. Therefore, it is preferable that a radical generating agent is supplied in a trace amount. Provision of an excessive amount of radical generating agent is a waste of the sub material and also imposes, after the reaction, a load on a step of separating the radical generating agent from 1233. Even when air, which is relatively easily separable, is added in a large amount, the capability of a condensation step or a distillation step is lowered. When an excessive amount of chlorine as a radical generating agent is added, a compound containing chlorine added to the double bond is produced as a byproduct. Especially, a compound containing chlorine added to 1233 is HCFC, which causes global warming or depletion of ozone layer. Therefore, it is more preferable that the amount of a byproduct containing chlorine is smaller.

The present inventors performed an experiment with the ratio of the radical generating agent to the material composition being varied. As a result, even when the amount of chlorine was decreased down to the lower limit of measurement of the chlorine flowmeter, no substantial influence was recognized on the conversion ratio from 1233E into 1233Z. From this, it has been found that the amount of the radical generating agent may be an extremely trace amount (experimental results will be described later). It should be noted that, as described above, the optimal amount of the radical generating agent depends on the type of the radical generating agent or the structure of the reaction tube. For example, the order of the activity level of air, oxygen and chlorine is chlorine>oxygen>air. Also, it is important to put the radical generated from the radical generating agent into contact with 1233E. The probability at which 1233E and the radical contact each other depends on the diameter or length of the reaction tube or the presence/absence of a filler such as a static mixer or the like. When a reaction tube highly suitable for the mixing is used, a desired conversion ratio is achieved even with a trace amount of radical generating agent. In other cases, the amount of the radical generating agent to be added may be increased to raise the concentration of the radical, so that the conversion ratio is increased.

As described above, the amount of the radical generating agent depends on the type of the radical generating agent or the shape of the reaction tube. Usually, the amount of the radical generating agent with respect to 1233E, which is the material, is preferably higher than or equal to 0.0001 mol and lower than or equal to 10 mol %, and more preferably higher than or equal to 0.0001 mol % and lower than or equal to 0.005 mol %. When a reaction tube highly suitable for putting the radical into contact with 1233E is used, 1233E and the radical can collide against each other sufficiently. Therefore, the amount of the radical generating agent with respect to 1233E is preferably higher than or equal to 0.0001 mol % and lower than or equal to 0.005 mol %.

A reaction tube highly suitable for putting the radical into contact with 1233E has, for example, a filler that is inactive to the reaction, such as a static mixer, a Raschig ring, a Pall ring, a metal mesh or the like, packed therein. According to the present invention, the filler may be packed in the reaction tube, needless to say. On the other hand, a reaction tube having a high length/inner diameter ratio allows the radical and 1233E to be put into contact with each other efficiently even when being empty with no filler as described above and also has high heat conductivity, and thus is especially preferable. A preferable material of the reaction tube or the like is carbon, ceramics, stainless steel, nickel, a nickel alloy (trade name: Hastelloy™, Inconel™, Monel™), or the like. Regarding an alloy containing iron as a main component, it is usually more preferable that an iron content is lower and a content of nickel, chromium or the like is higher because the alloy has a higher corrosion resistance with such a composition. When the reaction tube is to be used for a small device, a quartz tube or the like may be used as the reaction tube. A reaction tube with no filler may be used. When desired, a static mixer may be used, or the reaction tube may be provided with a filler such as a Raschig ring, a Pall ring or the like. It is preferable that such the filler is formed of a corrosion-resistant material as described above. The length/inner diameter ratio of the reaction tube is higher than or equal to 5 and lower than or equal to 1000, and preferably higher than or equal to 20 and lower than or equal to 500. When the length/inner diameter ratio is lower than 5, the radical and 1233E may not be put into sufficient contact with each other; and when the length/inner diameter ratio is higher than 1000, the device cost may be raised, or the pressure loss may be too large in certain operation conditions. For industrial mass production, it is preferable that the inner diameter of the reaction tube is longer than or equal to 8 mm and shorter than or equal to 150 mm, and that the length of the reaction tube is longer than or equal to 1 m and shorter than or equal to 200 m. It is especially preferable that the inner diameter of the reaction tube is longer than or equal to 10 mm and shorter than or equal to 60 mm, and that the length of the reaction tube is longer than or equal to 2 m and shorter than or equal to 50 m. Especially preferably, the reaction tube is empty. There is no specific limitation on the shape of the reaction tube. The reaction tube may be straight, coiled, or folded by use of a joint or the like. In the case of small-scale laboratory-type production in which the restriction on the device and costs are ignorable, the target isomerization can be realized with no limitation on the inner diameter or the length/inner diameter ratio. When desired, a static mixer may be used, or the reaction tube may be provided with a filler such as a Raschig ring, a Pall ring or the like. When alumina or the like is to be used as a filler, it is preferable to bake the filler at, for example, a temperature higher than or equal to 1300° C. to make the filler inert, so that the filler is deprived of catalyst activity. In the case where the reaction device is to be heated, there is no specific limitation on the heating method. The reaction device may be directly heated by an electric heater or a burner, or may be indirectly heated by use of melted salt or sand.

As described above, the generation of a radical occurs in a chain-reacting manner. Therefore, at a reaction temperature at which the radical generating agent can generate a radical, even though rebinding occurs, recleavage occurs. Thus, an isomerization reaction of 1233E is promoted even with a trace amount of the radical generating agent. Namely, in a method for producing 1-chloro-3,3,3-trifluoropropene including a trans (1233E)-cis (1233Z) isomerization step of 1-chloro-3,3,3-trifluoropropene (1233), the isomerization reaction progresses even when a trace amount of the radical generating agent is added. It is more preferable that the amount of an additive, which is a sub material, is smaller. In Japanese Patent Laid-Open No. 2012-509324 described above, an equivalent amount of oxidizer such as oxygen, chlorine or the like needs to be added in order to regenerate the deteriorated catalyst, so that the life time of the catalyst is extended. In this case, the amount of additive, which is a sub material, may be too large.

In a method for producing cis-1-chloro-3,3,3-trifluoropropene (1233Z) according to the present invention, a solid catalyst is not indispensable. However, a solid catalyst may be used in order to quickly progress the isomerization reaction in the presence of a radical. Examples of the usable solid catalyst include metal, metal oxide, metal halide, activated carbon, and the like, and also a composite thereof (e.g., metal-supported activated carbon). When a solid catalyst is used in a high reaction temperature range higher than or equal to 350° C., it is preferable to use a solid catalyst that is inactivated by being baked at a temperature higher than or equal to 1300° C. in a nitrogen atmosphere because 1233E is likely to be coked on a surface of the catalyst or may generate oil.

In a method for producing cis-1-chloro-3,3,3-trifluoropropene (1233Z) according to the present invention, a solid catalyst may be used as described above. However, it is preferable to perform the isomerization reaction by use of an empty column reactor with no catalyst, filler or the like, so that the efficiency of the isomerization reaction in the presence of a radical is not decreased. The "empty column" refers to that there is no object such as a catalyst, a filler or the like in an inner space of the reactor or the reaction column. When there is an object such as a catalyst, a filler or the like in an isomerization reaction area, the generated radical may be extinguished to stop the chain reaction of the radical generation, which decreases the efficiency of the isomerization. Therefore, in a method for producing cis-1-chloro-3,3,3-trifluoropropene (1233Z) according to the present invention, it is especially preferable to perform the isomerization reaction in an empty column of a gas phase flow system (see the examples described below).

When a solid catalyst is added, there may be a non-preferable case where the radical generating agent and 1233E cause an unexpected reaction that is not an isomerization reaction, and 1233E as a reaction material is merely converted into a non-preferable byproduct and the radical generating agent is consumed for the reaction with 1233E.

As shown above by the calculation example of the Boltzmann distributions (see FIG. 1), the ratio of 1233E/1233Z is higher when the temperature is lower. The reaction temperature is usually higher than or equal to 150° C. and lower than or equal to 800° C. When 1233Z is the target compound, the reaction temperature is preferably higher than or equal to 300° C. and lower than or equal to 700° C., and more preferably higher than or equal to 360° C. and lower than or equal to 560° C. When the reaction temperature is lower than 150° C., a sufficient amount of radical is not generated, and therefore the reaction rate may be too low. By contrast, when the reaction temperature is higher than 800° C., the material or the product becomes an oily substance having a high boiling point or is coked, which is not preferable. Also when the reaction temperature is higher than 800° C., the metal reaction tube may be corroded during the isomerization reaction, which is not preferable. When air, which is recommended most highly is used as a radical generating agent, a temperature range higher than or equal to 360° C. and lower than or equal to 560° C. is most preferable.

An example of preferable embodiment may be a method of introducing an organic substance (main component: trans isomer (1233E)) heated to about 360° C. and air heated to about 360° C. into a reaction tube heated to 410° C. In this reaction, from the viewpoint of preventing corrosion, a reaction tube formed of a corrosion-resistant alloy having a low content of iron and a high content of nickel or chromium is highly corrosion-resistant even at a high temperature and thus is preferable. However, a reaction tube having a content of nickel or chromium higher than an iron content is costly. A low-cost device in which a pre-heat part for an organic material or a radical generating agent formed of stainless steel (SUS304, SUS316, SUS316L), which has a relatively high content of iron, is easily available and is low-cost, and a reaction part, in which the radical generating agent and the organic substance are put into contact with each other to actually progress an isomerization reaction, formed of a corrosion-resistant alloy having a low content of iron and a high content of nickel, chromium or the like (trade name: YUS270™, Hastelloy™, Inconel™, Monel™), etc.) are provided. When 1233E was merely heated to about 360° C. with no addition of a radical generating agent, the isomerization reaction did not progress substantially and the carburetor formed of SUS316L was not recognized to be substantially corroded (annual corrosion rate: 0.1 mm/year). Even when 1233E heated to 360° C. and inert nitrogen heated to 360° C. are introduced into a reaction tube formed of Hastelloy C270 heated to 420° C., merely about 1% of cis isomer (1233Z) is produced. When air heated to 360° C. is introduced into the reaction tube instead of nitrogen, cis isomer (1233Z) is produced in an amount about ten times larger (see the examples described later). Since the equilibrium value of 1233Z by computational chemistry is about 20%, addition of the radical generating agent is recognized to provide a conspicuous effect. Among the materials used to form the reaction tube in which the isomerization by use of the radical progresses, Hastelloy C270™ is not substantially corroded (annual corrosion rate: lower than or equal to 0.1 mm/year). By contrast, the surface formed of SUS316 having a high content of iron was observed to be stripped by corrosion within only 50 hours. As can be seen, it is preferable to use SUS316 or the like for the pre-heat part and to use Hastelloy C270 ™ for the reaction part because the amount of the high quality corrosion-resistant material can be minimized.

For the reaction, a batch system or a flow system is applicable. A gas phase flow system, which is industrially highly productive, is preferable. There is no specific limitation on the reaction pressure. It is easy to make an operation for the reaction in a range from a pressure close to normal pressure to 0.5 MPa. It should be noted that a reaction pressure higher than or equal to 1 MPa is not preferable because such a pressure requires a costly pressure-resistant device and also may cause undesirable polymerization of the material or the product.

In the case of a gas phase flow system, the productivity is usually discussed with a value obtained by dividing the capacity of the reaction zone by the material supply rate. In the case where the reaction zone is filled with a catalyst, such a value is referred to as "contact time". The term "contact time" is used for the sake of convenience although a solid catalyst is not used in the production of cis-1-chloro-3,3,3-trifluoropropene (1233Z) according to the present invention described later.

According to the present invention, any contact time is not limited as long as the isomerization progresses sufficiently. The contact time is usually longer than or equal to 0.01 seconds and shorter than or equal to 50 seconds, and preferably longer than or equal to 0.05 seconds and shorter than or equal to 20 seconds. When the contact time is shorter than the above, the conversion ratio may be significantly different from the thermodynamic equilibrium composition. By contrast, when the contact time is longer than the above, the productivity is poor or the material is turned into tar even if the conversion ratio is close to the equilibrium composition.

A mixture of 1233EZ obtained by the isomerization is washed to be deprived of the radical generating agent and an acid component, dried with zeolite or the like, and then subjected to a usual distillation operation so that 1233E and 1233Z may be isolated from each other. Unreacted 1233E obtained by the isolation may be reused as a material to be isomerized into 1233Z.

Figure 2:
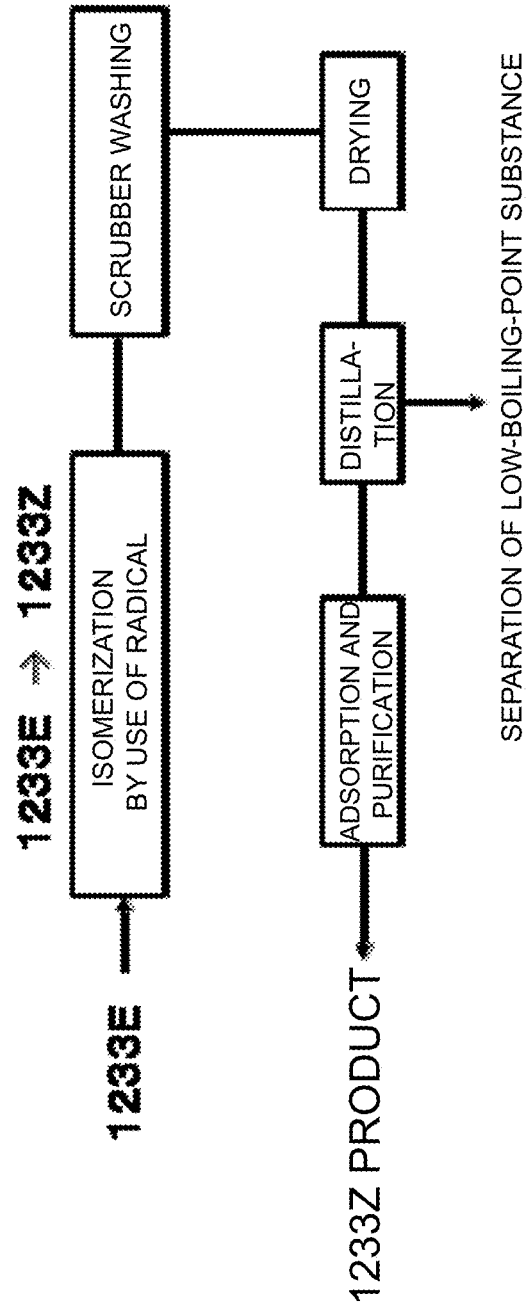
FIG. 2 is a schematic view showing an example of production process of a cis isomer (1233Z) to which an isomerization method according to the present invention is applied.

In the isomerization reaction caused by use of a radical in the method for producing cis-1-chloro-3,3,3-trifluoropropene (1233Z) according to the present invention, the process of producing the cis isomer (1233Z) as a final product can be combined with any of various steps such as distillation and separation, washing, drying and the like. There is no specific limitation on the combination of the isomerization reaction and the other steps. FIG. 2 shows an example of production steps of 1233Z that are usually performed. For the steps of distillation, washing and drying, a general system used in common steps for producing a chemical is usable with no specific limitation. For example, for the distillation operation, an appropriate continuous distillation system, batch distillation system or the like is applicable. A drying agent may be optionally selected and used.

With reference to FIG. 2, an example of a process for obtaining a cis isomer (1233Z) as the target compound from a trans isomer (1233E) as a material compound, namely, an example of a process for producing 1233Z from 1233E as the material will be described. As shown in FIG. 2, the process for producing 1233Z from 1233E may include a step of subjecting a mixture containing 1233E as a main component to an isomerization reaction by use of a radical to obtain a mixture containing 1233Z; a water-washing step of washing the resultant mixture containing the cis isomer (1233Z) with water by a scrubber system, a static mixer system, a stirring system (batch system), a bubbling system or the like; a drying step of drying the washed mixture containing 1233Z with a drying agent such as zeolite or the like; a distilling step of distilling the dried mixture by a distilling operation to separate non-target components such as a substance having a low boiling point and the like; and an adsorption purification step of removing impurities with activated carbon or the like from the mixture obtained by the distillation. The mixture obtained by the adsorption purification step is usable as a highly pure 1233Z product deprived of impurities. Between the water-washing step by the scrubber system and the drying step, another water-washing step of washing the resultant mixture with water to remove the acid component by a batch system or the like may be performed. In the steps shown in FIG. 2, the water-washing step by the scrubber system provides an effect of removing the acid component by water-washing and also an effect of cooling the generated gas. Thus, a load on a cooling device can be alleviated and the power consumption thereof can be decreased.

In the method for producing cis-1-chloro-3,3,3-trifluoropropene (1233Z) according to the present invention, the isomerization step performed by use of a radical can be combined with any of various steps such as distillation, purification, and the like with no specific limitation. Hereinafter, a method for producing cis-1-chloro-3,3,3-trifluoropropene (1233Z) by isomerization of trans-1-chloro-3,3,3-trifluoropropene (1233E) by use of a radical will be described. Specifically, as a preferable example, a process for producing 1233Z using 1,1,1,3,3-pentachloropropane (240fa) or the like as a material will be described. In the production method described below, it is especially preferable to use the above-described isomerization reaction caused by use of a radical in a third step of isomerizing a trans isomer (1233E) into a cis isomer (1233Z).

The method for producing cis-1-chloro-3,3,3-trifluoropropene (1233Z) may include the following steps.

First step: Step of reacting 1,1,1,3,3-pentachloropropane (240fa) with hydrogen fluoride to obtain a first composition containing (A) 1-chloro-3,3,3-trifluoro-1-propene (1233) and (B) at least one compound selected from 3-chloro-1,1,1, 3-tetrafluoropropane (244fa), 2-chloro-1,1,1,3,3-pentafluoropropane (235da), and 1-chloro-1,1,4,4,4-pentafluoro-2-butene (1335).

Second step: Step of removing by distillation, from the first composition obtained in the first step, at least one compound selected from 3-chloro-1,1,1,3-tetrafluoropropane (244fa), 2-chloro-1,1,1,3,3-pentafluoropropane (235da), and 1-chloro-1,1,4,4,4-pentafluoro-2-butene (1335) to obtain a second composition containing trans-1-chloro-3,3,3-trifluoropropene (1233E).

Third step: Step of isomerizing 1233E contained in the second composition obtained in the second step to obtain a third composition having an increased content of cis-1-chloro-3,3,3-trifluoropropene (1233Z).

Hereinafter, the first through third steps will be described in detail.

(1) First Step

The first step is a fluorination reaction step. Specifically, the first step is a step of reacting 1,1,1,3,3-pentachloropropane (240fa) with hydrogen fluoride to obtain the first composition containing 1-chloro-3,3,3-trifluoro-1-propene.

The substances contained in the first composition vary depending on the reaction conditions. Usually, the first composition contains (A) cis-1-chloro-3,3,3-trifluoropropene (1233Z) and trans-1-chloro-3,3,3-trifluoropropene (1233E) at a predetermined ratio. The first composition may also contain any of substances that have a boiling point close to that of 1233Z and are difficult to be separated by distillation such as (B) 3-chloro-1,1,1,3-tetrafluoropropane (244fa), 2-chloro-1,1,1,3,3-pentafluoropropane (235da), 1-chloro-1,1,4,4,4-pentafluoro-2-butene (1335) and the like.

As described above, the first composition containing 1-chloro-3,3,3-trifluoro-1-propene (1233EZ) can be obtained by reacting 1,1,1,3,3-pentachloropropane (240fa) with hydrogen fluoride by use of a known method (see Japanese Laid-Open Patent Publication No. H9-183740, Japanese Patent No. 3031456, etc.) 1,1,1,3,3-pentachloropropane (240fa), which is a material, can be obtained by adding chloroform to vinyl chloride.

(2) Second Step

The second step is a distillation step. Specifically, the second step is a step of removing by distillation, from the first composition obtained in the first step, at least one compound selected from 3-chloro-1,1,1,3-tetrafluoropropane (244fa), 2-chloro-1,1,1,3,3-pentafluoropropane (235da), and 1-chloro-1,1,4,4,4-pentafluoro-2-butene (1335) to obtain the second composition containing trans-1-chloro-3,3,3-trifluoro-1-propene (1233E) as a main component.

The first composition obtained by a fluorination reaction often contains cis-1-chloro-3,3,3-trifluoro-1-propene (1233Z) (boiling point: 39° C.), which is the target compound, and impurities such as 3-chloro-1,1,1,3-tetrafluoropropane (244fa), 2-chloro-1,1,1,3,3-pentafluoropropane (235da), 1-chloro-1,1,4,4,4-pentafluoro-2-butene (1335) and the like, each of which has a boiling point close to 40° C. and is difficult to be separated from 1233Z.

Trans-1-chloro-3,3,3-trifluoro-1-propene (1233E) has a boiling point of 19° C., which is lower than that of 1233Z as the target compound, and thus is easily separated by distillation from 244fa, 235da and 1335. Therefore, the second step allows 1233E, which does not contain impurities that are difficult to be separated by distillation, to be used as a material in the isomerization reaction in the third step. This can provide 1233Z having a higher purity.

In the case where a person of ordinary skill in the art permits incorporation of such impurities into the product, the distillation operation may be omitted. However, it is preferable that 1233E as a material in the third step (isomerization reaction) does not substantially contain impurities such as 244fa, 235da, 1335 and the like because 1233Z is usually desired to have a high purity. The expression "not substantially contain" refers to that the content of each of such impurity substances in the material composition is lower than 2%, preferably lower than 1%, more preferably lower than 0.5%, and still more preferably lower than 0.1%. The purity and the distillation efficiency of 1233Z eventually depend on the content of the impurities in the material composition containing 1233E—which is the material.

A simplest and most efficient method for removing such impurities for purification is to distill the first composition. Alternatively, the first composition may be purified by another method such as adsorption or the like. For distillation, a known method is usable. Any known method in which a packed tower, a bubble cap tower or like is used may be used. As the filler, a Heli-pack, a Raschig ring, a Pall ring or the like may be used with no specific limitation. The distillation pressure may be low pressure, normal pressure, or high pressure with no specific limitation. It is easy to perform the distillation operation at normal pressure or high pressure.

It is permitted that the material for the third step (isomerization reaction) contains 1233Z. However, the ratio of 1233E:1233Z is theoretically converged to a thermodynamic equilibrium composition. Therefore, when a large amount of 1233Z is contained in the 1233E-containing material composition, the apparent conversion ratio from 1233E into 1233Z is decreased.

The substances having a low boiling point such as 1,3,3,3-tetrafluoropropene (1234), 1,1,1,3,3-pentafluoropropane ($CF_3CH_2CHF_2$ (245fa)) and the like may be produced as byproducts by the fluorination reaction. These substances may be separated by distillation beforehand or incorporated into 1233E, which is the material for the third step (isomerization reaction) because these substances are easily separable from 1233Z, which is the target compound, by final distillation. It has been found that in the isomerization reaction conditions actively studied by the present inventors, these substances having a low boiling point are not substantially converted into substances that are difficult to be separated by distillation even at a high temperature at which an organic substance is decomposed.

As described above, the second step allows 244fa, 235da and 1335, which are difficult to be separated from 1233Z by distillation, to be removed by merely removing a fraction having a boiling point higher than that of 1233E. This facilitates the operation. The acid component and moisture may corrode the device. Thus, when 1233E containing acid component or moisture is used, it is preferable to perform pre-steps of water-washing, drying and the like.

Hereinafter, an example of procedure of the fluorination reaction step as the first step and the distillation step as the second step will be described. The method for producing cis-1-chloro-3,3,3-trifluoro-1-propene (1233Z) according to the present invention is not limited to the following procedure.

[Example of Catalyst Preparation, Activated Carbon]

0.2 liters of granular palm shell carbon having a surface area of 1200 $m^2/g$ and a pore diameter of 18 angstroms (granular Shirosagi G2X, 4 to 6 mesh; produced by Takeda Pharmaceutical Company Limited) was put into a 1-liter glass flask, warmed to a temperature of 130 to 150° C., and then deprived of moisture by a vacuum pump. At the time when extraction of moisture was recognized to stop, nitrogen was introduced into the flask to provide normal pressure.

[Example of Preparing a Material]

100 ml of activated carbon shown in example of catalyst preparation and 0.3 mol (50.4 g) of 1,1,2,2-tetrachloroethane were put into a 1-liter autoclave formed of SUS316L and provided with a reflux cooling device and a stirrer, and were kept at a temperature of 180° C. while being stirred. Hydrogen fluoride was supplied at a rate of 0.75 g/min. and 1,1,1,3,3-pentachloropropane was supplied at the rate of 0.425 g/min., to the reactor. The pressure in the system, which would have been raised by generation of hydrogen chloride along with the progress of the reaction, was kept at 1 MPa by a back-pressure valve provided in a downstream part of the reactor. The reaction was stabilized 3 hours after the start of the reaction. Therefore, the generated gas flowing out of the reactor was blown into water to remove acid gas, and then an organic substance was collected by a dry ice-acetone-trap.

The organic substance obtained by the above-described method was washed with iced water, de-watered by molecular sieves 4A, and then distilled at normal pressure in order to remove impurities such as 3-chloro-1,1,1,3-tetrafluoropropane (244fa) and the like. Thus, a fraction of 18° C. to 19° C. was obtained (the composition is shown in Table 1) as the material composition. By being analyzed, the residue in the distillation column was confirmed to contain a cis isomer (1233Z) as a main component and also 3-chloro-1,1,1,3-tetrafluoropropane (244fa), 2-chloro-1,1,1,3,3-pentafluoropropane (235da), and 1-chloro-1,1,4,4,4-pentafluoro-2-butene (1335). As a result of the fluorination reaction step and the distillation step, a trans isomer (1233E) having a purity of 99.19% and not containing impurities such as 3-chloro-1,1,1,3-tetrafluoropropane (244fa), 2-chloro-1,1,1,3,3-pentafluoropropane (235da), 1-chloro-1,1,4,4,4-pentafluoro-2-butene (1335) or the like was obtained. By use of the highly pure 1233E, obtained in the second step, in the isomerization step performed after this, highly pure 1233Z can be obtained.

(3) Third Step

The third step is an isomerization reaction step. Specifically, the third step is a step of isomerizing 1233E contained in the second composition obtained in the second step to obtain the third composition having an increased content of 1233Z which is the target compound. For the isomerization reaction step in the third step, the above-described isomerization by use of a radical is applied. When a radical generating agent is added with no use of a solid catalyst, 3-chloro-1,1,1,3-tetrafluoropropane (244fa) or 2-chloro-1,1,1,3,3-pentafluoropropane (235da), which causes azeotropy or exhibits an azeotrope-like behavior together with 1233Z as the target compound, are suppressed from being produced as a byproduct in the isomerization reaction step. Thus, there is an advantage of providing 1233Z having a higher purity.

The method for producing cis-1-chloro-3,3,3-trifluoropropene (1233Z) according to the present invention may include fourth and fifth steps described below in addition to the first through third steps described above.

(4) Fourth Step

The fourth step is a step of separating 1233Z as the target compound that is contained in the third composition obtained in the third step of 1233E and the other products also contained in the third composition.

Specifically, in the fourth step, the mixture obtained in the isomerization in the third step that contains 1233E and 1233Z as main components is water-washed by a scrubber system to be deprived of an acid component, dried with zeolite or the like, and then subjected to a normal distillation operation. In this manner, 1233Z and 1233E can be isolated from each other and each have a high purity.

A distillation column having five to 50 stages may be used, however there is no specific limitation on the number of stages of the distillation column used in the distillation operation. The purity of 1233Z is preferably higher than or equal to 98%, and more preferably higher than or equal to 99%. By applying the fourth step according to the present invention, 1233Z having a super-high purity higher than or equal to 99.9% can be easily produced.

(5) Fifth Step

The fifth step is a step of recovering 1233E separated in the fourth step and reusing the recovered 1233E in any of the first through third steps. The separated 1233E can be returned to the isomerization reaction step and/or the fluorination reaction step. Alternatively, the recovered 1233E may be provided as a product such as, for example, as hard urethane foam, with no further processing. The fifth step allows the recovered 1233E to be used effectively. Especially, the process of returning the recovered 1233E to the third step is reasonable.

Figure 3:
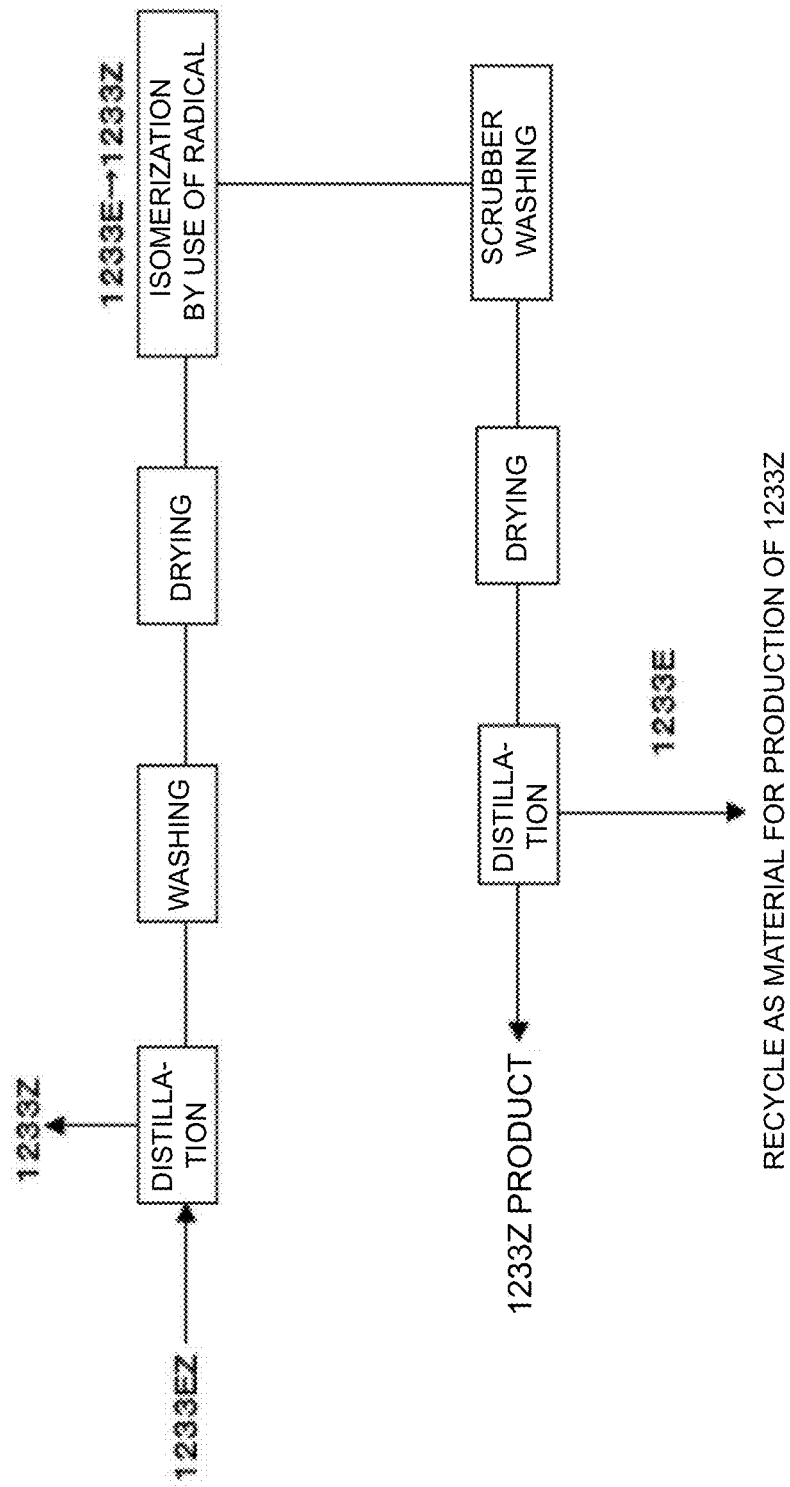
FIG. 3 is a schematic view showing an example of production process of a cis isomer (1233Z) to which an isomerization method according to the present invention is applied.

FIG. 3 shows the steps for producing 1233Z including the first through fifth steps.

Highly pure 1233Z obtained by the above-described production method is usable for any of various uses. For example, 1233Z is suitable as a washing detergent that is superb for removing fingerprints, cutting oil, silicone, machine oil, particles and the like. 1233Z does not substantially contain impurities and thus has an advantage of exerting no adverse influence due to impurity components. 1233Z is also known as being usable as a material for, for example, a trifluoropropyne such as 3,3,3-trifluoropropyne or the like (Japanese Laid-Open Patent Publication No. 2008-285471), and thus is preferably usable to produce a highly pure trifluoropropyne. 1233Z having a super-high purity higher than or equal to 99.9% does not contain impurities and is highly stable, and thus is usable for other uses. For example, the highly pure 1233Z obtained by the above-described production method is highly preferable for a working fluid in a heat pump, a heat pipe or the like or for a solar cell coolant, each of which is required to be highly stable. A "solar cell coolant" is a working fluid for natural circulation-type boiling/cooling. A natural circulation-type boiling/cooling device of a type that is installed above a solar panel is especially required to be stable against sunlight because the top plate is transparent so as to allow transmission of the sunlight.

Examples

Hereinafter, production of cis-1-chloro-3,3,3-trifluoropropene (1233Z) according to the present invention will be specifically described by way of examples. The present invention is not limited to the following examples. Herein, "%" used for a composition analysis value represents the "GC surface area %" of a composition of a reaction mixture measured by use of gas chromatography (detector: FID). Each displayed value is obtained by rounding off the numeral at the place smaller by one digit than the smallest place of the displayed value. For example, 0.00% represents a value smaller than 0.005 GC surface area %.

Figure 4:
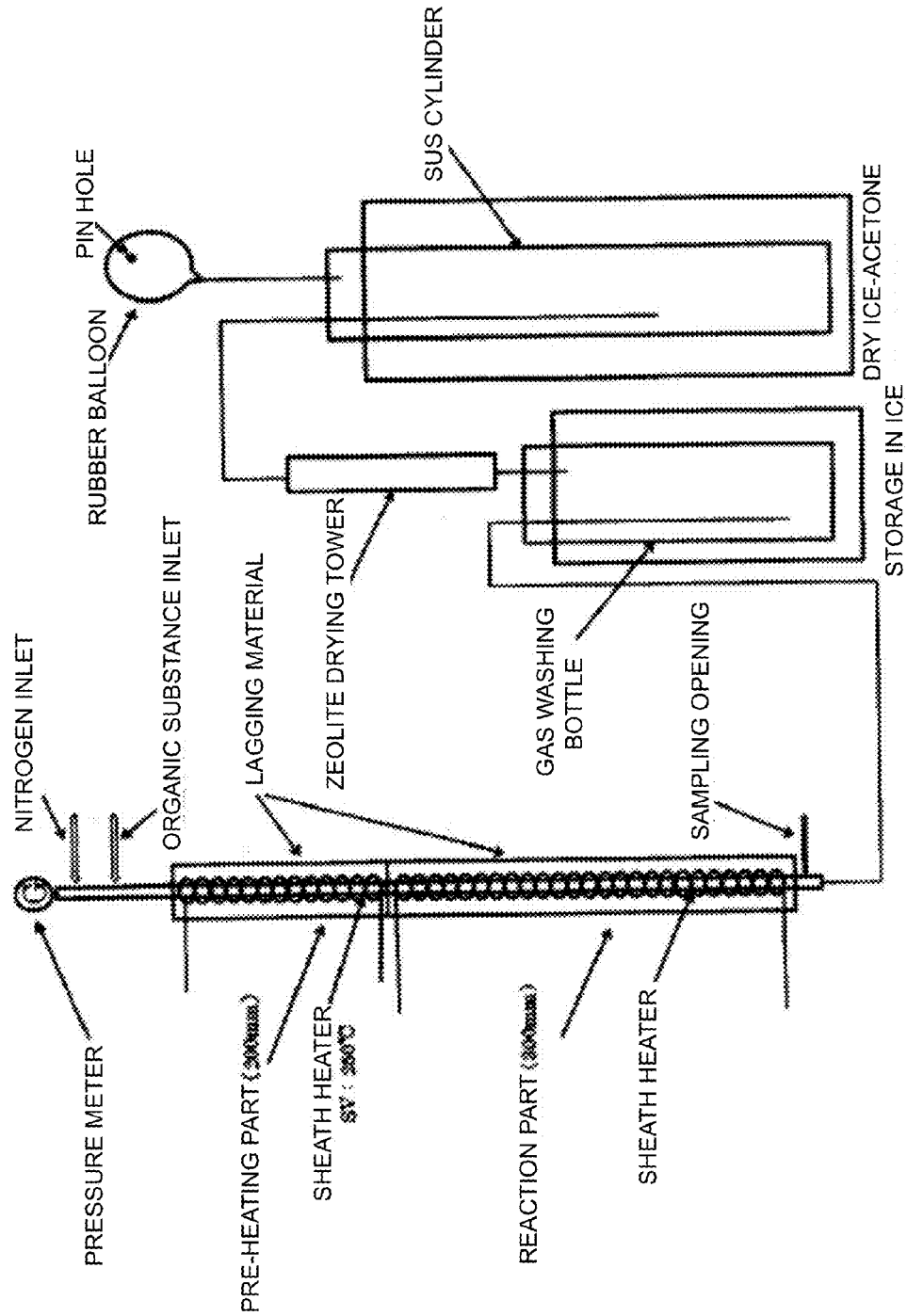
FIG. 4 is a schematic view showing an example of production apparatus for producing 1-chloro-3,3,3-trifluoro-1-propene.

An isomerization reaction of trans-1-chloro-3,3,3-trifluoropropene (1233E) was performed by use of a gas phase reaction device shown in FIG. 4. A heating part of a reaction tube and a thermocouple protection tube are formed of quartz. The reaction tube has an outer diameter of 10 mm, an inner diameter of 8 mm and a length of 500 mm, and includes the thermocouple protection tube having an outer diameter of 6 mm. The device includes two heaters so as to heat a pre-heating part (length: 120 mm) and a reaction part (length: 380 mm) independently. A space in the heating part in which the isomerization actually progresses has a capacity of 8.4 cm³. Above the reaction tube, a pressure meter, an inorganic gas inlet for nitrogen, air, chlorine or the like, and an organic material inlet for 1233E or the like are provided. Below the reaction tube, a gas sampling opening is provided. On a stage after an exit of the reaction tube, a gas washing bottle cooled with ice, a drying column, and a stainless steel trap cooled with a dry ice-acetone-trap are provided in this order. The gas washing bottle is filled with a solution obtained by dissolving 10 g of baking soda in 190 g of ion exchange water. The drying column is filled with synthetic zeolite (MS-3A). At an exit of the trap, a rubber balloon having a pin hole formed therein is provided. The reaction tube is not filled with any filler such as a catalyst or the like. The isomerization was performed in the empty column (reaction column in an empty state).

The isomerization reaction was performed in the following procedure. Nitrogen was supplied from the inorganic gas inlet, and sheath heaters in a top part and a bottom part of the reaction tube were each controlled to have a predetermined temperature by use of a PID temperature controller independently. Next, a material composition containing 1233E was introduced from the organic material inlet at a predetermined supply rate, and at the same time, the flow of nitrogen was stopped. When the reaction showed a steady state, the generated gas was sampled at the gas sampling opening. The gas was analyzed by gas chromatography. Table 1 shows the experimental conditions and the compositions of the resultant gas in examples A-1 to A-5 and comparative examples A-1 to A-3. The material composition was prepared as follows. 240fa was fluorinated in a liquid phase, water-washed and dried, and then purified by distillation. 235da, 244fa and 1335 contained in the material composition containing 1233E as a main component had a concentration lower than 0.01 mol %.

Example A-1

While nitrogen was supplied (300 ml/min.), the pre-heating part in the top part of the device was heated to 250° C. and the reaction heating part in the bottom part of the device was heated to 450° C. Then, from the material inlet, 1233E having a purity of 99.23% (content of cis isomer (1233Z): 0.09%) was supplied as a material at a supply rate of 1.27 g/min. and chlorine ($Cl_2$) as a radical generating agent was supplied at a supply rate of 4.3 ml/min. One minute later, the supply of nitrogen was stopped. Four hours later, gas was sampled from the gas sampling opening by use of a gas-tight syringe and analyzed. As the material, a mixture of 1233E and chlorine ($Cl_2$) as the radical generating agent was supplied to the reaction tube. A visual observation was performed but generation of an oil component was not found. In example A-1, the reaction tube was formed of quartz. The molar ratio of chlorine/1233E was 0.020.

Examples A-2, A-3 and A-5

Substantially the same experiments as that in example A-1 were performed except that the material supply rate was changed. Table 1 shows the reaction temperatures and the material supply rates in examples A-2, A-3 and A-5. A visual observation was performed but generation of an oil component was not found. In examples A-2 and A-3, the molar ratio of chlorine/1233E was 0.020, like in example A-1. In example A-5, the molar ratio of chlorine/1233E was 0.0020.

Example A-4

The same experiment as that in example A-3 was performed except that quartz reaction tube was replaced with an Ni reaction tube having the same size. Table 1 shows the results. A visual observation was performed but generation of an oil component was not found. No significant difference was found to be caused by the difference in the material of the reaction tube. This suggests that the effect provided by the presence of the radical is larger than the wall effect.

Comparative Examples A-1 Through A-3

In comparative examples A-1 through A-3, experiments were performed in the same conditions as those in examples A-1 through A-3 respectively, except that chlorine as the radical reacting agent was not added. When chlorine was not added, the isomerization reaction did not progress.

TABLE 1

| | 1233E introduction rate (g/min) | Chlorine introduction rate (ml/min) | Reaction temperature (° C.) | Contact time (s) | Reaction product composition (surface area %) | | |
|---|---|---|---|---|---|---|---|
| | | | | | 1233E | 1233Z | Others |
| Material | | | | | 99.23 | 0.09 | 0.68 |
| Example A-1 | 1.27 | 4.3 | 450 | 0.87 | 83.37 | 14.74 | 1.89 |
| Example A-2 | 1.14 | 3.9 | 400 | 1.12 | 85.32 | 13.45 | 1.23 |
| Example A-3 | 0.75 | 2.6 | 350 | 1.70 | 87.58 | 11.27 | 1.15 |
| Example A-4 | 0.75 | 2.6 | 350 | 1.70 | 87.48 | 11.32 | 1.20 |
| Example A-5 | 1.27 | 0.4 | 450 | 0.87 | 83.21 | 15.34 | 1.45 |
| Comparative example A-1 | 1.27 | 0.0 | 450 | 0.88 | 97.81 | 1.13 | 1.06 |
| Comparative example A-2 | 1.13 | 0.0 | 400 | 1.07 | 98.34 | 0.06 | 1.60 |
| Comparative example A-3 | 0.75 | 0.0 | 350 | 1.74 | 98.48 | 0.46 | 1.06 |

Referring to the results in examples A-1 through A-5 and comparative examples A-1 through A-3, it has been found that when chlorine as a radical generating agent is used with no use of a solid catalyst, the isomerization reaction of 1233E into 1233Z progresses to provide a high conversion ratio. In each of examples A-1 through A-5, almost no byproduct containing chlorine added to 1233E or 1233Z was detected from the reaction product obtained as a result of the isomerization reaction according to the present invention. In the present invention, even when chlorine is added as a radical generating agent, $CF_3$—CHCl—$CHCl_2$, which is generated by adding chlorine to 1233E, is produced as a byproduct at merely a content of about 0.1%. From this, it is understood that a side reaction is unlikely to occur and the isomerization reaction progresses as a main reaction in the present invention.

From example A-5, it has been found that even when chlorine gas as a radical generating agent is added in a trace amount that is the lower limit for measurement, the isomerization reaction of 1233E into 1233Z progresses to provide a high conversion ratio. Referring to comparative examples A-1 through A-3, even when a radical generating agent was not added, the isomerization reaction of 1233E into 1233Z slightly progressed, but the conversion ratio of 1233E was several percent, which was not sufficient.

Comparative Example A-4

Confirmation of Isomerization of 1233E in a Pre-Heater

Figure 5:
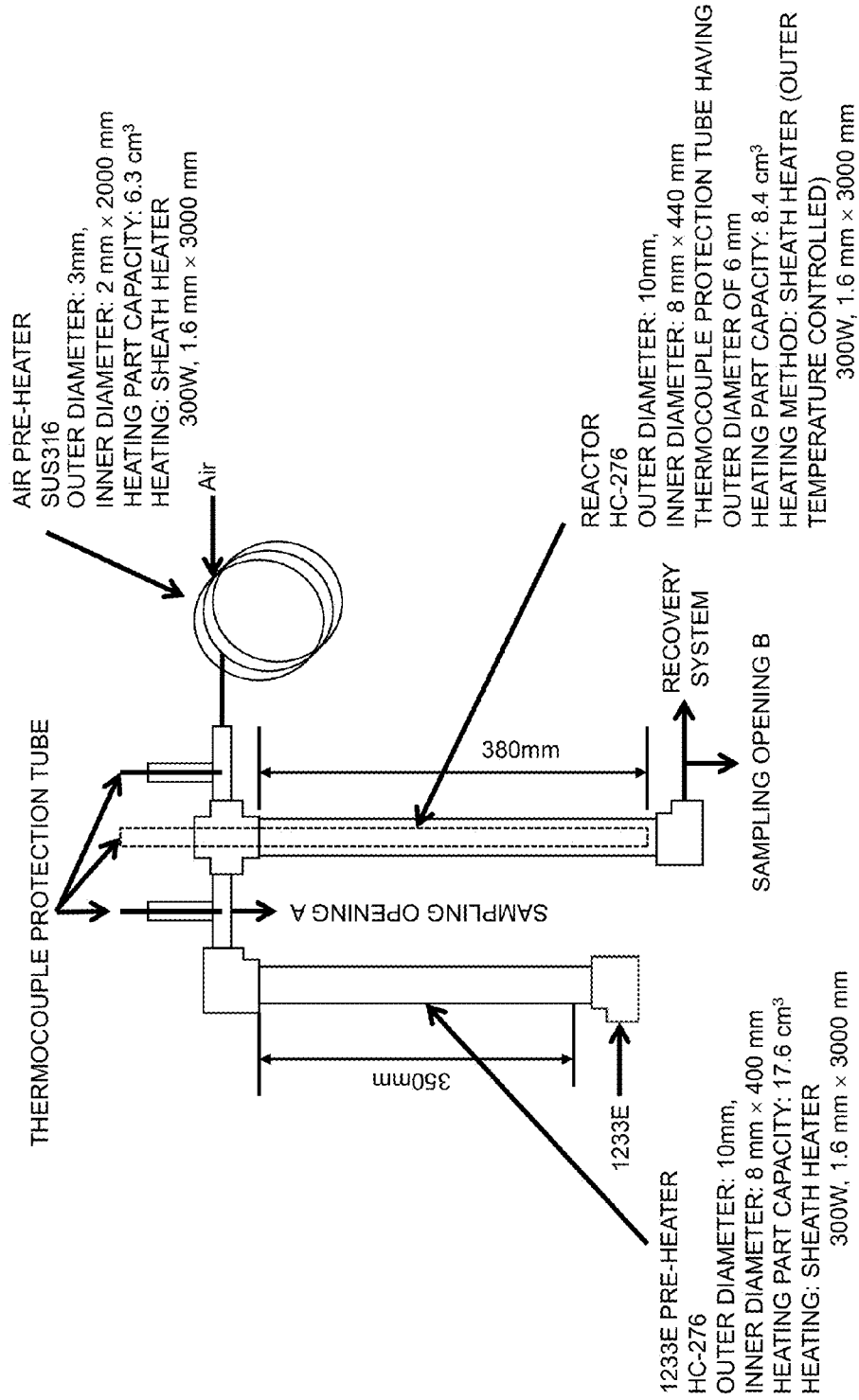
FIG. 5 is a schematic view of a gas phase reaction apparatus used for producing 1-chloro-3,3,3-trifluoro-1-propene.

Only a left part of a device shown in FIG. 5 was actuated to perform an experiment to confirm isomerization of 1233E in a pre-heater. 1233E having a purity of 99.99% (1233Z: 0.00%; other substances: 0.01%) was supplied at a rate of 1.38 g/min., through the pre-heater formed of Hastelloy C276 ™ heated by a 300 W sheath heater and having an outer diameter of 10 mm, an inner diameter of 8 mm and a length of 400 mm. The temperature at an exit of the pre-heater at this point was 355° C. The gas was sampled at a sampling opening A and analyzed. The composition of the gas was as follows: 1233E: 99.88%; 1233Z: 0.04%; and others: 0.08%. It was confirmed that in these conditions, the isomerization of 1233E into 1233Z did not progress.

Comparative Example A-5

Confirmation in the Case where Inert Gas is Used

The entirety of the device shown in FIG. 5 was actuated to perform an experiment using inert gas. In addition to the left part of the device used in comparative example A-4, a right part and a central part of the device were also actuated. The right part is a pre-heater for air or nitrogen. Nitrogen was caused to flow, at a rate 6 cc/min., through a coil formed of SUS316 heated by a 300 W sheath heater and having an outer diameter of 3 mm, an inner diameter of 2 mm and a length of 2000 mm. The temperature of the pre-heater at this point was 359° C. 1233E heated to 353° C. and nitrogen heated to 358° C. were introduced into a reaction tube formed of Hastelloy C276 ™ and having an outer diameter of 10 mm, an inner diameter of 8 mm, a heating part length of 380 mm and a heating part capacity of 8.4 cm$^3$. The reaction tube is provided with thermocouple protection tubes each having an outer diameter of 6 mm. At the time of introduction, the temperature of an entrance (top part) of the reaction tube was 370° C., the temperature of a central part was 421° C., and the temperature of an exit (bottom part) was 389° C. The gas was sampled at a sampling opening B and analyzed. The composition of the gas was as follows: 1233E: 98.72%; 1233Z: 1.04%; and others: 0.24%. It was confirmed that in a system with no radical generating agent, even when the temperature was raised to 420° C., merely about 1% of 1233Z was generated, namely, the isomerization did not progress almost at all. The residence time (contact time) in a central reactor in this experiment was 0.84 seconds.

Example A-6

The same experiment as that in comparative example A-5 was performed except that air was used instead of nitrogen. At this point, the temperature of the entrance (top part) was 370° C., the temperature of the central part was 420° C., and the temperature of the exit (bottom part) was 388° C. The gas was sampled at the sampling opening B and analyzed. The composition of the gas was as follows: 1233E: 88.48%; 1233Z: 11.01%; and others: 0.51%. It has been found that when air as a radical generating agent is added in a catalyst amount, 1233Z is obtained at a yield at least 10 times higher for the comparative example A-5. The residence time (contact time) in the central reactor in this experiment was 0.84 seconds. Since the target compound was obtained at a ratio of 11% by one cycle of operation, this method is understood to be highly efficient. A test piece formed of Hastelloy C and a test piece formed of SUS316 were put into a left reaction tube, and the reaction was continued for 200 hours in total. As a result, with either test piece, the annual corrosion rate was lower than or equal to 0.1 mm/y. The weight and the outer diameter of the thermocouple protection tubes formed of Hastelloy C276 ™ attached to the central reaction tube were measured. As a result, the annual corrosion rate was lower than or equal to 0.1 mm/y. The device used in this reactor has substantially the same collection unit as that of the device shown in FIG. 4 on the stage after the exit.

Comparative Example A-6

Durability Test on SUS316

The same experiment as that in example A-6 was performed for 50 hours except that the thermocouple protection tubes attached to the central reaction tube were formed of SUS316. After the experiment, the protection tubes were corroded, and the surfaces of them were observed to be stripped.

Example A-7

Recycle Experiment

In the experiment in example A-6, 16.1 kg of product was obtained. The product was washed with iced water twice and dried with zeolite to obtain 13.6 kg of dried product (the loss in the mass was mainly of a portion adsorbed to zeolite). The dried product was distilled by a distillation column having 20 theoretical stages to obtain 9.8 kg of 1233E fraction having a purity of 99.41% (content of 1233Z: 0.59%) and 1.1 kg of 1233Z fraction having a purity of 99.9%. Then, the same reaction as that in example A-6 was performed using the 1233E having a purity of 99.41% as a material. At this point, the temperature of the entrance (top part) was 371° C., the temperature of the central part was 421° C., and the temperature of the exit (bottom part) was 389° C. The resultant gas was sampled at the sampling opening B and analyzed. The composition of the gas was as follows: 1233E: 88.03%; 1233Z: 11.23%; and others: 0.31%. It has been confirmed that 1233E is recyclable.

Example A-8

An isomerization reaction of trans-1-chloro-3,3,3-trifluoropropene (1233E) was performed by use of the gas phase reaction device shown in FIG. 4. In a hood, a quartz reaction tube (outer diameter: 8 mm; inner diameter: 6 mm; length: 600 mm) around which two sheath heaters are wound is placed in a vertical manner. The temperatures of the two sheath heaters are independently adjustable. Above the reaction tube, a pressure gauge, a nitrogen inlet, and an organic material inlet are provided. At an exit of the reaction tube, a gas sampling opening is provided. A top heating zone (pre-heating part; set to 250° C.) has a length of 200 mm, and a bottom heating zone (see Table 2 below for the reaction temperature) has a length of 300 mm (capacity of the reaction part: 8.48 ml). At the exit of the reaction tube, a gas washing bottle cooled with ice (content: 10 g of baking soda dissolved in 190 g of ion exchange water), a drying column filled with synthetic zeolite (MS-3A), and a stainless steel trap (formed of SUS) cooled with dry ice-acetone are provided (at an exit of the stainless steel trap, a rubber balloon having a pin hole formed therein is provided). While nitrogen was supplied (300 ml/min.), the top pre-heating part was heated to 250° C. and the bottom reaction part was heated to 450° C. Then, a trans isomer (1233E) having a purity of 99.23% (content of cis isomer (1233Z): 0.09%) was supplied at a supply rate of 1.27 g/min, and chlorine ($Cl_2$) as a radical generating agent was supplied at a supply rate of 4.3 ml/min. One minute later, the supply of nitrogen was stopped. Four hours later, gas was sampled from the gas sampling opening by use of a gas-tight syringe and analyzed. Table 2 shows the results. A visual observation was performed but generation of an oil component was not found.

Examples A-9 and A-10

Substantially the same experiments as that in example A-8 were performed except that the reaction temperature and the organic material supply rate were changed. Table 2 shows the results. A visual observation was performed but generation of an oil component was not found.

Example A-11

The same experiment as that in example A-10 was performed except that quartz reaction tube was replaced with an Ni reaction tube having the same size. Table 2 shows the results. A visual observation was performed but generation of an oil component was not found. No significant difference was found to be caused by the difference in the material of the reaction tube. This suggests that the effect provided by the presence of the radical is larger than the wall effect.

Comparative Examples A-7 Through A-9

In the comparative examples, chlorine was not added. The method of the comparative experiments is substantially the same as that in example A-8, and the detailed reaction conditions and results are shown in Table 2. In the systems with no chlorine, the isomerization did not progress at a practically usable level.

Comparative Example A-10

After the analysis in example A-9 was finished, the supply of only chlorine was stopped. Sixty minutes later, the product composition was checked. As a result, the content of the cis isomer (1233Z) in the product composition was merely 0.16 surface area %. When the experiment conditions were returned to those in example A-9 (when the supply of chlorine was resumed), the content of the cis isomer (1233Z) in the product composition was immediately returned to 13.52%.

Comparative Example A-11

A reaction tube formed of Hastelloy C276 (with no filler) having an outer diameter of 10 mm, an inner diameter of 8 mm and a length of 350 mm was heated by a heater (set temperature: 331° C.). Then, a material (composition: trans isomer (1233E): 99.380%; cis isomer (1233Z): 0.0204%; and others: 0.6716%) was supplied to the reaction tube at a rate of 1.38 g/min. The temperature of the gas at the exit at this point was 358° C. The gas at the exit was analyzed. As a result, the composition of the gas was as follows: trans isomer (1233E): 99.2927%; cis isomer (1233Z): 0.0872%; and others: 0.6201%. In a radical-free system at a temperature lower than 360° C., the content of the cis isomer was merely changed from 0.0204% to 0.0872%. It was confirmed that the isomerization reaction did not substantially progress in the above conditions.

Example A-12

Chlorine gas ($Cl_2$) was supplied at a rate of 2 cc/min to a SUS coil (with no filler) having an outer diameter of 3 mm, an inner diameter of 2 mm and a length of 2000 mm and heated by a heater (applied voltage: 50 V). The temperature of the gas at the exit of the coil was 359° C. Such gas and the gas heated at 358° C. in comparative example A-5 were introduced into a second reaction tube (with no filler) formed of Hastelloy C276, having an outer diameter of 10 mm, an inner diameter of 8 mm and a length of 440 mm, and heated by a heater (set temperature: 372° C.). The inner temperature of the second reaction tube at this point was 361° C. at an entrance, 385° C. in a central part, and 378° C. at an exit. The gas at the exit was analyzed. As a result, the composition of the gas was as follows: trans isomer (1233E): 88.2033%; cis isomer (1233Z): 10.6753%; and others: 1.1214%. It was confirmed

TABLE 2

| | 1233E introduction rate (g/min) | Chlorine introduction rate (ml/min) | Reaction temperature (° C.) | Contact time (s) | Reaction product composition (surface area %) | | |
|---|---|---|---|---|---|---|---|
| | | | | | 1233E | 1233Z | Others |
| Material | | | | | 99.23 | 0.09 | 0.68 |
| Example A-8 | 1.27 | 4.3 | 450 | 0.87 | 83.37 | 14.74 | 1.89 |
| Example A-9 | 1.14 | 3.9 | 400 | 1.12 | 85.32 | 13.45 | 1.23 |
| Example A-10 | 0.75 | 2.6 | 350 | 1.70 | 87.58 | 11.27 | 1.15 |
| Example A-11 | 0.75 | 2.6 | 350 | 1.70 | 87.48 | 11.32 | 1.20 |
| Comparative example A-7 | 1.27 | 0.0 | 450 | 0.88 | 97.81 | 1.13 | 1.06 |
| Comparative example A-8 | 1.13 | 0.0 | 400 | 1.07 | 98.34 | 0.06 | 1.60 |
| Comparative example A-9 | 0.75 | 0.0 | 350 | 1.74 | 98.48 | 0.46 | 1.06 | that when chlorine as a radical generating agent was added, the isomerization progressed conspicuously as indicated by the increase in the content of the cis isomer (1233Z) from 0.0872% to 10.675%.

Example A-13

Substantially the same experiment as that in example A-12 was performed except that air was supplied at a rate of 6 cc/min instead of chlorine and that the second reaction tube having a length of 440 mm was set to have a temperature of 409° C. The temperature of the gas at the exit was 359° C. The inner temperature of the second reaction tube at this point was 371° C. at the entrance, 423° C. in the central part, and 392° C. at the exit. The gas at the exit was analyzed. As a result, the composition of the gas was as follows: trans isomer (1233E): 88.4959%; cis isomer (1233Z): 10.8612%; and others: 0.6429%. It was confirmed that when air as a radical generating agent was added, the isomerization progressed conspicuously as indicated by the increase in the content of the cis isomer (1233Z) from 0.0872% to 10.8612%.

As described above, an isomerization reaction of trans-1-chloro-3,3,3-trifluoro-1-propene (1233E) into cis-1-chloro-3,3,3-trifluoro-1-propene (1233Z), when being provided with a radical generating agent, is progressed to provide a high conversion ratio with no use of a solid catalyst.

For industrially isomerizing trans-1-chloro-3,3,3-trifluoro-1-propene (1233E) into cis-1-chloro-3,3,3-trifluoro-1-propene (1233Z), when the reaction is performed at a high temperature higher than or equal to 600° C., the reaction tube is corroded even when being mainly formed of a corrosion-resistant alloy containing nickel or the like. Thus, even when being thick, the reaction tube needs to be exchanged every year. This disturbs smooth operations. By contrast, the method for producing cis-1-chloro-3,3,3-trifluoro-1-propene according to the present invention that includes isomerizing trans-1-chloro-3,3,3-trifluoro-1-propene (1233E) into cis-1-chloro-3,3,3-trifluoro-1-propene (1233Z) allows the reaction temperature to be decreased by 100° C. to 300° C. as compared with the conventional art by a catalytic action of a radical in the isomerization step. Therefore, the corrosion of the reaction tube can be prevented.

Method for Producing
Cis-1-Chloro-3,3,3-Trifluoro-1-Propene (1233Z)
Including a Catalyst-Free Isomerization Step The isomerization step of trans-1-chloro-3,3,3-trifluoro-1-propene (1233E) included in the method for producing cis-1-chloro-3,3,3-trifluoro-1-propene (1233Z) according to the present invention can be performed in a high temperature range in a catalyst-free condition with no addition of a radical generating agent. Hereinafter, a method for producing cis-1-chloro-3,3,3-trifluoro-1-propene (1233Z) performed in catalyst-free and high-temperature conditions will be described.

Regarding the isomerization reaction of converting 1233E into 1233Z, the knowledge that a high reaction temperature is advantageous for generation of 1233Z from the viewpoint of the thermodynamic equilibrium reaction has been obtained from the calculation results of the temperature dependence of the Boltzmann distributions of 1233E and 1233Z (see FIG. 1). The results are obtained by B3LYP/6–311+G**, which is a non-empirical calculation technique that provides values matching experimental values relatively well. However, at the current state of the art, the Schrodinger's wave equation cannot be solved without an assumption. Namely, this figure shows estimated values based on the assumption. These Boltzmann distributions show equilibrium values merely based the energy levels of 1233E and 1233Z, and are obtained with no consideration of the stability (decomposition, polymerization or side reaction other than EZ isomerization), transition state or activation energy of 1233EZ at the respective temperatures. In the case where a gas phase flow method is used, the reaction time (namely, contact time or residence time) is very short. Therefore, there may be cases where the equilibrium values are not obtained and the experimental value and the calculation result are different from each other. For these reasons, it is reasonable to refer to the calculation results, but the conclusion cannot be made without an actual experiment.

In an isomerization reaction of converting 1233E into 1233Z, when a supported catalyst on which a metal oxide or a metal compound is supported is used and the reaction temperature is in a high temperature range (e.g., higher than or equal to 450° C.), the material may be coked on a surface of the catalyst or turned into tar. In addition, 1233 has a double bond in a molecule and is highly reactive. Therefore, when the reaction temperature is higher than or equal to 450° C., non-preferable impurities such as tar, an oil component or a trifluoropropyne (TFPy) may be produced as a byproduct. Additionally, a high reaction temperature also raises the running cost such as power or the like.

As can be seen, when a contact reaction is to be used, use of a high reaction temperature is advantageous to generate 1233Z, but causes the material to be coked on the surface of the catalyst or turned into tar, which results in production of a byproduct, and also raises the running cost. For these problems regarding productivity, it has been difficult to provide a method for producing highly pure 1233Z in an industrial scale, which is efficient and suitable for equilibrium conditions that are advantageous to generate 1233Z.

According to the present invention, trans-1-chloro-3,3,3-trifluoro-1-propene (1233E), which is a material of cis-1-chloro-3,3,3-trifluoro-1-propene (1233Z), may be a pure trans isomer (1233E) or a mixture (1233EZ) containing a cis isomer (1233Z) and a trans isomer (1233E). A trans isomer (1233E) that is produced by a known method is usable. For example, a mixture of a trans isomer (1233E) and a cis isomer (1233Z) obtained by reacting 1,1,1,3,3-pentachloropropane (240fa) with hydrogen fluoride in a gas phase, or a composition obtained by subjecting the mixture into a known purification process, is usable.

Usually, trans-1-chloro-3,3,3-trifluoro-1-propene obtained by a known production method is a mixture (1233EZ) containing a trans isomer (1233E) and a cis isomer (1233Z). The ratio of 1233E and 1233Z depends on thermodynamic equilibrium. As shown by the calculation example of the Boltzmann distributions in FIG. 1, the equilibrium ratio depends on temperature conditions. The ratio of a trans isomer (1233E) and a cis isomer (1233Z) actually measured tends to be the same as the calculated value, but the absolute value of the measured value may be occasionally different from that of the calculated value. The equilibrium ratio also varies in accordance with the type or shape of the reaction vessel, or the reaction conditions such as the presence/absence of the catalyst and the like.

An isomerization reaction of trans-1-chloro-3,3,3-trifluoro-1-propene (1233E) into cis-1-chloro-3,3,3-trifluoro-1-propene (1233Z) is to cause the equilibrium ratio of 1233E:1233Z to achieve the thermodynamic equilibrium point quickly in a high temperature condition with no addition of a catalyst. Therefore, when a material having a high content of 1233Z is used, the apparent conversion ratio from 1233E into 1233Z is decreased.

As described above, when 1233Z is to be obtained as the target compound, it is ideal to use pure 1233E as a material, but it is acceptable to use 1233EZ containing 1233Z in a material composition. Paying attention to equilibrium, it is more preferable that the content of 1233Z in the material composition is lower. The ratio of 1233E in the material composition is higher than or equal to 50% by weight, preferably higher than or equal to 70% by weight, and more preferably higher than or equal to 90% by weight.

It is more preferable that the mass ratio of 1233Z/1233E in the material is closer to zero. Specifically, the mass ratio of 1233Z/1233E is preferably 0 to 0.2, and more preferably 0 to 0.1. When 1233Z is the target compound, the material is 1233E. Therefore, the content of 1233E cannot be zero.

1233E and 1233Z can be easily separated from each other by distillation because of the difference in the boiling point. Therefore, when a mixture of 1233E and 1233Z is used as a material, it is recommended to first separate 1233Z by distillation so that a material composition having a high content of 1233E is used. It is preferable to distill the mixture of 1233Z and 1233E to separate 1233Z and 1233E from each other so that 1233Z is used as a product and 1233E is used as a material of isomerization.

According to the method for producing cis-1-chloro-3,3,3-trifluoro-1-propene (1233Z) of the present invention, it is reasonable and preferable from the viewpoint of efficient use of the material that a product containing 1233Z obtained by the isomerization of 1233E is collected, 1233E and 1233Z are isolated from each other by distillation or the like, and then unreacted 1233E is reused as a material. Reuse of the unreacted 1233E as a material allows 1233E to be converted into 1233Z efficiently.

As described above, when a reaction is to be caused in a high temperature condition by use of a supported catalyst on which a metal oxide or a metal compound is supported, there is a concern that an unexpected pyrolysis reaction or the like may occur. However, in the reaction conditions provided by the present inventors as a result of active studies, the selectivity of the reaction is very high, and the resultant product does not substantially contain impurities such as 3-chloro-1,1,1,3-tetrafluoropropane (244fa), 2-chloro-1,1,1,3,3-pentafluoropropane (235da) or 1-chloro-1,1,4,4,4-pentafluoro-2-butene (1335) or the like, which is difficult to be separated from the target compound by distillation. Therefore, even when the recycled trans isomer (1233E) is used for a re-reaction, a cis-isomer (1233Z) which can be highly purified is obtained easily. This is a feature of the present invention. Needless to say, an unreacted trans isomer (1233E) may be used for a foaming agent or the like, or may be fluorinated to provide a useful substance such as 1,1,1,3,3-pentafluoropropane (245fa), 1,3,3,3-tetrafluoropropene (1234EZ) or the like.

The isomerization reaction is performed by a gas phase reaction of introducing the second composition, containing trans-1-chloro-3,3,3-trifluoropropene (1233E) as a main component, into a reaction area by use of a reactor. A preferable material for the reactor is a corrosion-resistant material such as carbon, ceramics, stainless steel, nickel, Hastelloy, Monel, Inconel or the like. Nickel, Monel, Hastelloy and Inconel are more preferable. As the reaction system, a batch system or a flow system may be used with no specific limitation. As the reaction system, a common gas phase flow system is preferable. Inert gas such as nitrogen or the like may be used together with the material. The reaction pressure may be high pressure or low pressure with no specific limitation. It is easy to perform the operation at normal pressure or in the vicinity thereof. However, it should be noted that a reaction pressure higher than or equal to 1 MPa is not preferable because such a pressure requires a costly high-pressure-resistant device and also may cause undesirable polymerization of the material or the product. It is sufficient to heat an empty reaction tube to progress the isomerization reaction. When desired, the tube may be provided with a filler such as a static mixer, a Raschig ring or the like. It is preferable that such a filler is formed of a corrosion-resistant material as described above. When alumina or the like is to be used as a filler, it is recommended to bake the filler at, for example, a temperature higher than or equal to 1300° C. to make the filler inert, so that the filler is deprived of catalyst activity. Otherwise, the material may be coked on a surface of the alumina filler or turned into tar. In addition, there is an undesired possibility that a substance difficult to be separated by distillation is unexpectedly produced as a byproduct. When the reaction is continued in such a state, there is a risk that a coke component is deposited on the catalyst to occlude the tube. The specific surface area of the filler is preferably less than or equal to 5 $m^2/g$. When the specific surface area of the filler is larger than this, the filler may exhibit catalyst activity, resulting in, for example, the material being turned into tar, as described above. According to the present invention, the presence of the catalyst is avoided. There is no specific limitation on the method for heating the device (reactor). It is recommended that the device is directly heated by an electric heater or a burner, or indirectly heated by use of melted salt or sand.

The temperature at which the isomerization reaction is to be performed is higher than or equal to 450° C. and lower than or equal to 700° C., preferably higher than or equal to 500° C. and lower than or equal to 700° C., and more preferably higher than or equal to 550° C. and lower than or equal to 650° C. The trans isomer (1233E) is caused to flow through a tube heated to a predetermined temperature and thus is partially isomerized into a cis isomer (1233Z) efficiently. As can be seen from the calculation example of the Boltzmann distributions, the isomerization reaction of 1233E into 1233Z is endothermic. Thus, it is more advantageous that the temperature is higher from a thermodynamic viewpoint. When 1233Z, which is disadvantageous for thermodynamic equilibrium is desired, it is not possible to expect a yield higher than or equal to about 20% in a practically usable temperature range due to the equilibrium. In this case, the reaction product can be separated by distillation into 1233Z, which is the target compound, and unreacted 1233E, so that the separated 1233E can be recovered and reused as a material compound.

According to the Arrhenius equation, as the reaction temperature is higher, the reaction rate is higher. Therefore, naturally, when the temperature is higher, equilibrium is reached more quickly. In the case where a catalyst described as being useful in United States Application Publication No. 2010/0152504 is used, when the reaction is performed at a high temperature higher than or equal to 400° C., the material and the product, which are compounds having a multiple bond, are often polymerized and altered into coke or tar. Especially when the reaction is continued for a long time at a temperature higher than or equal to 400° C., the oil component may be produced as a byproduct to cause wasteful use of the material, the catalyst activity may be reduced by coking, or the tube may be occluded in some cases. It has been found that when the catalyst-free isomerization method according to the present invention is used, generation of tar or coke can be suppressed even at a reaction temperature higher than or equal to 450° C., which is advantageous for generation of 1233Z from viewpoints of equilibrium. In other words, a catalyst-free isomerization reaction is difficult to progress substantially at temperature lower than 400° C., but progresses efficiently in a temperature range of 450° C. to 700° C. However, a reaction temperature higher than 700° C. is not preferable because a substance difficult to be separated from the target compound by distillation may be unexpectedly produced as a byproduct, or TFPy, namely, ($CF_3$—CH≡CH) or ($CF_3$—CH=CH—$CF_3$), which is a non-preferable impurity, is conspicuously produced as a byproduct, and as a result, the amount of oil or tar is increased in certain conditions. In addition, when the reaction temperature is higher than 700° C., a reaction tube formed of a special heat-resistant alloy is needed.

Usually, the reaction time in a gas phase flow system is represented by the contact time. Since no catalyst is used in the present invention, the same concept as that of the contact time is represented by the term "residence time". The residence time is a value (seconds) obtained by dividing the capacity (ml) of the reaction part of the reaction tube by the flow rate (ml/sec) of the gas supplied at the reaction temperature. For example, when only a trans isomer (1233E) is supplied at a rate of 0.59 g/min to a reaction tube (empty tube) that is heated to 500° C. and has an inner capacity of 8.48 ml, the trans isomer (1233E) passes the reaction part at a rate of 0.59/130.5×22400×773/273/60=4.779 (ml/s) with an assumption that the trans isomer (1233E) is ideal gas. Therefore, the residence time is 8.48/4.779≈1.8 (sec).

The residence time is usually longer than or equal to 0.01 seconds and shorter than or equal to 50 seconds, and preferably longer than or equal to 0.1 seconds and shorter than or equal to 10 seconds. In general, when the residence time is shorter than 0.01 seconds, the conversion ratio may be decreased; whereas when the residence time is longer than 50 seconds, the productivity per unit reactor may be decreased, and TFPy ($CF_3$C≡CH) or the like, which is a non-preferable impurity, may be produced as a byproduct, or coking of the material and the product at the wall surface or generation of tar may occur.

Figure 6:
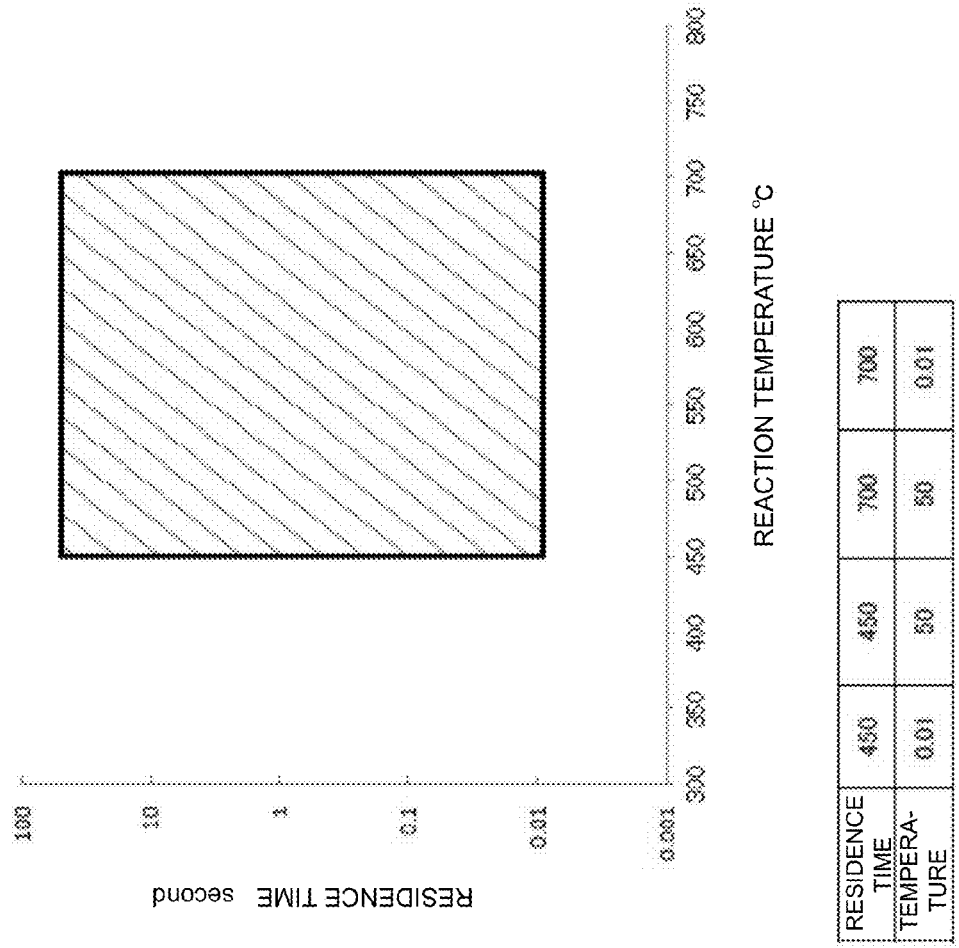
FIG. 6 shows an appropriate combination of reaction temperature and residence time for an isomerization method according to the present invention.

There is an appropriate combination of reaction temperature and residence time according to the present invention. According to specific examples of combinations are, as shown in FIG. 6, the reaction temperature is 450° C. to 700° C. and the residence time is longer than or equal to 0.01 seconds and shorter than or equal to 50 seconds (as shown in the hatched area in FIG. 6 including the outer perimeter). According to a preferable example of combination, as shown in FIG. 8, the reaction temperature is 450° C. to 700° C. and the residence time is longer than or equal to 0.1 seconds and shorter than or equal to 10 seconds (as shown in the hatched area in FIG. 8 including the outer perimeter). In general, even in the case where the reaction temperature is in a preferable range, it is preferable that when the reaction temperature is low, the residence time is longer to provide a higher conversion ratio, whereas when the reaction temperature is high, the residence time is shorter to provide a higher selectivity (the hatched area in FIG. 7 including the outer perimeter).

Figure 7:
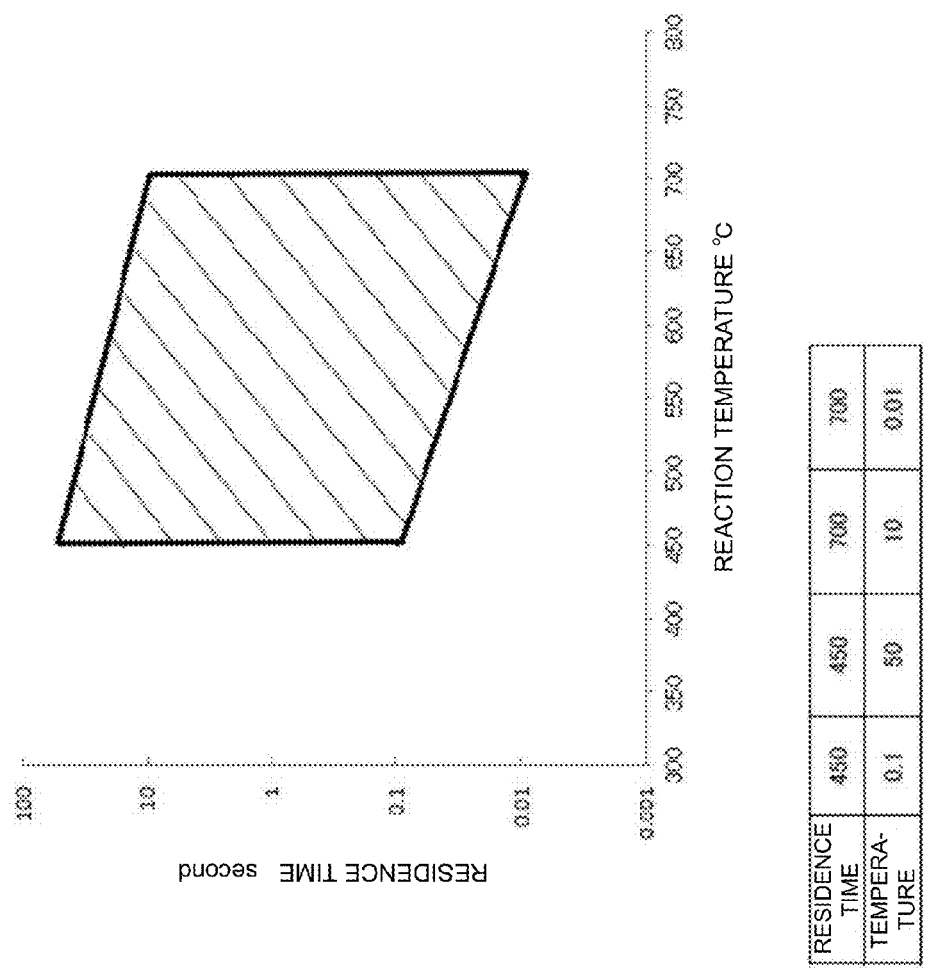
FIG. 7 shows an appropriate combination of reaction temperature and residence time for an isomerization method according to the present invention.
Figure 8:
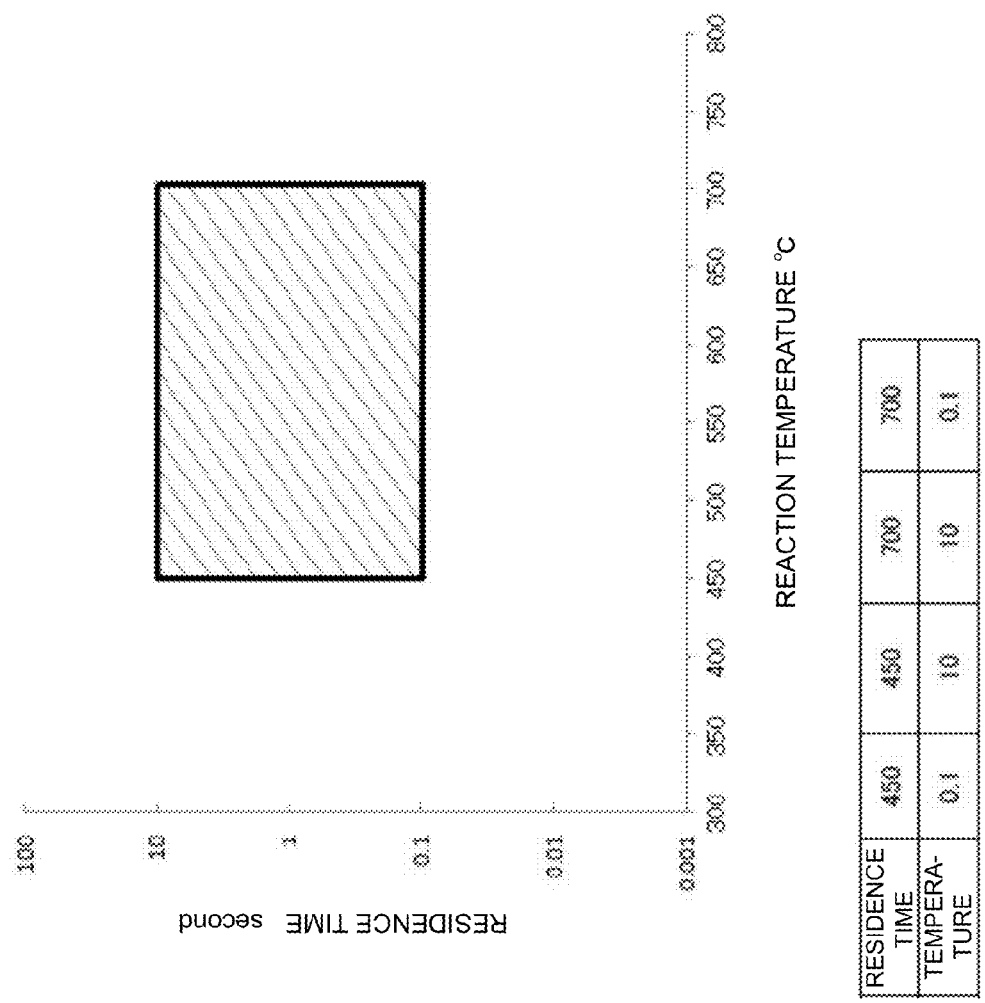
FIG. 8 shows an appropriate combination of reaction temperature and residence time for an isomerization method according to the present invention.

Namely, in each of FIG. 6 through FIG. 8, the hatched area enclosed by the solid line (including the outer perimeter) shows a range which is especially preferable to obtain a practically usable conversion ratio without the material being substantially turned into tar or coked. An area to the left of, or below, the hatched area shows a range in which the material is not much turned into tar or coked but the conversion ratio is insufficient. An area to the right of, or above, the hatched area shows a range in which the conversion ratio is high but the material is turned into tar or coked.

In the case where the operation is performed in a best mode (reaction temperature: 600° C.; residence time: 0.3 seconds) continuously for 24 hours and for 300 days a year, 1800 tons/year of trans isomer (1233E) can be processed with a reactor having a capacity of merely 12 liters. Theoretically, 200 tons/year of purified cis isomer (1233Z) is expected to be produced. This is a highly efficient process as compared with the best mode of the catalyst method performed at 150° C. to 350° C. (United States Patent Application Publication No. 2010/0152504).

Hereinafter, catalyst-free production of cis-1-chloro-3,3,3-trifluoropropene (1233Z) according to the present invention will be specifically described by way of examples. However, the present invention is not limited to the following examples. Herein, "%" used for a composition analysis value represents the "GC surface area %" of a composition of a reaction mixture measured by use of gas chromatography (detector: FID). Each displayed value is obtained by rounding off the numeral at the place smaller by one digit than the smallest place of the displayed value. For example, 0.00% represents a value smaller than 0.005 GC surface area %. In Table 3, the results of examples B-1 to B-14, B-17 and B-19 and comparative examples B-1 and B-2 are obtained by performing a GLC analysis on a gas sample by use of a gas-tight syringe. The results of examples B-15, B-16 and B-19 and comparative example 6 are obtained by performing a GLC analysis on a liquid sample by use of a microsyringe cooled to –5° C.

An organic substance containing a trans isomer (1233E) as a material was prepared by the following method (substantially the same as the method in example 2 of Japanese Patent No. 3031465 (Japanese Laid-Open Patent Publication No. 2000-7592)).

[Example of Catalyst Preparation, Activated Carbon]

0.2 liters of granular palm shell carbon having a surface area of 1200 m²/g and a pore diameter of 18 angstroms (granular Shirosagi G2X, 4 to 6 mesh; produced by Takeda Pharmaceutical Company Limited) was put into a 1-liter glass flask, warmed to a temperature of 130 to 150° C., and then deprived of moisture by a vacuum pump. At the time when extraction of moisture was recognized to stop, nitrogen was introduced into the flask to provide normal pressure.

[Example of Preparing a Material]

100 ml of activated carbon shown in example of catalyst preparation and 0.3 mol (50.4 g) of 1,1,2,2-tetrachloroethane were put into a 1-liter autoclave formed of SUS316L and including a reflux cooling device and a stirrer, and were kept at a temperature of 180° C. while being stirred. Then, hydrogen fluoride was supplied at the rate of 0.75 g/min and 1,1,1,3,3-pentachloropropane was supplied at the rate of 0.42 g/min to the reactor. The pressure in the system, which would have been raised by generation of hydrogen chloride along with the progress of the reaction, was kept at 1 MPa by a back-pressure valve provided in a downstream part of the reactor. The reaction was stabilized 3 hours after the start of the reaction. Therefore, the generated gas flowing out of the reactor was blown into water to remove acid gas, and then an organic substance was collected by a dry ice-acetone-trap.

The organic substance obtained by the above-described method was washed with iced water, de-watered by using molecular sieves 4A, and then distilled at normal pressure in order to remove impurities such as 3-chloro-1,1,1,3-tetrafluoropropane (244fa) and the like. Thus, a fraction of 18° C. to 19° C. was obtained as the material composition (the composition is shown in Table 3). By being analyzed, the residue in the distillation column was confirmed to contain a cis isomer (1233Z) as a main component and also 3-chloro-1,1,1,3-tetrafluoropropane (244fa), 2-chloro-1,1,1,3,3-pentafluoropropane (235da), and 1-chloro-1,1,4,4,4-pentafluoro-2-butene (1335). In the isomerization step of the experiment performed after this, the trans isomer (1233E) obtained in the fluorination reaction step and the distillation step described above, having a purity of 99.19%, and not containing impurities such as 3-chloro-1,1,1,3-tetrafluoropropane (244fa), 2-chloro-1,1,1,3,3-pentafluoropropane (235da), 1-chloro-1,1,4,4,4-pentafluoro-2-butene (1335) and the like was used.

Example B-1

As shown in FIG. 4, in a hood, a reaction tube with no filler (outer diameter: 8 mm; inner diameter: 6 mm; length: 600 mm) around which two sheath heaters are wound is placed in a vertical manner. The temperatures of the two sheath heaters are independently adjustable. Above the reaction tube, a pressure gauge, a nitrogen inlet, and an organic material inlet are provided. At an exit of the reaction tube, a gas sampling opening is provided. A top heating zone (pre-heating part; set to 250° C.) has a length of 200 mm, and a bottom heating zone (see Table 3 for the reaction temperature) has a length of 300 mm (capacity of the reaction part: 8.48 ml). On a stage after the exit of the reaction tube, a gas washing bottle cooled with ice (content: 10 g of baking soda dissolved in 190 g of ion exchange water), a drying column filled with synthetic zeolite (MS-3A), and a stainless steel trap (formed of SUS) cooled with dry ice-acetone are provided in this order (at the exit of the stainless steel trap, a rubber balloon having a pin hole formed therein is provided). While nitrogen was supplied (300 ml/min.), the top pre-heating part was heated to 250° C. and the bottom reaction part was heated to 500° C. Then, a trans isomer (1233E) having a purity of 99.19% was supplied at a supply rate of 0.6 g/min. One minute later, the supply of nitrogen was stopped. Four hours later, gas was sampled from the gas sampling opening by use of a gas-tight syringe and analyzed. Table 3 shows the results. A visual observation was performed but generation of an oil component was not found.

Examples B-2 to B-13

Substantially the same experiments as that in example B-1 were performed except that the reaction temperature and the organic material supply rate (residence time) were changed. Table 3 shows the results. A visual observation was performed but generation of an oil component was not found.

Example B-14

Substantially the same experiment as that in example B-13 was performed except that nitrogen was supplied at a rate of 100 ml/min together with the material. Table 3 shows the results. Referring to the results, the production, as a byproduct, of a substance having a low boiling point such as TFPy ($CF_3$—CH=CH) or the like was suppressed by supplying nitrogen.

Comparative Examples B-1 to B-3

Substantially the same experiments as that in example B-1 were performed except that the reaction temperature and the organic material supply rate (residence time) were changed. Table 3 shows the results. In comparative examples B-1 and B-2, although generation of oil was not found, the conversion ratio did not reach a practically usable level. In comparative example B-3, generation of a large amount of oil was found (gas chromatography analysis was not performed because the gas sampling opening was stained with oil).

Comparative Example B-4

γ-alumina beads were pulverized, and the reaction tube was filled with the granules thereof having a diameter of about 0.5 mm to 1.5 mm in an amount of 8.5 ml. Then, substantially the same experiment as that in example B-1 was performed in the conditions shown in Table 3. After generation of oil was found, the reaction tube was occluded. Thus, the experiment was discontinued.

Comparative Example B-5

The same experiment as that in comparative example B-4 was performed except that $AlF_3$ pellet was used. Like in comparative example B-4, after generation of oil was found, the reaction tube was occluded. Thus, the experiment was discontinued.

Example B-15

In order to find the material balance, after the product in example B-10 was sampled, the reaction continued in the same conditions with the gas washing bottle (content: ion exchange water (200 ml)) and the SUS trap being replaced. After 124.59 g was fed (about 85 minutes later), both of the liquid in the gas washing bottle and the liquid in the SUS trap were put into a separating funnel, cooled in a refrigerator beforehand, for separation. As a result, 124.33 g of organic substance was recovered (organic substance recovery ratio: 99.8%; composition: TFPy: 0.04%, 1234E: 0.43%, 1336: 0.00%, 245fa: 0.09%, 1234Z: 0.17%, trans isomer (1233E): 82.81%, cis isomer (1233Z): 15.82%, others: 0.64%). As a result of a neutralization titration with sodium hydroxide and a silver nitrate titration performed on an upper water phase, it was found that the content of hydrochloric acid in the organic substance was 0.002 wt. % and that the content of hydrogen fluoride was 0.05 wt. %. Based on the above, it was shown that generation oil or coking did not substantially occur in the above conditions.

Example B-16

Substantially the same experiment as that in example B-8 was performed for 12 hours except that a SUS gas washing bottle (3000 ml) containing 5% by mass of aqueous solution of baking soda (500 ml) was used. The liquid in the gas washing bottle and the liquid in the trap were combined and separated. As a result, 2092.5 g of organic substance was obtained. 5% by mass of aqueous solution of baking soda in an amount of 102 g was added the obtained organic substance, and the resultant substance was washed and separated. As a result, 2047.7 g of organic substance was obtained. 101 g of ion exchange water was added thereto, and the resultant substance was washed and separated. As a result, 2012.1 g of organic substance was obtained (the water phase at this point had a pH value of 8). 105 g of ion exchange water was added to the organic phase thereof, and the resultant substance was washed and separated in substantially the same manner. As a result, 1979.1 g of organic substance was obtained (the water phase at this point had a pH value of 7). 50 g of synthetic zeolite (MS-3A) was added to the organic substance, and the substance was stored in a refrigerator overnight and filtrated. As a result, 1910.1 g of sample containing 8 ppm of moisture was obtained. The sample was distilled by a distillation column having 35 theoretical stages. Table 4 shows the results. The liquid organic substance was analyzed by GC (gas chromatography) by use of a microsyringe cooled to −5° C. In fraction 8, a highly pure cis isomer (1233Z) having 99.94 surface area % was obtained. In this fraction, neither 3-chloro-1,1,1,3-tetrafluoropropane (244fa) nor 2-chloro-1,1,3,3-pentafluoropropane (235da) was detected.

Example B-17

Substantially the same experiment as that in example B-8 was performed using a blend of fractions 2 through 6 obtained by the distillation in example B-16 as a recycled material (trans isomer (1233E); purity: 99.61%). Table 3 shows the results. The same results were obtained even with such a recycled material.

Example B-18

Use

Washing Detergent

A highly pure cis isomer (1233Z) having a purity of 99.94 surface area obtained in example B-16 was put into a compact ultrasonic washing device, and a glass lens with fingerprints was washed for 30 seconds using the device. After the washing, the glass lens was dried by a drier and visually observed. As a result, the fingerprints were completely removed, and generation of stain was not found.

Example B-19

Use

Cooling Composition for Solar Cell 20 g of sample obtained in example B-16 was put into a pressure-resistant glass container, and the glass container was plugged tightly. An experiment of exposing the glass container to sunlight was performed for 37 days from Oct. 14, 2011 (location: Kawagoe-shi, Saitama-ken). Table 5 shows the results of a GLC analysis performed on the sample before and after the experiment. When the cis isomer (1233Z) not substantially containing 3-chloro-1,1,1,3-tetrafluoropropane (244fa) that was obtained by the present invention was used, no substantial composition change was found. By contrast, when a cis isomer (1233Z) containing 3-chloro-1,1,1,3-tetrafluoropropane (244fa) that was obtained by an extractive distillation method as in comparative example B-6 was used, the composition was found to be conspicuously changed.

Comparative Example B-6

The same experiment as that in example B-19 was performed except that a sample obtained by being subjected to extractive distillation by the method described in Japanese Patent Laid-Open No. 2010-202640—and then subjected to precision distillation was used. Table 5 shows the results.

TABLE 3

|  | Reaction temperature °C. | Organic substance supply rate g/min | Residence time (at reaction temperature) second | Conversion rate % |
|---|---|---|---|---|
| Material composition |  |  |  |  |
| Example B-1 | 500 | 0.60 | 1.8 | 8.5 |
| Example B-2 | 550 | 0.56 | 1.8 | 15.2 |
| Example B-3 | 600 | 0.52 | 1.8 | 25.4 |
| Example B-4 | 600 | 1.68 | 0.6 | 20.8 |
| Example B-5 | 600 | 0.56 | 1.7 | 19.6 |
| Example B-6 | 600 | 0.65 | 1.4 | 19.6 |
| Example B-7 | 600 | 4.47 | 0.2 | 12.8 |
| Example B-8 | 600 | 2.93 | 0.3 | 16.9 |
| Example B-9 | 600 | 1.32 | 0.7 | 19.4 |
| Example B-10 | 600 | 1.48 | 0.6 | 16.5 |
| Example B-11 | 600 | 1.96 | 0.6 | 14.0 |
| Example B-12 | 650 | 0.60 | 1.6 | 24.1 |
| Example B-13 | 650 | 0.59 | 1.6 | 24.1 |
| Example B-14 | 650 | 0.59 | 0.8 | 23.5 |
| Example B-15 | 600 | 1.48 | 0.6 | 16.4 |
| Example B-17 | 600 | 2.93 | 0.3 | 83.7 |
| Comparative example B-1 | 250 | 0.02 | 77.4 | 0.1 |
| Comparative example B-2 | 400 | 0.06 | 20.0 | 4.4 |
| Comparative example B-3 | 750 | 0.06 | 13.2 | — |
| Comparative example B-4 | 500 | 0.56 | 1.9 | — |
| Comparative example B-5 | 500 | 0.56 | 1.9 | — |

|  | Gas composition (surface area %) |  |  |  |  |  |  |  | Analysis |  |
|---|---|---|---|---|---|---|---|---|---|---|
|  | TFPy | 1234E | 1336 | 245fa | 1234Z | 1233E | 1233Z | Others | method | Remarks |
| Material composition | 0.00 | 0.59 | 0.00 | 0.09 | 0.09 | 99.19 | 0.01 | 0.02 |  |  |
| Example B-1 | 0.00 | 0.50 | 0.00 | 0.09 | 0.12 | 90.07 | 8.44 | 0.15 | Gas |  |
| Example B-2 | 0.02 | 0.50 | 0.00 | 0.09 | 0.13 | 83.98 | 14.90 | 0.37 | Gas |  |
| Example B-3 | 1.52 | 0.56 | 3.49 | 0.03 | 0.22 | 78.81 | 16.29 | 4.05 | Gas |  |
| Example B-4 | 0.24 | 0.54 | 0.32 | 0.08 | 0.18 | 78.40 | 18.37 | 1.86 | Gas |  |
| Example B-5 | 0.25 | 0.61 | 0.27 | 0.08 | 0.19 | 79.61 | 17.89 | 1.09 | Gas |  |
| Example B-6 | 0.10 | 0.55 | 0.00 | 0.09 | 0.14 | 79.70 | 18.43 | 0.97 | Gas |  |

TABLE 3-continued

| | | | | | | | | | |
|---|---|---|---|---|---|---|---|---|---|
| Example B-7 | 0.05 | 0.62 | 0.00 | 0.09 | 0.16 | 86.40 | 11.52 | 1.15 | Gas |
| Example B-8 | 0.08 | 0.66 | 0.00 | 0.09 | 0.17 | 82.29 | 15.36 | 1.36 | Gas |
| Example B-9 | 0.07 | 0.65 | 0.00 | 0.09 | 0.17 | 79.79 | 18.22 | 1.00 | Gas |
| Example B-10 | 0.04 | 0.64 | 0.00 | 0.09 | 0.17 | 82.73 | 15.81 | 0.52 | Gas |
| Example B-11 | 0.02 | 0.64 | 0.00 | 0.10 | 0.16 | 85.24 | 13.52 | 0.33 | Gas |
| Example B-12 | 1.12 | 0.44 | 2.22 | 0.05 | 0.17 | 75.06 | 18.87 | 2.09 | Gas |
| Example B-13 | 2.20 | 0.05 | 0.17 | 0.11 | 0.25 | 75.06 | 18.87 | 3.31 | Gas |
| Example B-14 | 0.40 | 0.07 | 0.13 | 0.03 | 0.04 | 75.69 | 19.52 | 4.11 | Gas $N_2$ (100 cc/min) also supplied |
| Example B-15 | 0.04 | 0.43 | 0.00 | 0.09 | 0.17 | 82.81 | 15.82 | 0.84 | Liquid Composition of recovered organic substance (124.33 g) |
| Example B-17 | 0.07 | 0.18 | 0.00 | 0.02 | 0.13 | 82.86 | 15.46 | 1.28 | Gas |
| Comparative example B-1 | 0.00 | 0.58 | 0.00 | 0.09 | 0.09 | 99.09 | 0.01 | 0.14 | Gas |
| Comparative example B-2 | 0.13 | 0.97 | 0.00 | 0.06 | 0.21 | 94.80 | 2.76 | 1.08 | Gas |
| Comparative example B-3 | Oil generated | | | | | | | Analysis impossible | |
| Comparative example B-4 | Oil generated and then the tube occluded | | | | | | | Analysis impossible | $Al_2C_3$ catalyst |
| Comparative example B-5 | Oil generated and then the tube occluded | | | | | | | Analysis impossible | $AlF_3$ catalyst |

TABLE 4

| | | Composition (surface area %) | | | | | | |
|---|---|---|---|---|---|---|---|---|
| Fraction | Mass (g) | TFPy | 1234E | 245fa | 1234Z | 1233E | 1233Z | Others |
| Before distillation (put into the column) | 1904.66 | 0.013 | 0.390 | 0.082 | 0.128 | 83.464 | 15.286 | 0.637 |
| Trap | 2.02 | 1.058 | 8.334 | 0.243 | 0.656 | 83.964 | 5.551 | 0.194 |
| Fraction 1 | 263.23 | 0.028 | 3.417 | 0.685 | 1.240 | 94.531 | 0.003 | 0.095 |
| Fraction 2 | 296.46 | 0.001 | 0.008 | 0.071 | 0.062 | 99.808 | 0.000 | 0.050 |
| Fraction 3 | 221.97 | 0.000 | 0.001 | 0.021 | 0.011 | 99.937 | 0.000 | 0.031 |
| Fraction 4 | 295.57 | 0.046 | 0.790 | 0.014 | 0.028 | 99.090 | 0.000 | 0.032 |
| Fraction 5 | 320.30 | 0.002 | 0.004 | 0.001 | 0.001 | 99.976 | 0.000 | 0.016 |
| Fraction 6 | 219.43 | 0.000 | 0.001 | 0.000 | 0.000 | 99.155 | 0.829 | 0.015 |
| Fraction 7 | 20.55 | 0.000 | 0.002 | 0.000 | 0.001 | 4.013 | 95.914 | 0.071 |
| Fraction 8 | 198.95 | 0.000 | 0.000 | 0.000 | 0.000 | 0.054 | 99.940 | 0.006 |
| Residue in the column | 62.21 | 0.000 | 0.198 | 0.005 | 0.016 | 1.538 | 77.145 | 21.099 |
| Total amount recovered | 1900.69 | | | | | | | |

TABLE 5

| | | Composition found by gas chromatography (surface area %) | | | |
|---|---|---|---|---|---|
| | Sunlight | 1233Z | 1233E | 244fa | Others |
| Example B-19 (Sample obtained in example B-6) | Before exposure | 99.94 | 0.00 | 0.00 | 0.06 |
| | After exposure | 99.94 | 0.00 | 0.00 | 0.06 |
| Comparative example B-6 (Sample obtained by extractive distillation) | Before exposure | 99.55 | 0.00 | 0.34 | 0.11 |
| | After exposure | 94.82 | 4.73 | 0.34 | 0.11 |

As described above, it is understood that the isomerization reaction of trans-1-chloro-3,3,3-trifluoro-1-propene (1233E) into cis-1-chloro-3,3,3-trifluoro-1-propene (1233Z) is progressed, with addition of neither a radical generating agent nor a catalyst, in a high temperature condition, and a high conversion ratio is provided.

The highly pure cis isomer (1233Z) obtained by the present invention is optimal as a washing detergent, and is superb for removing fingerprints, cutting oil, silicone, machine oil, particles and the like (see example B-18). Since the cis isomer obtained by the present invention does not contain impurities, there is no concern of polymer attack or the like caused by the impurity components. In the case where the cis isomer obtained by the present invention is used as a material of TFPy or the like, a highly pure target compound can be produced. Highly pure 1233Z having a purity higher than or equal to 99.9% is highly stable as compared with 1233Z obtained by a conventional method (e.g., 1233Z obtained by the extractive distillation method described in Japanese Patent Laid-Open No. 2010-202640) (see example B-19). The highly pure cis isomer (1233Z) obtained by the present invention is highly preferable for a working fluid in a heat pump, a heat pipe or the like or for a solar cell coolant, each of which is required to be highly stable.

Method for producing
trans-1-chloro-3,3,3-trifluoro-1-propene (1233E)

Cis-1-chloro-3,3,3-trifluoro-1-propene (1233Z), which is a material of trans-1-chloro-3,3,3-trifluoro-1-propene (1233E), may be a pure cis isomer (1233Z) or a mixture containing a cis isomer (1233Z) and a trans isomer (1233E). A cis isomer (1233Z) that is produced by a known method is usable. For example, a mixture of a trans isomer (1233E) and a cis isomer (1233Z) obtained by reacting 1,1,1,3,3-pentachloropropane (240fa) with hydrogen fluoride in a gas phase, or a composition obtained by purifying the mixture using a known purification process, is usable.

A mixture of 1233E and 1233Z that is obtained by reacting 1,1,1,3,3-pentachloropropane (240fa) with hydrogen fluoride may occasionally contain 3-chloro-1,1,1,3-tetrafluoropropane (244fa) and/or 2-chloro-1,1,1,3,3-pentafluoropropane (235da), each of which is usually difficult to be separated by distillation from 1233Z. However, the isomerization of the present invention can be performed with no need to separate 244fa or 235da, which is difficult to be separated by distillation, from 1233Z. This is an advantage of the present invention. Additionally, there is no problem even when a byproduct derived from the production of a material to be used is contained in the present invention.

Usually, cis-1-chloro-3,3,3-trifluoro-1-propene obtained by a known production method is a mixture containing a trans isomer (1233E) and a cis isomer (1233Z). The ratio of 1233E and 1233Z in the mixture depends on thermodynamic equilibrium. As shown by the calculation example of the Boltzmann distributions in FIG. 1, the equilibrium ratio depends on temperature conditions.

An isomerization reaction of cis-1-chloro-3,3,3-trifluoro-1-propene (1233Z) into trans-1-chloro-3,3,3-trifluoro-1-propene (1233E) is to cause the equilibrium ratio of 1233E:1233Z to achieve the thermodynamic equilibrium point quickly by a catalytic action of a radical. When the isomer ratio of 1233Z:1233E (1233Z/1233E) is higher than the equilibrium ratio, at least a part of 1233Z is converted into 1233E. The ratio of 1233E/1233Z depends on thermodynamic equilibrium. Therefore, when a material having a high content of 1233E is used, the apparent conversion ratio from 1233Z into 1233E is decreased. For this reason, it is desirable to use a material having a high content of 1233Z.

When 1233E is to be obtained as the target compound, it is ideal to use pure 1233Z as a material, but it is acceptable to use 1233EZ containing 1233E in a material composition. Paying attention to equilibrium, it is more preferable that the content of 1233E in the material composition is lower. The ratio of 1233Z in the material composition is higher than or equal to 50% by weight, preferably higher than or equal to 70% by weight, and more preferably higher than or equal to 90% by weight. It is more preferable that the mass ratio of 1233E/1233Z in the material is closer to zero. Specifically, the mass ratio of 1233E/1233Z is preferably 0 to 0.2, and more preferably 0 to 0.1. When 1233E is the target compound, the material is 1233Z. Therefore, the content of 1233Z cannot be zero.

1233E and 1233Z can be easily separated from each other by distillation because of the difference in the boiling point. Therefore, when a mixture of 1233E and 1233Z is used as a material, it is recommended to first separate 1233E by distillation so that a material composition having a high content of 1233Z is used. It is preferable to distill the mixture of 1233Z and 1233E to separate 1233Z and 1233E from each other so that 1233E is used as a product and 1233Z is used as a material used for the isomerization reaction.

It is reasonable and preferable from the viewpoint of efficient use of the material that a product containing 1233E obtained by the isomerization of the present invention is collected, 1233E and 1233Z in the product are isolated from each other by distillation or the like, and then unreacted 1233Z is reused as a material. Reuse of the unreacted 1233Z as a material allows 1233Z to be converted into 1233E efficiently.

In an isomerization step of 1233Z into 1233E, a radical is generated in a reaction system in a predetermined temperature range. This progresses an isomerization reaction of converting 1233Z into 1233E. According to a preferable method for generating a radical in a system, a radical generating agent is added to the system as described above. A radical generating agent may be at least one selected from halogen gas such as chlorine, bromine and the like; oxygen-containing gas such as air, oxygen, ozone, hydrogen peroxide, nitrogen oxide and the like; and carbon halide. An especially preferable radical generating agent is air or oxygen. The details of the carbon halide is described above and will not be described here. Examples of carbon halide, which is usable as a radial generating agent, do not include 1-chloro-3,3,3-trifluoro-1-propene (1233), which is a material of the present invention.

According to a method for putting a radical into contact with a material composition containing 1233Z by a gas phase reaction, a radical generating agent may be provided with light or heat to be activated beforehand and then introduced into a reaction tube, or a mixture of a radical generating agent and a material composition containing 1233Z may be introduced into a reaction tube and then activated with light or heat. For putting a radical into contact with 1233Z efficiently, it is preferable to supply a radical generating agent and a material composition containing 1233Z to a reaction tube at the same time in the form of a mixture. When a material composition containing 1233Z is to be supplied, inert gas such as nitrogen or the like may be supplied, together with the material composition, in an amount that is sufficiently small so as not to decrease the productivity. From an industrial viewpoint, it is simple and preferable that a mixture of a radical generating agent and a material composition containing 1233Z is put into a heated reaction tube and is provided with thermal energy in the reaction tube to generate a thermal radical.

Specifically, according to a preferable method for producing 1233E as the target compound, a mixture containing cis-1-chloro-3,3,3-trifluoropropene (1233Z) and at least one radical generating agent selected from the group consisting of chlorine, oxygen, bromine, air, hydrogen peroxide, ozone, nitrogen oxide, and carbon halide is heated to isomerize cis-1-chloro-3,3,3-trifluoropropene (1233Z) into trans-1-chloro-3,3,3-trifluoropropene (1233E) by an isomerization reaction caused in the presence of a radical. The isomerization reaction caused in the presence of the radical converts at least a part of cis-1-chloro-3,3,3-trifluoropropene (1233Z) into trans-1-chloro-3,3,3-trifluoropropene (1233E), so that the ratio of the trans-1-chloro-3,3,3-trifluoropropene (1233E) with respect to the cis-1-chloro-3,3,3-trifluoropropene (1233Z) can be increased.

It is preferable that a radical generating agent is supplied in a trace amount. Addition of an excessive amount of radical generating agent is a waste of the sub material and also imposes, after the reaction, a load on a step of separating the radical generating agent from 1233. Even when air, which is relatively easily separable, is added in a large amount, the capability of a condensation step or a distillation step is lowered. When an excessive amount of chlorine as a radical generating agent is added, a compound containing chlorine added to the double bond is produced as a byproduct as described above. Especially, a compound containing chlorine added to 1233 is HCFC, which causes global warming or depletion of ozone layer. Therefore, it is more preferable that the amount of a byproduct containing chlorine is smaller.

The present inventors performed an experiment with the ratio of the radical generating agent to the material composition being varied. As a result, even when the amount of chlorine was decreased down to the lower limit of measurement of the chlorine flowmeter, no substantial influence was found on the conversion ratio from 1233Z into 1233E. From this, it has been found that the amount of the radical generating agent may be an extremely trace amount (experimental results will be described later). It should be noted that, as described above, the optimal amount of the radical generating agent depends on the type of the radical generating agent or the structure of the reaction tube. When a reaction tube highly suitable for the mixing is used, a desired conversion ratio is achieved even with a trace amount of radical generating agent. In other cases, the amount of the radical generating agent to be added may be increased to raise the concentration of the radical, so that the conversion ratio is increased.

Specifically, the amount of the radical generating agent depends on the type of the radical generating agent or the shape of the reaction tube. However, usually, the amount of the radical generating agent with respect to 1233Z, which is the material, is preferably higher than or equal to 0.0001 mol % and lower than or equal to 10 mol %, and more preferably higher than or equal to 0.0001 mol % and lower than or equal to 0.005 mol %. When a reaction tube highly suitable for putting the radical into contact with 1233Z is used, 1233Z and the radical can collide against each other sufficiently. Therefore, the amount of the radical generating agent with respect to 1233Z is preferably higher than or equal to 0.0001 mol % and lower than or equal to 0.005 mol %.

A reaction tube highly suitable for putting the radical into contact with 1233Z has, for example, a filler that is inactive to the reaction, such as a static mixer, a Raschig ring, a Pall ring, a metal mesh or the like, packed therein. According to the present invention, a filler may be packed in the reaction tube, needless to say. The reaction tube or the like is formed of a material substantially the same as that of the reaction tube described above regarding the isomerization reaction of trans-1-chloro-3,3,3-trifluoro-1-propene (1233E) into cis-1-chloro-3,3,3-trifluoro-1-propene (1233Z). For an industrial device, a reaction tube having a high length/inner diameter ratio allows the radical and 1233Z to be put into contact with each other efficiently even when being empty with no filler as described above and also has high heat conductivity, and thus is especially preferable. Specifically, the length/inner diameter ratio of the reaction tube is higher than or equal to 10 and lower than or equal to 1000, and preferably higher than or equal to 20 and lower than or equal to 500. When the length/inner diameter ratio is lower than 10, the radical and 1233Z may not be put into sufficient contact with each other; and when the length/inner diameter ratio is higher than 1000, the device cost may be raised, or the pressure loss may be too large in certain operation conditions. It is usually preferable that the inner diameter of the reaction tube is in the range of 8 mm to 150 mm, and that the length of the reaction tube is in the range of 1 m to 200 m. It is especially preferable that the inner diameter of the reaction tube is in the range of 10 mm to 60 mm, and that the length of the reaction tube is in the range of 2 m to 50 m. Especially preferably, the reaction tube is empty. There is no specific limitation on the shape of the reaction tube. The reaction tube may be straight, coiled, or folded by use of a joint or the like. The above-described preferable shapes of the reaction tube are for industrial mass production. In the case of small-scale laboratory-type production, any reaction tube is usable. When desired, a static mixer may be used, or the reaction tube may be provided with a filler such as a Raschig ring, a Pall ring or the like. In the case where the reaction device is to be heated, there is no specific limitation on the heating method. The reaction device may be directly heated by an electric heater or a burner, or may be indirectly heated by use of melted salt or sand.

As described above, the generation of a radical occurs in a chain-reacting manner. Therefore, at a reaction temperature at which the radical generating agent can generate a radical, even though rebinding occurs, recleavage occurs. Thus, an isomerization reaction of 1233Z is promoted even with a trace amount of the radical generating agent. Namely, in a method for producing 1-chloro-3,3,3-trifluoropropene including a cis (1233Z)-trans (1233E) isomerization step of 1-chloro-3,3,3-trifluoropropene (1233), the isomerization reaction progresses even when a trace amount of catalyst is added. It is more preferable that the amount of an additive, which is a sub material, is smaller.

In a method for producing trans-1-chloro-3,3,3-trifluoropropene (1233E) according to the present invention, a solid catalyst is not indispensable. However, a solid catalyst may be used in order to quickly progress the isomerization reaction in the presence of a radical. The solid catalysts described above regarding the method for producing cis-1-chloro-3,3,3-trifluoro-1-propene (1233Z) are preferably usable.

Like in the method for producing cis-1-chloro-3,3,3-trifluoro-1-propene (1233Z), in a method for producing trans-1-chloro-3,3,3-trifluoropropene (1233E) according to the present invention, it is preferable to perform the isomerization reaction by use of an empty column reactor with no catalyst, filler or the like, so that the efficiency of the isomerization reaction in the presence of a radical is not decreased. It is especially preferable to perform the isomerization reaction in an empty column of a gas phase flow system (see the examples described below).

When a solid catalyst is added, there may be a non-preferable case where the radical generating agent and 1233Z cause an unexpected reaction that is not an isomerization reaction, and 1233Z as a reaction material is merely converted into a non-preferable byproduct and the radical generating agent is consumed for the reaction with 1233Z.

As shown above by the calculation example of the Boltzmann distributions (see FIG. 1), when 1233E is the target compound, the high temperature side is thermodynamically unfavorable for 1233E. The reaction temperature is usually higher than or equal to 150° C. and lower than or equal to 800° C. When the reaction target is 1233E, the reaction temperature is preferably higher than or equal to 150° C. and lower than or equal to 450° C., and more preferably higher than or equal to 200° C. and lower than or equal to 350° C. When the reaction temperature is lower than 150° C., a sufficient amount of radical is not generated, and therefore the reaction rate may be too low. By contrast, when the reaction temperature is higher than 800° C., the material or the product becomes an oily substance having a high boiling point or is coked, which is not preferable.

For the reaction, a batch system or a flow system is usable. A gas phase flow system, which is industrially highly productive, is preferable. There is no specific limitation on the reaction pressure. It is easy to make an operation for the reaction at normal pressure or in the vicinity thereof. It should be noted that a reaction pressure higher than or equal to 1 MPa is not preferable because such a pressure requires a costly pressure-resistant device and also may cause undesirable polymerization of the material or the product.

As described above, in the case of a gas phase flow system, the productivity is usually discussed with a value obtained by dividing the capacity of the reaction zone by the material supply rate. In the case where the reaction zone is filled with a catalyst, such a value is referred to as "contact time". The term "contact time" is used for the sake of convenience although a solid catalyst is not used in the production of trans-1-chloro-3,3,3-trifluoropropene (1233E) according to the present invention.

According to the present invention, any contact time is usable with no specific limitation as long as the isomerization progresses sufficiently. The contact time is usually longer than or equal to 0.01 seconds and shorter than or equal to 50 seconds, and preferably longer than or equal to 0.05 seconds and shorter than or equal to 20 seconds. When the contact time is shorter than the above, the conversion ratio may be significantly different from the thermodynamic equilibrium composition. By contrast, when the contact time is longer than the above, the productivity is poor or the material or the product is turned into tar even if the conversion ratio is close to the equilibrium composition.

A mixture of 1233EZ obtained by the isomerization is washed to be deprived of the radical generating agent and an acid component, dried with zeolite or the like, and then subjected to a usual distillation operation so that 1233E and 1233Z can be isolated from each other. The resultant unreacted 1233Z may be reused as a material for an isomerization reaction.

Figure 9:
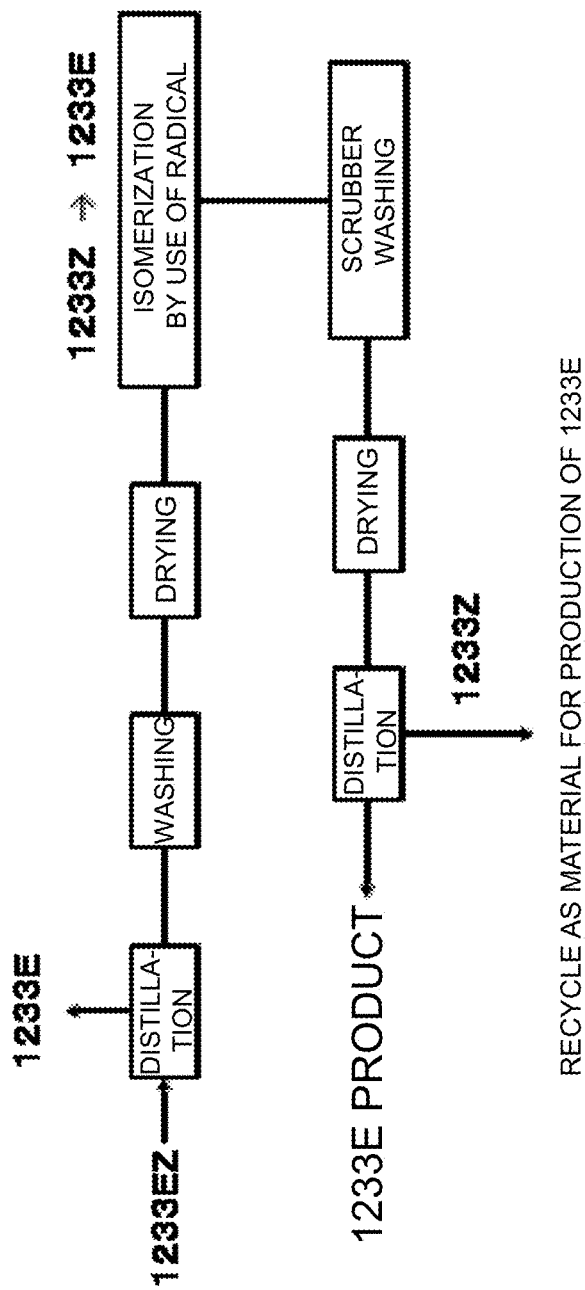
FIG. 9 is a schematic view showing an example of production process of a trans isomer (1233E) to which an isomerization method according to the present invention is applied.

In the isomerization reaction caused by use of a radical in the method for producing trans-1-chloro-3,3,3-trifluoropropene (1233E) according to the present invention, the process of producing the trans isomer (1233E) as a final product can be combined with any of various steps such as distillation and separation, washing, drying and the like. There is no specific limitation on the combination of the isomerization reaction and the steps. FIG. 9 shows an example of production process of 1233E that are usually performed. For the steps of distillation, washing and drying, a general system used in common steps for producing a chemical is usable with no specific limitation. For example, for the distillation operation, an appropriate continuous distillation system, batch distillation system or the like is usable. A drying agent may be optionally selected.

As shown in FIG. 9, the method for producing trans-1-chloro-3,3,3-trifluoropropene (1233E) may include a step of distilling 1-chloro-3,3,3-trifluoropropene (1233EZ) as a material to separate a trans isomer (1233E) and a cis isomer (1233Z) from each other; a subsequent step of performing washing with water or the like so that an acid component such as hydrochloric acid or the like is removed from the resultant mixture containing the cis isomer (1233Z) as a main component; a step of drying the resultant mixture containing, as a main component, the cis isomer (1233Z) deprived of the acid component with a drying agent such as zeolite or the like; a step of isomerizing the dried mixture containing the cis isomer (1233Z) as a main component by use of a radical to obtain a mixture containing a trans isomer (1233E); a step of water-washing the resultant mixture containing the trans isomer (1233E) by a scrubber system; a step of drying the resultant mixture containing the trans isomer (1233E) with a drying agent such as zeolite or the like; and a step of further distilling the dried mixture to obtain a highly pure trans isomer (1233E) usable as a product. 1233Z separated by the distillation may be recovered and reused as a material for producing 1233E. The step of water-washing the 1233E-containing mixture obtained by the isomerization reaction by use of the scrubber system provides an effect of removing the acid component by water washing and also an effect of cooling the gas. This makes it unnecessary to provide a cooling device separately, which is advantageous in term of cost. Between the step of water-washing by the scrubber system and the step of drying, another step of water-washing the resultant mixture to remove the acid component by a batch system or the like may be performed.

Examples

Hereinafter, production of trans-1-chloro-3,3,3-trifluoropropene (1233E) according to the present invention will be specifically described by way of examples. The present invention is not limited to the following examples. Herein, "%" used for a composition analysis value represents the "GC surface area %" of a composition of a reaction mixture measured by use of gas chromatography (detector: FID). Each displayed value is obtained by rounding off the numeral at the place smaller by one digit than the smallest place of the displayed value. For example, 0.00% represents a value smaller than 0.005 GC surface area %.

An isomerization reaction of cis-1-chloro-3,3,3-trifluoropropene (1233Z) (isomerization reaction to convert 1233Z into 1233E) was performed by use of the gas phase reaction device shown in FIG. 4. The gas phase reaction device shown in FIG. 4 is described above regarding the isomerization reaction of trans-1-chloro-3,3,3-trifluoropropene (1233E), and will not be described here.

The isomerization reaction was performed in the following procedure. While nitrogen was supplied from the carrier gas inlet, the sheath heaters of the top part and the bottom part of the reaction tube were each controlled to have a predetermined temperature by use of a PID temperature controller. Next, a material composition containing 1233Z was introduced from the material inlet at a predetermined supply rate, and at the same time, the supply of nitrogen was stopped. When the reaction showed a steady state, the generated gas was sampled at the gas sampling opening. The gas was analyzed by gas chromatography. Tables 6 to 8 show the results in examples C-1 through C-4 and comparative examples C-1 through C-3. Tables 6 to 8 also show the reaction conditions and the like in the examples and the comparative examples.

Example C-1

An isomerization reaction of a material composition containing a predetermined amount of carbon tetrachloride ($CCl_4$) as a radical generating agent and 1233Z was performed.

Comparative Example C-1

In a comparative example C-1, an isomerization reaction of a material composition containing 1233Z was performed without adding carbon tetrachloride ($CCl_4$). The reaction conditions were substantially the same as those in example C-1 except that carbon tetrachloride ($CCl_4$) was not added.

TABLE 6

| | 1233Z supply rate (g/min) | Reaction temperature (°C.) | Contact time (s) | Reaction product composition (surface area %) | | | |
|---|---|---|---|---|---|---|---|
| | | | | 1233E | 1233Z | CCl$_4$ | Others |
| Example C-1 | 0.41 | Material 350 | 9.2 | 0.01 71.51 | 86.63 14.05 | 0.30 0.25 | 13.06 13.95 |
| Comparative example C-1 | 0.43 | Material 350 | 8.6 | 0.02 9.05 | 87.02 78.68 | 0.00 0.00 | 12.96 12.27 |

As shown in Table 6, after the isomerization reaction, the ratio of 1233E/1233Z was 71.75/14.05=5.16. From this, it is seen that the isomerization reaction progressed even with merely 0.30% of carbon tetrachloride (CCl$_4$). By contrast, in comparative example C-1, the ratio of 1233E/1233Z after the isomerization reaction was 9.05/78.68=0.115. From this, it is seen that the isomerization reaction of 1233Z did not progress sufficiently as compared with example C-1.

Example C-2

The same experiment as that in example C-1 was performed except that 1233Z having a purity of 99.67% as a material was supplied at a supply rate of 0.41 g/min and chlorine gas as a radical generating agent was supplied at a supply rate of 2.4 ml/min (the molar ratio of chlorine/1233Z was 0.034, and the amount of chlorine was 3.4 mol %), into a reaction tube (formed of Hastelloy C276) heated to 200° C.

Comparative Example C-2

An experiment was performed in substantially the same conditions as those in example C-2 except that chlorine gas was not added.

TABLE 7

| | 1233Z supply rate (g/min) | Chlorine gas supply rate (ml/min) | Reaction temperature (°C.) | Contact time (s) | Reaction product composition (surface area %) | | |
|---|---|---|---|---|---|---|---|
| | | | | | 1233E | 1233Z | Others |
| Material | | | | | 0.01 | 99.67 | 0.32 |
| Example C-2 | 0.41 | 2.4 | 200 | 11.9 | 79.69 | 19.70 | 0.61 |
| Comparative example C-2 | 0.49 | 0.0 | 200 | 10.2 | 1.05 | 98.60 | 0.35 |

As shown in Table 7, in example C-2, the ratio of 1233E/1233Z after the isomerization reaction was 79.69/19.70=4.05. From this, it is seen that 1233Z was converted into 1233E at a high conversion ratio when the radical generating agent was added. By contrast, in comparative example C-2 in which no radical generating agent was added, the ratio of 1233E/1233Z was 1.05/98.6=0.011. The isomerization reaction did not substantially progress.

Examples C-3 and C-4

An isomerization reaction of a material containing 1233Z was performed using air as a radical generating agent instead of chlorine gas. Oxygen in the air is an effective component as the radical generating agent. The oxygen component in the composition of air is 20.9%. Therefore, the molar ratios of oxygen/1233Z in examples C-3 and C-4 are substantially 0.028 and 0.0028, respectively.

Comparative Example C-3

Experiments were performed in the same conditions as those in examples C-3 and C-4 except that air was not added.

TABLE 8

| | 1233Z supply rate | Air supply rate | Reaction temperature (° C.) | Contact time | Reaction product composition (surface area %) | | |
|---|---|---|---|---|---|---|---|
| | (g/min) | (ml/min) | | (s) | 1233E | 1233Z | Others |
| Material | | | | | 0.02 | 87.02 | 12.96 |
| Example C-3 | 0.43 | 10.0 | 300 | 8.4 | 70.29 | 16.13 | 13.58 |
| Example C-4 | 0.43 | 1.0 | 300 | 8.4 | 71.12 | 15.05 | 13.83 |
| Comparative example C-3 | 0.43 | 0 | 300 | 8.4 | 1.03 | 85.71 | 13.26 |

As can be seen from Table 8, 1233Z was converted into 1233E at a high conversion ratio when air was added as a radical generating agent. Referring to comparative example C-3, the isomerization reaction did not progress sufficiently when only nitrogen was added as a radical generating agent. This suggests that oxygen in the air is an effective component as the radical generating agent.

It has been found from the results in examples C-1 to C-4 and comparative example C-1 to C-3 that when a radical generating agent (chlorine or air) or the like is added, a radical is present in the reaction system and thus the isomerization reaction of 1233Z into 1233E can be performed and a high conversion ratio is provided even with no use of a solid catalyst.

From example C-4, it has been found that even when air (radical generating agent) is added in an extremely trace amount, the isomerization reaction of 1233Z into 1233E can be performed and a high conversion ratio is provided. Referring to comparative examples C-1 to C-3, even when a radical generating agent was not added, the isomerization reaction of 1233Z into 1233E progressed, but the conversion ratio was several percent, which was not sufficient. This suggests that presence of a radical in the reaction system allows the isomerization reaction of 1233Z to progress to provide a high conversion ratio. In the 1233E-containing composition obtained by the isomerization reaction, no byproduct difficult to be separated from 1233E was detected.

As described above, an isomerization reaction of cis-1-chloro-3,3,3-trifluoro-1-propene (1233Z) into trans-1-chloro-3,3,3-trifluoro-1-propene (1233E), when being provided with a radical generating agent, is progressed to provide a high conversion ratio even with no use of a solid catalyst.

For industrially isomerizing cis-1-chloro-3,3,3-trifluoro-1-propene (1233Z) into trans-1-chloro-3,3,3-trifluoro-1-propene (1233E), when the reaction is performed at a high temperature higher than or equal to 600° C., the reaction tube is corroded even when being mainly formed of a corrosion-resistant alloy containing nickel or the like. Even when being thick, the reaction tube needs to be exchanged every year. This disturbs smooth operations. By contrast, the method for producing trans-1-chloro-3,3,3-trifluoro-1-propene according to the present invention that includes an isomerization step of cis-1-chloro-3,3,3-trifluoro-1-propene (1233Z) into trans-1-chloro-3,3,3-trifluoro-1-propene (1233E) allows the reaction temperature to be decreased by 100° C. to 300° C. as compared with the conventional art by a catalytic action of a radical in the isomerization step. Therefore, the corrosion of the reaction tube can be prevented.

The isomerization reaction of cis-1-chloro-3,3,3-trifluoro-1-propene (1233Z) into trans-1-chloro-3,3,3-trifluoro-1-propene (1233E) can be progressed in catalyst-free and high-temperature conditions with no addition of a radical generating agent. The isomerization of cis-1-chloro-3,3,3-trifluoro-1-propene (1233Z) in the catalyst-free and high-temperature conditions is substantially the same as the isomerization reaction of trans-1-chloro-3,3,3-trifluoro-1-propene described above regarding the method for producing cis-1-chloro-3,3,3-trifluoro-1-propene (1233Z) except for the material compound to be used. As described above, the isomerization reaction of 1233Z into 1233E in a catalyst-free condition is not advantageous for thermodynamic equilibrium. Therefore, a high yield cannot be expected in the above-described practically usable temperature range. Thus, for performing an isomerization reaction of 1233Z into 1233E in a catalyst-free condition, it is preferable that the reaction product is separated into 1233E as the target compound and unreacted 1233Z and that the separated 1233Z is recovered and reused as a material composition.

Method for producing cis-1,3,3,3-tetrafluoropropene (1234Z)

Trans-1,3,3,3-tetrafluoropropene (1234E), which is a material of cis-1,3,3,3-tetrafluoropropene (1234Z), may be produced in any method with no specific limitation. For example, it is known that 1234E is easily synthesized by a reaction of industrially available 1,1,1,3,3-pentafluoropropane (HFC-245fa) and a base such as sodium hydroxide or the like. 1,1,1,3,3-pentafluoropropane (245fa) is obtained by the fluorination of 1233 described above. 1234E also can be obtained by fluorination of 1233E described above. 1234E itself is industrially produced as fireproof cover gas used for producing a magnesium alloy and thus is available.

A preferable material for the production of cis-1,3,3,3-tetrafluoropropene (1234Z) according to the present invention is 1234E purified by deoxidation, drying, distillation and the like. Unpurified crude 1234E also may be used. A mixture of 1234E and 1234Z is also usable.

Usually, trans-1,3,3,3-tetrafluoropropene (1234) obtained by a known production method is a mixture of 1234E and 1234Z. The ratio of 1234E and 1234Z depends on thermodynamic equilibrium. As shown by a calculation example of Boltzmann distributions in FIG. 10, the equilibrium ratio depends on temperature conditions. The equilibrium ratio also varies in accordance with the type or shape of the reaction vessel, or the reaction conditions such as the presence/absence of the catalyst and the like.

An isomerization reaction of trans-1,3,3,3-tetrafluoropropene (1234E) into cis-1,3,3,3-tetrafluoropropene (1234Z) is to cause the equilibrium ratio of 1234E:1234Z to achieve the thermodynamic equilibrium point quickly by a catalytic action of a radical. When the isomer ratio of 1234Z:1234E, namely, 1234Z/1234E, is lower than the equilibrium ratio, at least a part of 1234E is converted into 1234Z. When a material having a high content of 1234Z is used, the apparent conversion ratio from 1234E into 1234Z is decreased.

When 1234Z is to be obtained as the target compound, it is ideal to use pure 1234E as a material, but it is acceptable to use 1234EZ containing 1234Z in a material composition.

Paying attention to equilibrium, it is more preferable that the content of 1234Z in the material composition is lower. The ratio of 1234E in the material composition is higher than or equal to 50% by weight, preferably higher than or equal to 70% by weight, and more preferably higher than or equal to 90% by weight. It is more preferable that the mass ratio of 1234Z/1234E in the material is closer to zero. Specifically, the mass ratio of 1234Z/1234E is preferably 0 to 0.2, and more preferably 0 to 0.1. When 1234Z is the target compound, the material is 1234E. Therefore, the content of 1234E cannot be zero.

1234E and 1234Z can be easily separated from each other by distillation because of the difference in the boiling point. Therefore, when a mixture of 1234Z and 1234E is used as a material, it is preferable to first perform distillation for separation. When 1234Z is the target compound, it is preferable to distill the mixture including 1234Z and 1234E to separate 1234Z and 1234E from each other so that 1234Z separated from 1234E is used as a product and 1234E separated from 1234Z is used as a material for an isomerization reaction of 1234E into 1234Z.

It is preferable that a product containing 1234Z obtained by the isomerization of 1234E is collected, 1234E and 1234Z are isolated from each other by distillation or the like, and then unreacted 1234E is reused as a material. This allows the material to be used efficiently.

In an isomerization step of 1234E into 1234Z, a radical is generated in a reaction system in a predetermined temperature range. This progresses an isomerization reaction of converting 1234E into 1234Z. According to a preferable method for generating a radical in a system, a radical generating agent is added to the system as described above. A radical generating agent may be at least one selected from halogen gas such as chlorine, bromine and the like; oxygen-containing gas such as air, oxygen, ozone, hydrogen peroxide, nitrogen oxide and the like; and carbon halide. An especially preferable radical generating agent is air or oxygen. The details of the carbon halide is described above and will not be described here. Examples of carbon halide, which is usable as a radial generating agent, do not include 1,3,3,3-tetrafluoropropene (1234), which is a material of the present invention.

According to a method for putting a radical into contact with a material composition containing 1234E by a gas phase reaction, a radical generating agent may be provided with light or heat to be activated beforehand and then introduced into a reaction tube, or a mixture of a radical generating agent and a material composition containing 1234E may be introduced into a reaction tube and then activated with light or heat. For putting a radical into contact with 1234E efficiently, it is preferable to supply a radical generating agent and a material composition containing 1234E into a reaction tube at the same time in the form of a mixture. When a material composition containing 1234E is to be supplied, inert gas such as nitrogen or the like may be supplied, together with the material composition, in an amount that is sufficiently small so as not to decrease the productivity. From an industrial viewpoint, it is simple and preferable that a mixture of a radical generating agent and a material composition containing 1234E is put into a heated reaction tube and is provided with thermal energy in the reaction tube to generate a thermal radical.

Specifically, according to a preferable method for producing 1234Z as the target compound, a mixture containing trans-1,3,3,3-tetrafluoropropene (1234E) and at least one radical generating agent selected from the group consisting of chlorine, oxygen, bromine, air, hydrogen peroxide, ozone, nitrogen oxide, and carbon halide is heated to isomerize at least a part of trans-1,3,3,3-tetrafluoropropene (1234E) into cis-1,3,3,3-tetrafluoropropene (1234Z) by an isomerization reaction caused in the presence of a radical. The isomerization reaction caused in the presence of the radical converts at least a part of trans-1,3,3,3-tetrafluoropropene (1234E) into cis-1,3,3,3-tetrafluoropropene (1234Z), so that the ratio of the cis-1,3,3,3-tetrafluoropropene (1234Z) with respect to the trans-1,3,3,3-tetrafluoropropene (1234E) can be increased.

The generation of a radical occurs in a chain-reacting manner. Therefore, it is preferable that a radical generating agent is supplied in a trace amount. As described above, provision of an excessive amount of radical generating agent is a waste of the sub material and also imposes, after the reaction, a load on a step of separating the radical generating agent from 1234. Even when air, which is relatively easily separable, is added in a large amount, the capability of a condensation step or a distillation step is lowered. When an excessive amount of chlorine as a radical generating agent is added, a compound containing chlorine added to the double bond is produced as a byproduct. Especially, a compound containing chlorine added to 1234 is HCFC, which causes global warming or depletion of ozone layer. Therefore, it is more preferable that the amount of a byproduct containing chlorine is smaller.

The present inventors performed an experiment with the ratio of the radical generating agent to the material composition being varied. Even when the amount of chlorine was decreased down to the lower limit of measurement of the chlorine flowmeter, no substantial influence was found on the conversion ratio from 1234E into 1234Z. From this, it has been found that the amount of the radical generating agent may be an extremely trace amount (experimental results will be described later). It should be noted that the optimal amount of the radical generating agent depends on the type of the radical generating agent or the structure of the reaction tube. When a reaction tube highly suitable for the mixing is used, a desired conversion ratio is achieved even with a trace amount of radical generating agent. In other cases, the amount of the radical generating agent to be added may be increased to raise the concentration of the radical, so that the conversion ratio is increased.

As described above, the amount of the radical generating agent depends on the type of the radical generating agent or the shape of the reaction tube. Usually, the amount of the radical generating agent with respect to 1234E, which is the material, is preferably higher than or equal to 0.0001 mol % and lower than or equal to 10 mol %, and more preferably higher than or equal to 0.0001 mol % and lower than or equal to 0.005 mol %. When a reaction tube highly suitable for putting the radical into contact with 1234E is used, 1234E and the radical can contact each other sufficiently. Therefore, the amount of the radical generating agent with respect to 1234E is preferably higher than or equal to 0.0001 mol % and lower than or equal to 0.005 mol %.

A reaction tube highly suitable for putting the radical into contact with 1234E has, for example, a filler that is inactive to the reaction, such as a static mixer, a Raschig ring, a Pall ring, a metal mesh or the like, packed therein. According to the present invention, a filler may be packed in the reaction tube, needless to say. A reaction tube having a high length/inner diameter ratio allows the radical and 1234E to be put into contact with each other efficiently even when being empty with no filler as described above and also has high heat conductivity, and thus is especially preferable. Specifically, the length/inner diameter ratio of the reaction tube is higher than or equal to 10 and lower than or equal to 1000, and preferably higher than or equal to 20 and lower than or equal to 500. When the length/inner diameter ratio is lower than 10, the radical and 1234E may not be put into sufficient contact with each other; and when the length/inner diameter ratio is higher than 1000, the device cost may be raised, or the pressure loss may be too large in certain operation conditions. It is usually preferable that the inner diameter of the reaction tube is longer than or equal to 8 mm and shorter than or equal to 150 mm, and that the length of the reaction tube is longer than or equal to 1 m and shorter than or equal to 200 m. It is especially preferable that the inner diameter of the reaction tube is longer than or equal to 10 mm and shorter than or equal to 60 mm, and that the length of the reaction tube is longer than or equal to 2 m and shorter than or equal to 50 m. Especially preferably, the reaction tube is empty. There is no specific limitation on the shape of the reaction tube. The reaction tube may be straight, coiled, or folded by use of a joint or the like.

A preferable material of the reaction tube or the like is carbon, ceramics, stainless steel, nickel, a nickel alloy (trade name: Hastelloy™, Inconel™, Monel™), or the like. Regarding an alloy containing iron as a main component, it is usually more preferable that an iron content is lower and a content of nickel, chromium or the like is higher because the alloy has a higher corrosion resistance with such a composition. When the reaction tube is to be used for a small device, a quartz tube or the like may be used as the reaction tube. A reaction tube with no filler may be used. When desired, a static mixer may be used, or the reaction tube may be provided with a filler such as a Raschig ring, a Pall ring or the like. It is preferable that such a filler is formed of a corrosion-resistant material as described above. In the case where the reaction device is to be heated, there is no specific limitation on the heating method. The reaction device may be directly heated by an electric heater or a burner, or may be indirectly heated by use of melted salt or sand.

As described above, the generation of a radical occurs in a chain-reacting manner. Therefore, at a reaction temperature at which the radical generating agent can generate a radical, even though rebinding occurs, recleavage occurs. Thus, an isomerization reaction of 1234E is promoted even with a trace amount of the radical generating agent. Namely, in a method for producing 1,3,3,3-tetrafluoropropene according to the present invention including a trans (1234E)-cis (1234Z) isomerization step of 1,3,3,3-tetrafluoropropene (1234), the isomerization reaction progresses even when a trace amount of catalyst is added.

In a method for producing cis-1,3,3,3-tetrafluoropropene (1234Z) according to the present invention, a solid catalyst is not indispensable. However, a solid catalyst may be used in order to quickly progress the isomerization reaction in the presence of a radical. Examples of the usable solid catalyst include metal, metal oxide, metal halide, activated carbon, and the like, and also a composite thereof (e.g., metal-supported activated carbon). When a solid catalyst is used in a high reaction temperature range higher than or equal to 350° C., it is preferable to use a solid catalyst that is inactivated by being baked at a temperature higher than or equal to 1300° C. in a nitrogen atmosphere because 1234E is likely to be coked on a surface of the catalyst or may generate oil.

In a method for producing cis-1,3,3,3-tetrafluoropropene (1234Z) according to the present invention, a solid catalyst may be used. However, it is preferable to perform the isomerization reaction by use of an empty column reactor with no catalyst, filler or the like, so that the efficiency of the isomerization reaction in the presence of a radical is not decreased. The "empty column" refers to that there is no object such as a catalyst, a filler or the like in an inner space of the reactor or the reaction column. When there is an object such as a catalyst, a filler or the like in an isomerization reaction area, the generated radical may be extinguished to stop the chain reaction of the radical generation, which decreases the efficiency of the isomerization. Therefore, in a method for producing cis-1,3,3,3-tetrafluoropropene (1234Z) according to the present invention, it is especially preferable to perform the isomerization reaction in an empty column of a gas phase flow system (see the examples described below).

When a solid catalyst is added, there may be a non-preferable case where the radical generating agent and 1234E cause an unexpected reaction that is not an isomerization reaction. In this case, 1234E as a reaction material may be merely converted into a non-preferable byproduct and the radical generating agent may be consumed for the reaction with 1234E, which is not preferable.

As shown above by the calculation example of the Boltzmann distributions (see FIG. 10), the ratio of 1234E/1234Z is higher when the temperature is lower. The reaction temperature is usually higher than or equal to 150° C. and lower than or equal to 700° C. When the reaction target is 1234Z, the reaction temperature is preferably higher than or equal to 300° C. and lower than or equal to 700° C., and more preferably higher than or equal to 350° C. and lower than or equal to 650° C. A preferable reaction temperature is, in other words, a temperature at which a radical is efficiently generated from the radical generating agent. When the reaction temperature is lower than 150° C., a sufficient amount of radical is not generated, and therefore the reaction rate may be too low. By contrast, when the reaction temperature is higher than 700° C., the material or the product becomes an oily substance having a high boiling point or is coked, which is not preferable.

For the reaction, a batch system or a flow system is usable. A gas phase flow system, which is industrially highly productive, is preferable. There is no specific limitation on the reaction pressure. It is easy to make an operation for the reaction at normal pressure or in the vicinity thereof. It should be noted that a reaction pressure higher than or equal to 1 MPa is not preferable because such a pressure requires a costly pressure-resistant device and also may cause undesirable polymerization of the material or the product.

In the case of a gas phase flow system, the productivity is usually discussed with a value obtained by dividing the capacity of the reaction zone by the material supply rate. In the case where the reaction zone is filled with a catalyst, such a value is referred to as "contact time". The term "contact time" is used for the sake of convenience although a solid catalyst is not used in the production of cis-1,3,3,3-tetrafluoropropene (1234Z) according to the present invention described later.

According to the present invention, any contact time is usable with no specific limitation as long as the isomerization progresses sufficiently. The contact time is usually longer than or equal to 0.01 seconds and shorter than or equal to 50 seconds, and preferably longer than or equal to 0.05 seconds and shorter than or equal to 20 seconds. In general, when the contact time is shorter than the above, the conversion ratio may be significantly different from the thermodynamic equilibrium composition. By contrast, when the contact time is longer than the above, the productivity is poor or the material or the product is turned into tar even if the conversion ratio is close to the equilibrium composition.

A mixture of 1234EZ obtained by the isomerization is washed to be deprived of the radical generating agent and an acid component, dried with zeolite of the like, and then subjected to a usual distillation operation so that 1234E and 1234Z can be isolated from each other. The resultant unreacted 1234E may be reused as a material for an isomerization reaction.

It is known that in an isomerization reaction of obtaining 1234Z from 1234E as a material by use of a solid catalyst such as Lewis acid or the like, 1,1,1,3,3-pentafluoropropane (HFC-245fa) is produced as a byproduct by adding hydrogen fluoride to 1234. In this case, HFC-245fa and 1234Z have boiling points close to each other and thus form an azeotrope-like composition, and therefore are very difficult to be separated from each other by distillation. However, in the isomerization method of obtaining 1234Z from 1234E as a material according to the present invention, the isomerization progresses without producing HFC-245fa as a byproduct (see example 7 described later). Therefore, highly pure 1234Z can be obtained easily.

Examples

Hereinafter, production of cis-1,3,3,3-tetrafluoropropene (1234Z) according to the present invention will be specifically described by way of examples. The present invention is not limited to the following examples. Herein, "%" used for a composition analysis value represents the "surface area %" of a composition of a reaction mixture measured by use of gas chromatography (detector: FID). Each displayed value is obtained by rounding off the numeral at the place smaller by one digit than the smallest place of the displayed value. For example, 0.00% represents a value smaller than 0.005 surface area %.

While nitrogen gas was supplied at a flow rate of about 100 ml/min. to a gas phase reaction device (formed of SUS316L; inner diameter: 6 mm; length: 260 mm) formed of a cylindrical reaction tube provided with an external heating device, the temperature of the reaction tube was raised to 650° C. The gas phase reaction device used in the examples has a similar structure to that of the gas phase reaction device shown in FIG. 4.

Next, trans-1,3,3,3-tetrafluoropropene (99.94%) vaporized beforehand was started to be supplied as a material to the reaction tube at a rate of about 0.45 g/min. When the flow rate of the material was stabilized, the supply of nitrogen gas was stopped.

One hour after the start of the reaction, it was confirmed that the reaction was stable, and the gas flowing out of the reactor was blown into water to remove acid gas. Then, the product was analyzed by gas chromatography. Tables 9 and 10 show the results. In all the examples and the comparative example, the isomerization reaction was performed with no filler such as a catalyst or the like being provided in the reactor, namely, in an empty column (in an empty state of the reactor).

Examples D-1 to D-3

In examples D-1 to D-3, chlorine gas was used as a radical generating agent. Chlorine gas was supplied into the reaction tube with the supply amount thereof being varied to cause an isomerization reaction of 1234E. Table 9 shows the results. In examples D-1 to D-3, the ratios of chlorine gas were 1.8 mol %, 0.6 mol % and 0.1 mol % respectively, and the molar ratios of chlorine/1234E were 0.018, 0.0056 and 0.0011 respectively.

Examples D-4 to D-6

In examples D-4 to D-6, air was used as a radical generating agent. Air was supplied into the reaction tube with the supply amount thereof being varied to cause an isomerization reaction of 1234E. Table 9 shows the results. In examples D-4 to D-6, the ratios of air were 3.4 mol %, 2.3 mol % and 1.1 mol % respectively, and the molar ratios of air/1234E were 0.034, 0.022 and 0.011 respectively.

Comparative Example D-1

In comparative example D-1, an experiment was performed substantially the same conditions as those in example D-1 except that no radical generating agent was added.

Example D-7

Highly pure trans-1,3,3,3-tetrafluoropropene (purity: higher than or equal to 99.99%) as a material and 2.3 mol % of air as a radical generating agent were supplied into the reaction tube to cause an isomerization reaction. Table 10 shows the results.

TABLE 9

| | 1233E supply rate (ml/min) | Chlorine supply rate (ml/min) | Air supply rate (ml/min) | Contact time (s) | Reaction product composition (surface area %) | | |
|---|---|---|---|---|---|---|---|
| | | | | | 1234E | 1234Z | Others |
| Material | | | | | 99.94 | 0.03 | 0.03 |
| Comparative example D-1 | 88.0 | 0.0 | 0.0 | 5.1 | 94.2 | 4.8 | 0.94 |
| Example D-1 | 87.8 | 1.6 | 0.0 | 4.9 | 62.8 | 24.8 | 12.37 |
| Example D-2 | 88.8 | 0.5 | 0.0 | 4.9 | 71.9 | 25.9 | 2.19 |
| Example D-3 | 87.5 | 0.1 | 0.0 | 5.0 | 74.2 | 24.2 | 1.55 |
| Example D-4 | 85.1 | 0.0 | 3.0 | 5.0 | 80.6 | 18.2 | 1.15 |
| Example D-5 | 86.1 | 0.0 | 2.0 | 5.0 | 83.1 | 15.8 | 1.14 |
| Example D-6 | 86.7 | 0.0 | 1.0 | 5.0 | 90.4 | 8.4 | 1.17 |

TABLE 10

| | 1233E supply rate | Chlorine supply rate | Air supply rate | Contact time | Reaction product composition (surface area %) | | | |
|---|---|---|---|---|---|---|---|---|
| | (ml/min) | (ml/min) | (ml/min) | (s) | 1234E | 245fa | 1234Z | Others |
| Material | | | | | 99.99 | 0.00 | 0.00 | 0.01 |
| Example D-7 | 83.1 | 0.0 | 2.0 | 5.2 | 78.19 | 0.00 | 20.59 | 1.22 |

It has been found from the results in examples D-1 to D-7 and comparative example D-1 that when chlorine or air as a radical generating agent is added, the isomerization reaction of 1234E into 1234Z is caused and a high conversion ratio is provided even with no use of a solid catalyst. In example D-7, 1,1,1,3,3-pentafluoropropane (245fa) was not detected as a byproduct from the reaction product of the isomerization reaction according to the present invention. From this, it was found that 245fa, which would have been difficult to be separated from 1234Z, was not produced as a byproduct in the isomerization reaction according to the present invention.

From example D-3, it has been found that even when chlorine gas is added in an extremely trace amount as a radical generating agent, the isomerization reaction of 1234E into 1234Z can be performed and a high conversion ratio is provided. Referring to comparative example D-1, even when a radical generating agent was not added, the isomerization reaction of 1234E into 1234Z progressed, but the conversion ratio was several percent, which was not sufficient.

As described above, an isomerization reaction of trans-1,3,3,3-tetrafluoropropene (1234E) into cis-1,3,3,3-tetrafluoropropene (1234Z), when being provided with a radical generating agent, is progressed to provide a high conversion ratio even with no use of a solid catalyst.

For industrially isomerizing trans-1,3,3,3-tetrafluoropropene (1234E) into cis-1,3,3,3-tetrafluoropropene (1234Z), when the reaction is performed at a high temperature higher than or equal to 600° C., the reaction tube is corroded even when being mainly formed of a corrosion-resistant alloy containing nickel or the like. Even when being thick, the reaction tube needs to be exchanged every year. This disturbs smooth operations. By contrast, the method for producing cis-1,3,3,3-tetrafluoropropene (1234Z) according to the present invention that includes an isomerization step of trans-1,3,3,3-tetrafluoropropene (1234E) into cis-1,3,3,3-tetrafluoropropene (1234Z) allows the reaction temperature to be decreased by 100° C. to 300° C. as compared with the conventional art by a catalytic action of a radical in the isomerization step. Therefore, the corrosion of the reaction tube can be prevented.

The isomerization reaction of trans-1,3,3,3-tetrafluoropropene (1234E) into cis-1,3,3,3-tetrafluoropropene (1234Z) can be progressed in catalyst-free and high-temperature conditions with no addition of a radical generating agent. The isomerization of trans-1,3,3,3-tetrafluoropropene (1234E) in the catalyst-free and high-temperature conditions is substantially the same as the isomerization reaction of trans-1-chloro-3,3,3-trifluoro-1-propene described above regarding the method for producing cis-1-chloro-3,3,3-trifluoro-1-propene (1233Z) except for the material compound to be used and the reaction temperature. For isomerizing trans-1,3,3,3-tetrafluoropropene (1234E) in a catalyst-free condition, the reaction temperature is higher than or equal to 500° C. and lower than or equal to 900° C., and preferably higher than or equal to 600° C. and lower than or equal to 800° C. 1,3,3,3-tetrafluoropropene (1234EZ) is a compound more stable than 1-chloro-3,3,3-trifluoro-1-propene (1233EZ) and is not likely to be turned into tar or oil even at a temperature higher than or equal to 600° C. and lower than or equal to 800° C. Therefore, the isomerization can be efficiently performed in a temperature range higher than or equal to 600° C. and lower than or equal to 800° C.

Method for producing trans-1,3,3,3-tetrafluoropropene (1234E)

Cis-1,3,3,3-tetrafluoropropene (1234Z), which is a material of trans-1,3,3,3-tetrafluoropropene (1234E), may be produced in any method with no specific limitation. For example, it is known that 1234Z is easily synthesized by a reaction of industrially available 1,1,1,3,3-pentafluoropropane (HFC-245fa) and a base such as sodium hydroxide or the like. As described above, 1,1,1,3,3-pentafluoropropane (245fa) is obtained by the fluorination of 1233. 1234Z also can be obtained by fluorination of 1233Z described above.

A preferable material for the production of trans-1,3,3,3-tetrafluoropropene (1234E) according to the present invention is 1234Z purified by deoxidation, drying, distillation and the like. Unpurified crude 1234Z also may be used. A mixture of 1234E and 1234Z is also usable.

As described above, usually, 1,3,3,3-tetrafluoropropene (1234) obtained by a known production method is a mixture of 1234E and 1234Z. The ratio of 1234E and 1234Z depends on thermodynamic equilibrium. As shown by the calculation example of the Boltzmann distributions in FIG. 10, the equilibrium ratio depends on temperature conditions. The equilibrium ratio also varies in accordance with the type or shape of the reaction vessel, or the reaction conditions such as the presence/absence of the catalyst and the like.

An isomerization reaction of cis-1,3,3,3-tetrafluoropropene (1234Z) into trans-1,3,3,3-tetrafluoropropene (1234E) is to cause the equilibrium ratio of 1234E:1234Z to achieve the thermodynamic equilibrium point quickly by a catalytic action of a radical. When the isomer ratio of 1234Z:1234E, namely, 1234Z/1234E, is higher the equilibrium ratio, at least a part of 1234Z is converted into 1234E. When a material having a high content of 1234E is used, the apparent conversion ratio from 1234Z into 1234E is decreased.

When 1234E is to be obtained as the target compound, it is ideal to use pure 1234Z as a material, but it is acceptable to use 1234EZ containing 1234E in a material composition. Paying attention to equilibrium, it is more preferable that the content of 1234E in the material composition is lower. The ratio of 1234Z in the material composition is higher than or equal to 50% by weight, preferably higher than or equal to 70% by weight, and more preferably higher than or equal to 90% by weight. It is more preferable that the mass ratio of 1234E/1234Z in the material is closer to zero. Specifically, the mass ratio of 1234E/1234Z is preferably 0 to 0.2, and more preferably 0 to 0.1. When 1234E is the target compound, the material is 1234Z. Therefore, the content of 1234Z cannot be zero.

1234E and 1234Z can be easily separated from each other by distillation because of the difference in the boiling point.

Therefore, when a mixture of 1234Z and 1234E is used as a material, it is preferable to first perform distillation for separation. When 1234E is the target compound, it is preferable to distill the mixture of 1234Z and 1234E to separate 1234Z and 1234E from each other so that 1234E separated from 1234Z is used as a product and 1234Z separated from 1234E is used as a material for an isomerization reaction of 1234Z into 1234E.

It is reasonable and preferable from the viewpoint of efficient use of the material that a product containing 1234E obtained by the isomerization of 1234Z is collected, 1234E and 1234Z are isolated from each other by distillation or the like, and then unreacted 1234Z is reused as a material.

In an isomerization step of 1234Z into 1234E, a radical is generated in a reaction system in a predetermined temperature range. This progresses an isomerization reaction of converting 1234Z into 1234E. According to a preferable method for generating a radical in a system, a radical generating agent is added to the system as described above. A radical generating agent may be at least one selected from halogen gas such as chlorine, bromine and the like; oxygen-containing gas such as air, oxygen, ozone, hydrogen peroxide, nitrogen oxide and the like; and carbon halide. An especially preferable radical generating agent is air or oxygen. The details of the carbon halide is described above and will not be described here. Examples of carbon halide, which is usable as a radial generating agent, do not include 1,3,3,3-tetrafluoropropene (1234), which is a material of the present invention.

According to a method for putting a radical into contact with a material composition containing 1234Z by a gas phase reaction, a radical generating agent may be provided with light or heat to be activated beforehand and then introduced into a reaction tube, or a mixture of a radical generating agent and a material composition containing 1234Z may be introduced into a reaction tube and then activated with light or heat. For putting a radical into contact with 1234Z efficiently, it is preferable to supply a radical generating agent and a material composition containing 1234Z to a reaction tube at the same time in the form of a mixture. When a material composition containing 1234Z is to be supplied, inert gas such as nitrogen or the like may be supplied, together with the material composition, in an amount that is sufficiently small so as not to decrease the productivity. From an industrial viewpoint, it is simple and preferable that a mixture of a radical generating agent and a material composition containing 1234Z is put into a heated reaction tube and is provided with thermal energy in the reaction tube to generate a thermal radical.

Specifically, according to a preferable method for producing 1234E as the target compound, a mixture containing cis-1,3,3,3-tetrafluoropropene (1234Z) and at least one radical generating agent selected from the group consisting of chlorine, oxygen, bromine, air, hydrogen peroxide, ozone, nitrogen oxide, and carbon halide is heated to isomerize at least a part of cis-1,3,3,3-tetrafluoropropene (1234Z) into trans-1,3,3,3-tetrafluoropropene (1234E) by an isomerization reaction caused in the presence of a radical. The isomerization reaction caused in the presence of the radical converts at least a part of cis-1,3,3,3-tetrafluoropropene (1234Z) into trans-1,3,3,3-tetrafluoropropene (1234E), so that the ratio of the trans-1,3,3,3-tetrafluoropropene (1234E) with respect to the cis-1,3,3,3-tetrafluoropropene (1234Z) can be increased.

It is preferable that a radical generating agent is supplied in a trace amount. Provision of an excessive amount of radical generating agent is a waste of the sub material and also imposes, after the reaction, a load on a step of separating the radical generating agent from 1234. Even when air, which is relatively easily separable, is added in a large amount, the capability of a condensation step or a distillation step is lowered. When an excessive amount of chlorine as a radical generating agent is added, a compound containing chlorine added to the double bond is produced as a byproduct as described above. Especially, a compound containing chlorine added to 1234 is HCFC, which causes global warming or depletion of ozone layer. Therefore, it is more preferable that the amount of a byproduct containing chlorine is smaller.

The present inventors performed an experiment with the ratio of the radical generating agent to the material composition being varied. As a result, even when the amount of chlorine was decreased down to the lower limit of measurement of the chlorine flowmeter, no substantial influence was recognized on the conversion ratio from 1234Z into 1234E. From this, it has been found that the amount of the radical generating agent may be an extremely trace amount (experimental results will be described later). It should be noted that the optimal amount of the radical generating agent depends on the type of the radical generating agent or the structure of the reaction tube as described above. When a reaction tube highly suitable for the mixing is used, a desired conversion ratio is achieved even with a trace amount of radical generating agent. In other cases, the amount of the radical generating agent to be added may be increased to raise the concentration of the radical, so that the conversion ratio is increased.

As described above, the amount of the radical generating agent depends on the type of the radical generating agent or the shape of the reaction tube. Usually, the amount of the radical generating agent with respect to 1234Z, which is the material, is preferably higher than or equal to 0.0001 mol % and lower than or equal to 10 mol %, and more preferably higher than or equal to 0.0001 mol % and lower than or equal to 0.005 mol %. When a reaction tube highly suitable for putting the radical into contact with 1234Z is used, 1234Z and the radical can collide against each other sufficiently. Therefore, the amount of the radical generating agent with respect to 1234Z is preferably higher than or equal to 0.0001 mol % and lower than or equal to 0.005 mol %.

A reaction tube highly suitable for putting the radical into contact with 1234Z may be any reaction tube described above regarding the isomerization reaction of trans-1,3,3,3-tetrafluoropropene (1234E) into cis-1,3,3,3-tetrafluoropropene (1234Z). When desired, a static mixer may be used, or the reaction tube may be provided with a filler such as a Raschig ring, a Pall ring or the like. In the case where the reaction device is to be heated, there is no specific limitation on the heating method. The reaction device may be directly heated by an electric heater or a burner, or may be indirectly heated by use of melted salt or sand.

As described above, the generation of a radical occurs in a chain-reacting manner. Therefore, at a reaction temperature at which the radical generating agent can generate a radical, even though rebinding occurs, recleavage occurs. Thus, an isomerization reaction of 1234Z is promoted even with a trace amount of the radical generating agent. Namely, in a method for producing 1,3,3,3-tetrafluoropropene including a cis (1234Z)-trans (1234E) isomerization step of 1,3,3,3-tetrafluoropropene (1234), the isomerization reaction progresses even when a trace amount of catalyst is added.

In a method for producing trans-1,3,3,3-tetrafluoropropene (1234E) according to the present invention, a solid catalyst is not indispensable. However, a solid catalyst may be used in order to quickly progress the isomerization reaction in the presence of a radical. Examples of the usable solid catalyst include those listed above regarding the method for producing cis-1,3,3,3-tetrafluoropropene (1234Z).

Like in the method for producing cis-1,3,3,3-tetrafluoropropene (1234E), in a method for producing trans-1,3,3,3-tetrafluoropropene (1234Z) according to the present invention, it is preferable to perform the isomerization reaction by use of an empty column reactor with no catalyst, filler or the like, so that the efficiency of the isomerization reaction in the presence of a radical is not decreased. It is especially preferable to cause the isomerization reaction in an empty column of a gas phase flow system (see the examples described below).

When a solid catalyst is added, there may be a non-preferable case where the radical generating agent and 1234Z cause an unexpected reaction that is not an isomerization reaction. In this case, 1234Z as a reaction material may be merely converted into a non-preferable byproduct and the radical generating agent may be consumed for the reaction with 1234Z, which is not preferable.

As shown above by the calculation example of the Boltzmann distributions (see FIG. 10), the ratio of 1234E/1234Z is higher when the temperature is lower. The reaction temperature is usually higher than or equal to 150° C. and lower than or equal to 700° C. When the reaction target is 1234E, the reaction temperature is preferably higher than or equal to 300° C. and lower than or equal to 700° C., and more preferably higher than or equal to 350° C. and lower than or equal to 650° C. When the reaction temperature is lower than 150° C., a sufficient amount of radical is not generated, and therefore the reaction rate may be too low. By contrast, when the reaction temperature is higher than 700° C., the material or the product becomes an oily substance having a high boiling point or is coked, which is not preferable.

For the reaction, a batch system or a flow system is usable. A gas phase flow system, which is industrially highly productive, is preferable. There is no specific limitation on the reaction pressure. It is easy to make an operation for the reaction at normal pressure or in the vicinity thereof. It should be noted that a reaction pressure higher than or equal to 1 MPa is not preferable because such a pressure requires a costly pressure-resistant device and also may cause undesirable polymerization of the material or the product.

As described above, in the case of a gas phase flow system, the productivity is usually discussed with a value obtained by dividing the capacity of the reaction zone by the material supply rate. In the case where the reaction zone is filled with a catalyst, such a value is referred to as "contact time". The term "contact time" is used for the sake of convenience although a solid catalyst is not used in the production of trans-1,3,3,3-tetrafluoropropene (1234E) according to the present invention.

According to the present invention, any contact time is usable with no specific limitation as long as the isomerization progresses sufficiently. The contact time is usually longer than or equal to 0.01 seconds and shorter than or equal to 50 seconds, and preferably longer than or equal to 0.05 seconds and shorter than or equal to 20 seconds. When the contact time is shorter than the above, the conversion ratio may be significantly different from the thermodynamic equilibrium composition. By contrast, when the contact time is longer than the above, the productivity is poor or the material or the product is turned into tar even if the conversion ratio is close to the equilibrium composition.

A mixture of 1234EZ obtained by the isomerization is washed to be deprived of the radical generating agent and an acid component, dried with zeolite or the like, and then subjected to a usual distillation operation so that 1234E and 1234Z can be isolated from each other. The resultant 1234Z may be reused as a material for an isomerization reaction.

Examples

Hereinafter, production of trans-1,3,3,3-tetrafluoropropene (1234E) according to the present invention will be specifically described by way of examples. The present invention is not limited to the following examples. Herein, "%" used for a composition analysis value represents the "surface area %" of a composition of a reaction mixture measured by use of gas chromatography (detector: FID). Each displayed value is obtained by rounding off the numeral at the place smaller by one digit than the smallest place of the displayed value. For example, 0.00% represents a value smaller than 0.005 surface area %.

While nitrogen gas was supplied a flow rate of about 100 ml/min to a gas phase reaction device (formed of SUS316L; inner diameter: 6 mm; length: 260 mm) formed of a cylindrical reaction tube provided with an external heating device, the temperature of the reaction tube was raised to the temperatures shown in Tables 11 and 12. The gas phase reaction device used in the examples has a similar structure to that of the gas phase reaction device shown in FIG. 4.

Next, cis-1,3,3,3-tetrafluoropropene (99.94%) vaporized beforehand and a radical generating agent (chlorine or air) were started to be supplied to the reaction tube at flow rates shown in Tables 11 and 12. When the flow rate of the material was stabilized, the supply of nitrogen gas was stopped.

One hour after the start of the reaction, it was confirmed that the reaction was stable, and the gas flowing out of the reactor was blown into water to remove acid gas. Then, the product was analyzed by gas chromatography. Tables 11 and 12 show the results. In all the examples and the comparative examples, the isomerization reaction was performed with no filler such as a catalyst or the like being provided in the reactor, namely, in an empty column (in an empty state of the reactor). In examples E-1 to E-6, a radical generating agent was added. In comparative examples E-1 to E-3, no radical generating agent was added.

TABLE 11

|  | Reaction temperature (° C.) | 1234E supply rate (ml/min) | Chlorine supply rate (ml/min) | Contact time (s) | Reaction product composition (surface area %) | | |
|---|---|---|---|---|---|---|---|
|  |  |  |  |  | 1234E | 1234Z | Others |
| Material |  |  |  |  | 0.56 | 99.34 | 0.10 |
| Comparative example E-1 | 300 | 89.4 | 0.0 | 4.9 | 0.94 | 98.89 | 0.17 |
| Comparative example E-2 | 400 | 86.3 | 0.0 | 5.0 | 1.49 | 98.19 | 0.32 |
| Example E-1 | 300 | 86.4 | 1.0 | 5.0 | 23.16 | 76.32 | 0.52 |
| Example E-2 | 400 | 86.8 | 1.0 | 5.0 | 74.56 | 22.25 | 3.19 |

TABLE 11-continued

|  | Reaction temperature (° C.) | 1234E supply rate (ml/min) | Chlorine supply rate (ml/min) | Contact time (s) | Reaction product composition (surface area %) | | |
|---|---|---|---|---|---|---|---|
|  |  |  |  |  | 1234E | 1234Z | Others |
| Example E-3 | 500 | 86.7 | 1.0 | 5.0 | 72.48 | 23.81 | 3.71 |
| Example E-4 | 500 | 86.5 | 0.1 | 5.0 | 73.24 | 22.81 | 3.95 |

TABLE 12

|  | Reaction temperature (° C.) | 1234E supply rate (ml/min) | Air supply rate (ml/min) | Contact time (s) | Reaction product composition (surface area %) | | |
|---|---|---|---|---|---|---|---|
|  |  |  |  |  | 1234E | 1234Z | Others |
| Material |  |  |  |  | 0.56 | 99.34 | 0.10 |
| Comparative example E-3 | 650 | 92.5 | 0.0 | 4.8 | 11.45 | 87.22 | 1.33 |
| Example E-5 | 650 | 85.5 | 2.0 | 5.0 | 31.68 | 66.96 | 1.36 |
| Example E-6 | 650 | 77.0 | 4.0 | 5.4 | 52.59 | 45.83 | 1.58 |

It has been found from the results in examples E-1 to E-6 and comparative examples E-1 to E-3 that when chlorine or air as a radical generating agent is added, the isomerization reaction of 1233Z into 1234E is caused and a high conversion ratio is provided even with no use of a solid catalyst.

Referring to example E-4, it has been found that even when chlorine gas is added in an extremely trace amount as a radical generating agent, the isomerization reaction of 1234Z into 1234E is caused and a high conversion ratio is provided. Referring to comparative examples E-1 to E-3, even when a radical generating agent was not added, the isomerization reaction of 1234Z into 1234E progressed, but the conversion ratio was not sufficient.

As described above, an isomerization reaction of cis-1,3,3,3-tetrafluoropropene (1234Z) into trans-1,3,3,3-tetrafluoropropene (1234E), when being provided with a radical generating agent, is progressed to provide a high conversion ratio even with no use of a solid catalyst.

For industrially isomerizing cis-1,3,3,3-tetrafluoropropene (1234Z) into trans-1,3,3,3-tetrafluoropropene (1234E), when the reaction is performed at a high temperature higher than or equal to 600° C., the reaction tube is corroded even when being mainly formed of a corrosion-resistant alloy containing nickel or the like. Even when being thick, the reaction tube needs to be exchanged every year. This disturbs smooth operations. By contrast, the method for producing trans-1,3,3,3-tetrafluoropropene (1234E) according to the present invention that includes an isomerization step of cis-1,3,3,3-tetrafluoropropene (1234Z) into trans-1,3,3,3-tetrafluoropropene (1234E) allows the reaction temperature to be decreased by 100° C. to 300° C. as compared with the conventional art by a catalytic action of a radical in the isomerization step. Therefore, the corrosion of the reaction tube can be prevented.

The isomerization reaction of cis-1,3,3,3-tetrafluoropropene (1234Z) into trans-1,3,3,3-tetrafluoropropene (1234E) can be progressed in catalyst-free and high-temperature conditions with no addition of a radical generating agent. The isomerization of cis-1,3,3,3-tetrafluoropropene (1234Z) in the catalyst-free and high-temperature conditions is substantially the same as the isomerization reaction of trans-1-chloro-3,3,3-trifluoro-1-propene described above regarding the method for producing cis-1-chloro-3,3,3-trifluoro-1-propene (1233Z) except for the material compound to be used and the reaction temperature. For isomerizing cis-1,3,3,3-tetrafluoropropene (1234Z) in a catalyst-free condition, the reaction temperature is higher than or equal to 500° C. and lower than or equal to 900° C., and preferably higher than or equal to 600° C. and lower than or equal to 800° C. 1,3,3,3-tetrafluoropropene (1234EZ) is a compound more stable than 1-chloro-3,3,3-trifluoro-1-propene (1233EZ) and is not likely to be turned into tar or oil even at a temperature higher than or equal to 600° C. and lower than or equal to 800° C. Therefore, the isomerization can be efficiently performed in a temperature range higher than or equal to 600° C. and lower than or equal to 800° C. The isomerization reaction of 1234Z into 1234E in a catalyst-free condition is not advantageous for thermal equilibrium. Therefore, a high yield cannot be expected in the above-described practically usable temperature range. Thus, for causing an isomerization reaction of 1234Z into 1234E in a catalyst-free condition, it is preferable that the reaction product is separated into 1234E as the target compound and unreacted 1234Z and that the separated 1234Z is recovered and reused as a material composition.

According to the present invention, as described above regarding the method for producing cis-1-chloro-3,3,3-trifluoro-1-propene (1233Z), the method for producing trans-1-chloro-3,3,3-trifluoro-1-propene (1233E), the method for producing cis-1,3,3,3-tetrafluoropropene (1234Z) and the method for producing trans-1,3,3,3-tetrafluoropropene (1234E), a radical generating agent is added in an isomerization step of each of 1-chloro-3,3,3-trifluoro-1-propene (1233) and 1,3,3,3-tetrafluoropropene (1234). Thus, the resultant radical acts as a catalyst, so that a desired isomerization reaction of 1-chloro-3,3,3-trifluoro-1-propene or 1,3,3,3-tetrafluoropropene is caused and a high conversion ratio is provided even with no use of a solid catalyst. Therefore, a desired isomer of 1-chloro-3,3,3-trifluoro-1-propene or 1,3,3,3-tetrafluoropropene can be obtained stably with no undesired possibility that the solid catalyst is deteriorated due to coking or the like caused as a result of long-time use thereof.

A method for producing 1-chloro-3,3,3-trifluoro-1-propene and a method for producing 1,3,3,3-tetrafluoropropene according to the present invention respectively produce a highly pure desired isomer of 1-chloro-3,3,3-trifluoro-1-propene and a highly pure desired isomer of 1,3,3,3-tetrafluoropropene efficiently, and therefore are usable for industrial production of foaming agents for hard polyurethane foam, solvents, washing detergents, coolants, working fluids, sprays, agromedical intermediates, materials of fluorine resins and the like.

What is claimed is:

1. A method for producing a compound of a general formula (2), the method comprising isomerizing at least a part of a compound of a general formula (1) in a material composition into the compound of the general formula (2) by heating the material composition containing at least the compound of the general formula (1) in the presence of a radical generating agent, wherein, in the general formulas (1) and (2), each of X and Y is a fluorine atom (F) or a hydrogen atom (H), and X and Y are not the same as each other; or each of X and Y is a chlorine atom (Cl) or a hydrogen atom (H), and X and Y are not the same as each other; and when in the general formulas (1) and (2), X is a hydrogen atom (H) and Y is a fluorine atom (F), the material composition is heated at a temperature higher than or equal to 150° C. and lower than or equal to 700° C. in isomerizing; or when in the general formulas (1) and (2), X is a fluorine atom (F) and Y is a hydrogen atom (H), the material composition is heated at a temperature higher than or equal to 150° C. and lower than or equal to 700° C. in isomerizing; or when in the general formulas (1) and (2), X is a hydrogen atom (H) and Y is a chlorine atom (Cl), the material composition is heated at a temperature higher than or equal to 150° C. and lower than or equal to 800° C. in isomerizing; or when in the general formulas (1) and (2), X is a chlorine atom (Cl) and Y is a hydrogen atom (H), the material composition is heated at a temperature higher than or equal to 150° C. and lower than or equal to 800° C. in isomerizing

[Chemical formula 1]

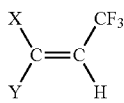
(1)

[Chemical formula 2]

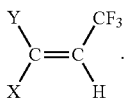
(2)

2. The method according to claim 1, wherein when in the general formulas (1) and (2), X is a hydrogen atom (H) and Y is a chlorine atom (Cl), the method includes, before the isomerizing:

reacting 1,1,1,3,3-pentachloropropane with hydrogen fluoride to generate a first composition containing compounds of the general formula (1) and the general formula (2) and at least one compound selected from the group consisting of 3-chloro-1,1,1,3-tetrafluoropropane (244fa), 2-chloro-1,1,1,3,3-pentafluoropropane (235da), and 1-chloro-1,1,4,4,4-pentafluoro-2-butene (1335);

removing the compound of the general formula (2) from the first composition by distillation; and removing the at least one compound selected from the group consisting of 3-chloro-1,1,1,3-tetrafluoropropane, 2-chloro-1,1,1,3,3-pentafluoropropane, and 1-chloro-1,1,4,4,4-pentafluoro-2-butene by distillation from the first composition deprived of the compound of the general formula (2) to provide the compound represented by the general formula (1).

3. The method according to claim 1, wherein the radical generating agent is at least one selected from the group consisting of chlorine, oxygen, bromine, air, hydrogen peroxide, ozone, nitrogen oxide, and carbon halide.

4. The method according to claim 1, wherein isomerizing is performed in a gas phase.

5. The method according to claim 1, wherein isomerizing is performed in the absence of a solid catalyst.

6. The method according to claim 1, wherein isomerizing is performed in an empty column of a gas phase flow system.

7. The method according to claim 1, wherein the radical generating agent is added in an amount, with respect to the compound of the general formula (1), higher than or equal to 0.0001 mol % and lower than or equal to 10 mol %.

8. The method according to claim 1, wherein when in the general formulas (1) and (2), X is a hydrogen atom (H) and Y is a fluorine atom (F), the material composition is heated at a temperature higher than or equal to 150° C. and lower than or equal to 700° C. in isomerizing.

9. The method according to claim 1, wherein when in the general formulas (1) and (2), X is a fluorine atom (F) and Y is a hydrogen atom (H), the material composition is heated at a temperature higher than or equal to 150° C. and lower than or equal to 700° C. in isomerizing.

10. The method according to claim 1, wherein when in the general formulas (1) and (2), X is a hydrogen atom (H) and Y is a chlorine atom (Cl), the material composition is heated at a temperature higher than or equal to 150° C. and lower than or equal to 800° C. in isomerizing.

11. The method according to claim 1, wherein when in the general formulas (1) and (2), X is a chlorine atom (Cl) and Y is a hydrogen atom (H), the material composition is heated at a temperature higher than or equal to 150° C. and lower than or equal to 800° C. in isomerizing.

12. A method for producing a compound of a general formula (2), the method comprising isomerizing at least a part of a compound of a general formula (1) in a material composition into the compound of the general formula (2) by heating the material composition containing at least the compound of the general formula (1) in the absence of a catalyst to a temperature higher than or equal to 450° C. and lower than or equal to 700° C. and setting a residence time to longer than or equal to 0.01 seconds and shorter than or equal to 50 seconds, wherein, in the general formulas (1) and (2), each of X and Y is a chlorine atom (Cl) or a hydrogen atom (H), and X and Y are not the same as each other

(1)

-continued

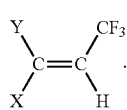
(2)

13. The method according to claim 12, wherein the residence time is longer than or equal to 0.1 seconds and shorter than or equal to 10 seconds.

14. A method for producing a compound of a general formula (2), the method comprising isomerizing at least a part of a compound of a general formula (1) in a material composition into the compound of the general formula (2) by heating the material composition containing at least the compound of the general formula (1) in the absence of a catalyst to a temperature higher than or equal to 500° C. and lower than or equal to 900° C. and setting a residence time to longer than or equal to 0.01 seconds and shorter than or equal to 50 seconds, wherein, in the general formulas (1) and (2), each of X and Y is a fluorine atom (F) or a hydrogen atom (H), and X and Y are not the same as each other

[Chemical formula 5]

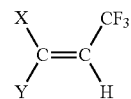
(1)

[Chemical formula 6]

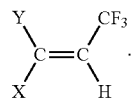
(2)

15. The method according to claim 14, wherein the residence time is longer than or equal to 0.1 seconds and shorter than or equal to 10 seconds.

* * * * *